US011236363B2

(12) United States Patent
Graves et al.

(10) Patent No.: US 11,236,363 B2
(45) Date of Patent: Feb. 1, 2022

(54) HYBRID PROTEINS AND USES THEREOF

(71) Applicant: SYMVIVO CORPORATION, Burnaby (CA)

(72) Inventors: Herbert Alexander Graves, Vancouver (CA); Mark Andrew Fox, Vancouver (CA)

(73) Assignee: Symvivo Corporation, Burnaby (CA)

( * ) Notice: Subject to any disclaimer, the term of this patent is extended or adjusted under 35 U.S.C. 154(b) by 0 days.

(21) Appl. No.: 16/554,392

(22) Filed: Aug. 28, 2019

(65) Prior Publication Data
US 2019/0376092 A1  Dec. 12, 2019

Related U.S. Application Data

(62) Division of application No. 15/298,706, filed on Oct. 20, 2016, now Pat. No. 10,435,716, which is a division of application No. 14/621,315, filed on Feb. 12, 2015, now abandoned.

(60) Provisional application No. 61/940,274, filed on Feb. 14, 2014, provisional application No. 61/940,258, filed on Feb. 14, 2014, provisional application No. 62/013,852, filed on Jun. 18, 2014.

(51) Int. Cl.
| | |
|---|---|
| *C12N 15/74* | (2006.01) |
| *C07K 1/00* | (2006.01) |
| *C07H 21/04* | (2006.01) |
| *C12N 15/90* | (2006.01) |
| *C07K 14/005* | (2006.01) |
| *C07K 19/00* | (2006.01) |
| *C12N 7/00* | (2006.01) |
| *C12N 9/24* | (2006.01) |
| *C12N 15/64* | (2006.01) |
| *C07K 14/46* | (2006.01) |
| *A61K 31/70* | (2006.01) |

(52) U.S. Cl.
CPC .......... *C12N 15/907* (2013.01); *C07K 14/005* (2013.01); *C07K 14/463* (2013.01); *C07K 19/00* (2013.01); *C12N 7/00* (2013.01); *C12N 9/2402* (2013.01); *C12N 15/64* (2013.01); *C12N 15/746* (2013.01); *C12N 15/902* (2013.01); *C07K 2319/02* (2013.01); *C07K 2319/10* (2013.01); *C07K 2319/80* (2013.01); *C07K 2319/81* (2013.01); *C12N 2740/16031* (2013.01); *C12N 2740/16311* (2013.01); *C12Y 302/01055* (2013.01)

(58) Field of Classification Search
CPC .... C12N 15/907; C12N 15/64; C12N 15/746; C07K 19/00; C07K 2319/02; C07K 2319/10; C07K 2319/80; C07K 2319/81
See application file for complete search history.

(56) References Cited

U.S. PATENT DOCUMENTS

| | | |
|---|---|---|
| 4,273,875 A | 6/1981 | Manis |
| 4,567,146 A | 1/1986 | Brewin et al. |
| 4,683,195 A | 7/1987 | Mullis et al. |
| 4,683,202 A | 7/1987 | Mullis |
| 4,800,159 A | 1/1989 | Mullis et al. |
| 4,994,370 A | 2/1991 | Silver et al. |
| 5,380,653 A | 1/1995 | Palva |
| 5,807,746 A | 9/1998 | Lin et al. |
| 6,007,988 A | 12/1999 | Choo et al. |
| 6,881,825 B1 | 4/2005 | Robbins et al. |
| 8,021,653 B2 | 9/2011 | Kano et al. |
| 8,535,939 B2 | 9/2013 | Shimatani-Shibata et al. |
| 8,569,065 B2 | 10/2013 | Polach et al. |
| 2005/0147993 A1* | 7/2005 | Khan |
| 2006/0182736 A1 | 8/2006 | Kim et al. |

FOREIGN PATENT DOCUMENTS

| | | |
|---|---|---|
| EP | 0320308 A2 | 6/1989 |
| WO | 90/07641 A1 | 7/1990 |
| WO | 00/58488 A2 | 10/2000 |
| WO | 2004/108883 A2 | 12/2004 |
| WO | 2015/120541 A1 | 8/2015 |

OTHER PUBLICATIONS

Liu et al. Mechanistic studies of intracellular delivery of proteins by cell-penetrating peptides in cyanobacteria. BMC Microbiology 13:57, 9 pages, (Year: 2013).*
Bechara, et al., "Cell-penetrating peptides: 20 years later, where do we stand?," FEBS letters, vol. 587, pp. 1693-1702 (2013).
Bryksin, et al., "Rational Design of a Plasmid Origin That Replicates Efficiently in Both Gram-Positive and Gram-Negative Bacteria," PloS ONE, vol. 5:10, pp. 1-9 (2010).
Christy, et al., "DNA binding site of the growth factor-inducible protein Zif268," Proc. Nat. Acad. Sci., vol. 86, pp. 8737-8741 (1989).
Chugh, et al. "Cell-penetrating peptides: Nanocarrier for macromolecule delivery in living cells." IUBMB life 62, No. 3 (2010): 183-193.
Deng, et al., "Signal peptide of Arabinosidase enhances secretion of interferon-α2b protein by *Bifidobacterium longum*," Arch Microbio., vol. 191, pp. 681-686 (Sep. 2009).
Fuhrmann, et al., "A synthetic gene coding for the green fluorescent protein (GFP) is a versatile reporter in *Chlamydomonas reinhardtii*," Plant J., vol. 19(3), pp. 353-361 (Aug. 1999).
Gao et al. "A plasmid display platform for the selection of peptides exhibiting a functional cell-penetrating phenotype." Biotechnology progress 26, No. 6 (2010): 1796-1800.

(Continued)

*Primary Examiner* — Quang Nguyen
(74) *Attorney, Agent, or Firm* — Kilpatrick Townsend & Stockton LLP

(57) ABSTRACT

There are disclosed hybrid proteins comprising at least one signal sequence; at least one DNA binding domain; and at least one cell penetrating peptide (CPP) domain. In embodiments the CPP domain is a TAT domain, and the DNA binding domain is a HU domain. There is also disclosed the use of the hybrid proteins to introduce exogenous DNA into target cells, and methods for introducing exogenous DNA into target cells using the hybrid proteins.

10 Claims, 10 Drawing Sheets

Specification includes a Sequence Listing.

(56) References Cited

OTHER PUBLICATIONS

Gao, et al., "Thermodynamically balanced inside-out (TBIO) PCR-based gene synthesis: a novel method of primer design for high-fidelity assembly of 10 longer gene sequences," Nucleic Acids Res., vol. 31(22): e143. (Nov. 2003).
Goeddel, et al., "Synthesis of human fibroblast interferon by *E. coli*," Nucleic Acids Res., vol. 8, pp. 4057-4074 (1980).
Grangette, et al., "Enhanced Mucosal Delivery of Antigen with Cell Wall Mutants of Lactic Acid Bacteria," Infect. Immun., vol. 72, pp. 2731-2737 (2004).
Hillson, et al., "j5 DNA Assembly Design Automation Software" ACS Synthetic Biology, vol. 1(1), pp. 14-21 (2012).
Hoover, et al., "DNAWorks: an automated method for designing oligonucleotides for PCR-based gene synthesis," Nucleic Acids Res., vol. 30(10): e43 (May 2002).
Itakura, et al., "Expression in *Escherichia coli* of a chemically synthesized gene for the hormone somatostatin," Science 198:4321, pp. 1056-1063 (Dec. 1977).
Joliot, et al., "Transduction peptides: from technology to physiology," Nature, vol. 6, No. 3, pp. 189-196 (2004).
Khokhlova, et al., "*Bifidobacterium longum* Modifed Recombinant HU Protein as a Vector for Nonviral Delivery of DNA to HEK293 Human Cell Culture" 151 Bulletin of Experimental Biology and Medicine, pp. 717-721. (2011).
Khorana, et al., "Studies on Polynucleotides. Total Synthesis of the Structural Gene for an Alanine Transfer Ribonucleic Acid from Yeast," J. Mol. Biol., vol. 72(2), pp. 209-217 (Dec. 1972).
Knudsen, et al., "Development of Efficient Suicide Mechanisms for Biological Containment of Bacteria," App. and Env. Microbiol., vol. 57, No. 1, pp. 85-92 (1991).
Koren, et al., "Cell-penetrating peptides: breaking through to the other side," Trends in molecular medicine 18, No. 7 (2012): 385-393.
Margus, et al., "Cell-penetrating Peptides as Versatile Vehicles for Oligonucleotide Delivery," Molecular Therapy, vol. 20, pp. 525-533 (Mar. 2012).
Moon, et al., "Secretion of Recombinant Pediocin PA-1 by *Bifidobacterium longum*, Using the Signal Sequence for Bifidobacterial α-Amylase," Applied and Environmental Microbiology, pp. 5630-5632 (2005).
Rao, et al., "Toward a live microbial microbicide for HIV: Commensal bacteria secreting an HIV fusion inhibitor peptide," PNAS, vol. 102, No. 34, pp. 11993-11998 (2005).
Roy, et al., "Cell carriers for oncolytic viruses: current challenges and future directions," Oncolytic Virotherapy, 2013, 2, 47-56.
Salomone, et al., "A novel chimeric cell-penetrating peptide with membrane disruptive properties for efficient endosomal escape," J Control. Release., vol. 163(3) pp. 293-303 (Oct. 2012).
Sera, "Generation of Cell-Permeable Artificial Zinc Finger Protein Variants," Methods in Molecular Biology, vol. 649, pp. 91-96 (2010).
Shaw, et al., "Comparison of Protein Transduction Domains in Mediating Cell Delivery of a Secreted CRE Protein," Biochemistry 2008, 47, 1157-1166.
Signal Peptide Website, An Information Platform for Signal Sequences and Signal Peptides, downloaded on Aug. 27, 2015 from www.signalpeptide.de.
Smith, et al., "Novel "Three-in-One" Peptide Device for Genetic Drug Delivery," Protein and Peptide Letters, vol. 10:1, pp. 1-7 (2003).
SPdb—Signal Peptide 10 Resource at downloaded on Aug. 27, 2015 from http://proline.bic.nus.edu.sg.
Stemmer, et al., "Single-step assembly of a gene and entire plasmid from large numbers of oligodeoxyribonucleotides," Gene, vol. 164(1), pp. 49-53 (Oct. 1995).
Stentz, et al., "Controlled Release of Protein from viable *Lactococcus lactis* Cells," Applied and Environmental Microbiology, vol. 76, pp. 3026-3031 (2010).
Stritzker, et al., "Tumor-specific colonization, tissue distribution, and gene induction by probiotic *Escherichia coli* Nissle 1917 in live mice," Intl. J. Med. Microbiol., vol. 297, pp. 151-162 (2007).
Sugita, et al., "Comparative study on transduction and toxicity of protein transduction domains," Br J Pharmacol., vol. 153(6): 1143-1152 (Mar. 2008).
Tian, et al., "Accurate multiplex gene synthesis from programmable DNA microchips," Nature 432 (7020): pp. 1050-1054 (Dec. 2004).
Villalobos, et al., "Gene Designer: a synthetic biology tool for constructing artificial DNA segments,". BMC Bioinformatics, vol. 7: 285 (2006).
Welch, et al., "Design Parameters to Control Synthetic Gene Expression in *Escherichia coli*," PLoS ONE, vol. 4 (9): e7002 (2009).
Young, et al., "Two-step total gene synthesis method". Nucleic Acids Res., vol. 32 (7): e59 (2004).
Yazawa, et al., "Bifidobacterium longum as a delivery system for cancer gene therapy: selective localization and growth in hypoxic tumors." Cancer gene therapy 7, No. 2 (2000): 269.

\* cited by examiner pBRA 2.0-SHT pFRG 1.5 SHT

Figure 3. SHT and SZT interact with pBRA2.0 and result in gel-shift with increasing concentrations of peptide

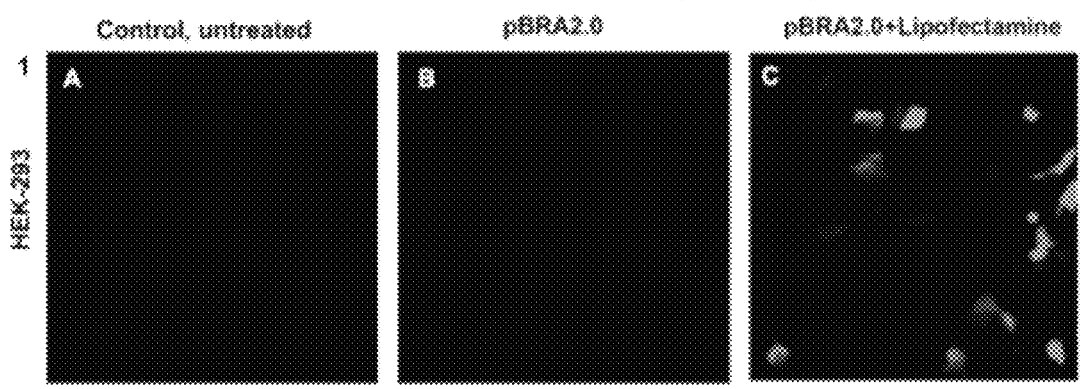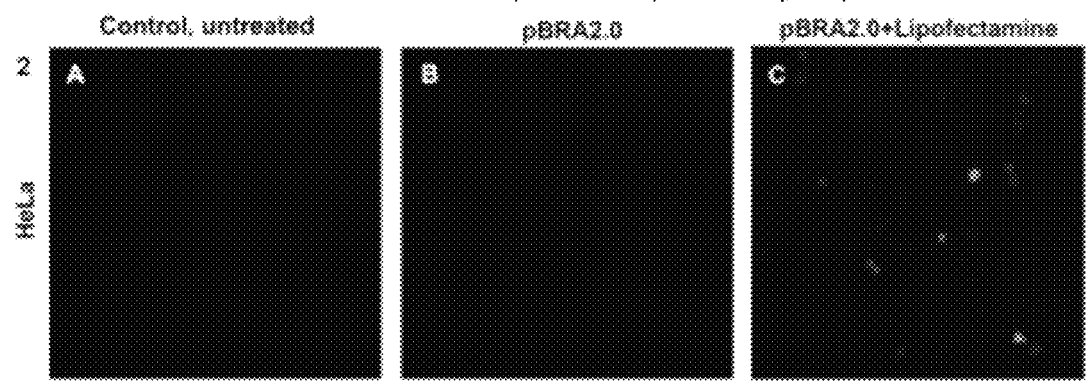
FIG. 5

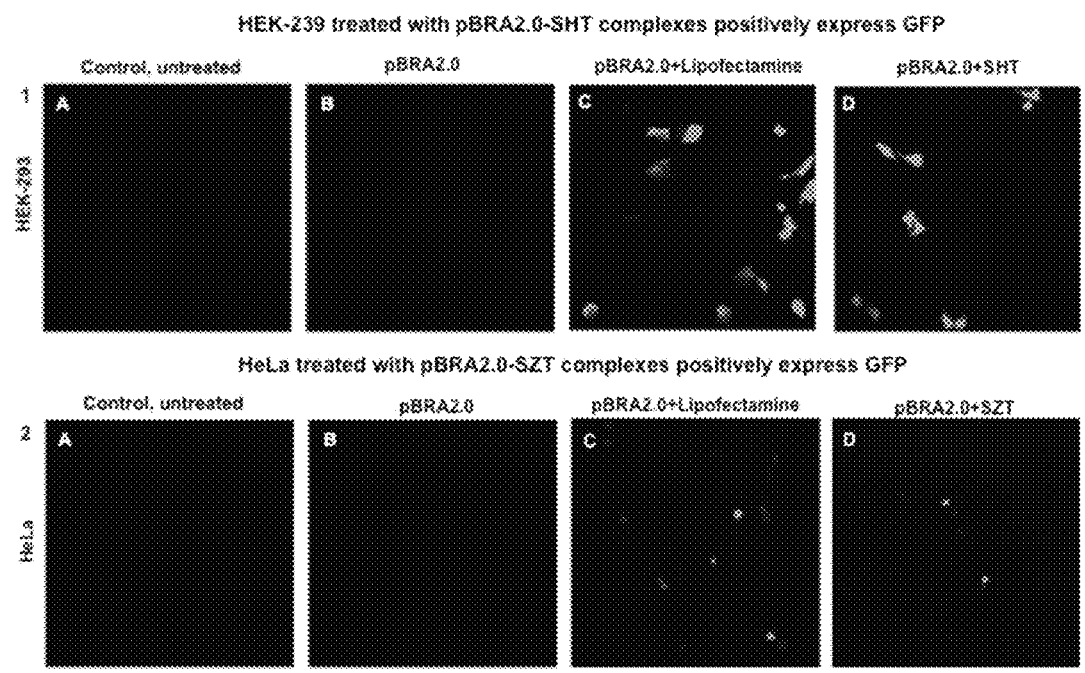
Figure 10 Therapeutic molecules pBRA2.0-SHT and pBRA2.0-SZT complexes can transfect and express GFP in mammalian cell lines.

HYBRID PROTEINS AND USES THEREOF

PRIORITY CLAIMS

This application is a Divisional Application of Ser. No. 15/298,706, filed Oct. 20, 2016, which is a Divisional Application of U.S. application Ser. No. 14/621,315, filed Feb. 12, 2015, which claims priority under 35 USC § 119(e) of U.S. provisional patent application No. 61/940,274, filed Feb. 14, 2014, U.S. provisional patent application No. 61/940,258 filed Feb. 14, 2014; and U.S. provisional patent application No. 62/013,852 filed Jun. 18, 2014. The specifications of which are incorporated by reference herein for all purposes.

BACKGROUND

1. Field

The Subject matter disclosed generally relates to hybrid proteins and the use of the hybrid proteins to transform prokaryotic and eukaryotic cells.

2. Related Art

A variety of vectors and methods are known in the art for propagating nucleic acid sequences in bacteria and for introducing nucleic acid sequences into different types of bacteria and into eukaryotic cells. The following publications are of note:

Salomone, F., et al., "A novel cell-penetrating peptide with membrane disruptive properties for efficient endosomal escape" (2010), Journal of controlled release 163 (293-303).

Stentz, R. et al., "Controlled release of protein from viable *Lactococcus* cells" (2010) Applied and Environmental Microbiology 76, 3026-3031.

Christy, B., and Nathans, D. "DNA binding site of the growth factor-inducible protein Zif268" (1989) 86 Proc. Nat. Acad. Sci. 8737-8741.

Khokhlova, E. V., et al., "*Bifidobacterium Longum* Modified recombinant HU protein as vector for nonviral delivery of DNA to HEK293 Human cell culture" (2011) 151 Bulletin of Experimental Biology and Medicine 717-721.

SUMMARY

In an embodiment there is disclosed a hybrid protein comprising: at least one signal sequence; at least one DNA binding domain; and at least one cell penetrating peptide (CPP) domain.

In alternative embodiments, at least one CPP domain is a TAT domain, a VP22 domain, an Antp domain, a Rev domain, a P-beta (gp41-SV40) domain, a Transportan (Galanin-mastoparan) domain or a Pep-1 (Trp-rich motif SV40) domain.

In alternative embodiments, at least one secretion signal sequence is selected from the group consisting of an alpha amylase signal sequence, a truncated alpha amylase signal sequence and an alpha arabinosidase signal sequences.

In alternative embodiments, at least one DNA binding domain is a sequence specific DNA binding domain.

In alternative embodiments, at least one DNA binding domain comprises at least one domain selected from the group consisting of: a Zinc finger DNA binding domain, a homeobox DNA binding domain, a MerR DNA binding domain, and a HU DNA binding domain.

In alternative embodiments, the hybrid protein may comprise an alpha arabinosidase signal sequence, a TAT domain and a HU DNA binding domain.

In an embodiment there is disclosed a method for transforming a target cell with a desired DNA, the method comprising the step of: contacting the target cell with a protein-DNA complex comprising the desired DNA and the hybrid protein disclosed herein.

In alternative embodiments, the DNA is a plasmid.

In alternative embodiments, the plasmid comprises an expression cassette for expressing the hybrid protein in a gram positive bacterium.

In alternative embodiments, at least one DNA binding domain is a sequence specific DNA binding domain and wherein the plasmid comprises at least one nucleotide sequence for binding to at least one sequence specific DNA binding domain.

In alternative embodiments, at least one CPP sequence has at least 90% amino acid sequence identity over a sequence of at least 10 contiguous amino acids to SEQ ID NO: 11, 12, 13, 14, 15, 16, or 17.

In alternative embodiments, at least one signal sequence has at least 90% amino acid sequence identity over a sequence of at least 10 contiguous amino acids to SEQ ID NO: 19, 21 or 23.

In alternative embodiments, at least one DNA binding domain has at least 90% amino acid sequence identity over at least 10 amino acids to SEQ. ID. NO. 44, 45 or 46.

In alternative embodiments, the cell is a gram positive bacterium.

In alternative embodiments, the cell is a mammalian cell.

In alternative embodiments, the method may further comprise the step of contacting the DNA with the hybrid protein to form the protein-DNA complex.

In an embodiment there is disclosed a cell transformed with an exogenous DNA using the hybrid protein disclosed herein, wherein the cell is a gram positive bacterium or is a mammalian cell.

In an embodiment there is disclosed the use of the hybrid protein disclosed herein to transform a gram positive bacterium or a mammalian cell.

In an embodiment there is disclosed the use of the hybrid protein disclosed herein to transform a cell selected from the group consisting of: *Staphylococcus, streptococcus, Bifidobacterium, lactococcus, lactobacillus, clostridium.*

In an embodiment there is disclosed a kit for transforming a target cell with a desired DNA, the kit comprising a quantity of the hybrid protein disclosed herein, and instructions to: form a complex of the hybrid protein with the desired DNA; and contact the complex with the target cell.

In an embodiment there is disclosed a gram positive bacterium able to synthesize the novel hybrid protein disclosed herein.

In an embodiment there is disclosed a hybrid protein comprising: at least one CPP domain selected from the group consisting of a TAT domain, a VP22 domain, an Antp domain, a Rev domain, a P-beta (gp41-SV40) domain, a Transportan (Galanin-mastoparan) domain or a Pep-1 (Trp-rich motif SV40) domain; at least one DNA binding domain selected from the group consisting of a Zinc finger DNA binding domain, a homeobox DNA binding domain, a MerR DNA binding domain, and a HU DNA binding domain; and at least one signal sequence selected from the group consisting of alpha amylase signal sequence, a truncated alpha amylase signal sequence and an alpha arabinosidase signal sequence.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

FIG. 5 shows the results of transfecting HEK-293 and HeLa cells with pBRA2.0 SHT vector according to an embodiment of the present subject matter.

FIG. 10 shows the transfection of mammalian cells by protein complexes comprising pBRA2.0-SHT or pBRA2.0-SZT, and the expression of the cargo GFP sequences in the mammalian cell lines. Therapeutic molecules pBRA2.0-SHT and pBRA2.0-SZT complexes can transfect and express GFP in mammalian cell lines.

DETAILED DESCRIPTION OF EMBODIMENTS

Figure 1:
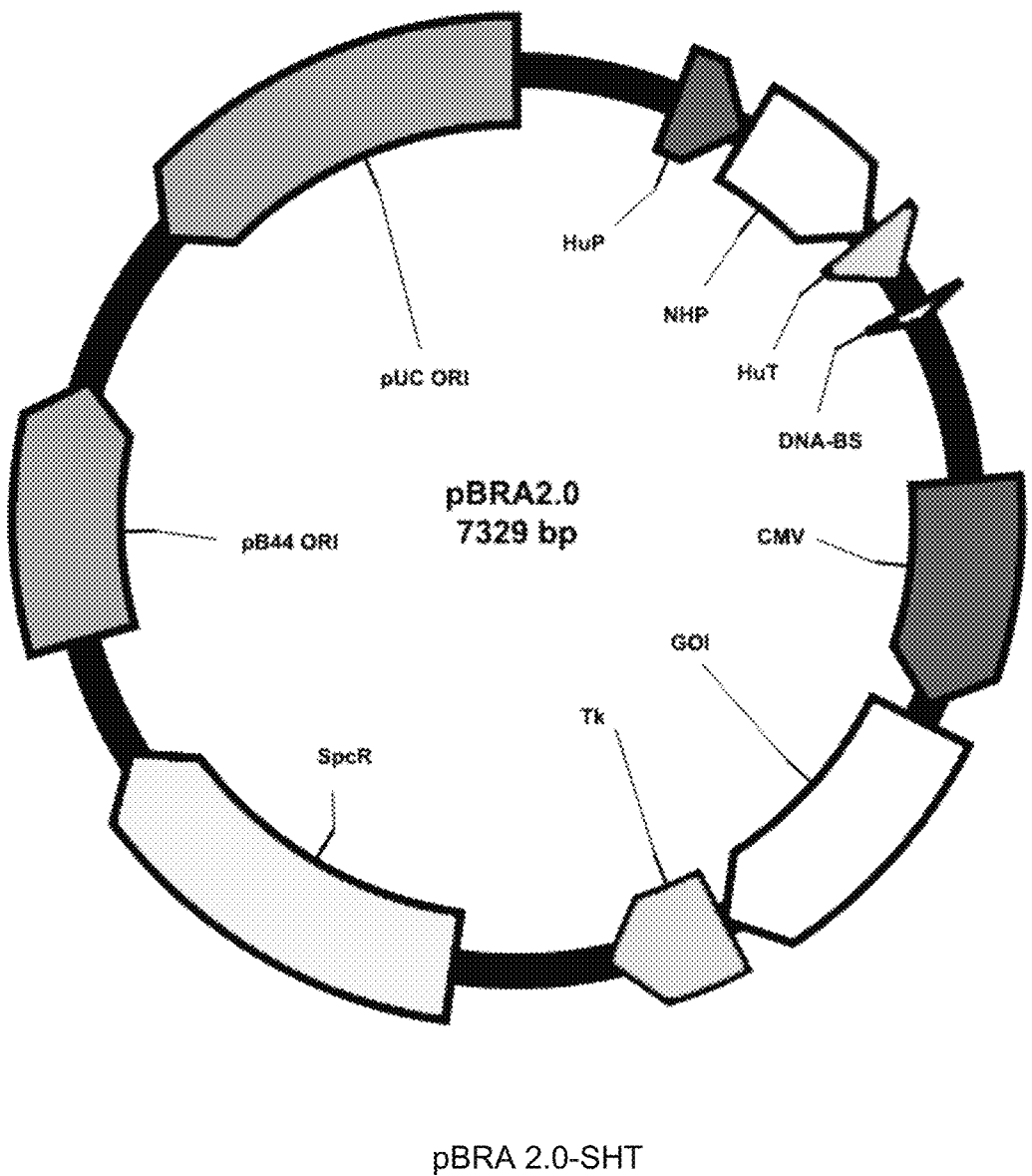
FIG. 1. shows the structure of a vector according to a first embodiment of the present subject matter and identified as pBRA2.0 SHT.

The following sequence listings are presented herein and form a part of this disclosure:

SEQ ID NO: 1 is the sequence of pBRA2.0 SHT wherein the eukaryotic expression cassette encodes GFP protein and the prokaryotic expression cassette encodes the SHT protein. Source: Artificial.

SEQ ID NO: 2. is the sequence of pFRG1.5-SHT wherein the eukaryotic expression cassette comprises the green fluorescent protein (GFP) gene. Source: Artificial.

SEQ ID NO: 3 is the nucleotide sequence encoding the Lac I DNA binding domain according to embodiments. Source: *E. coli*.

SEQ ID NO: 4 is the nucleotide sequence encoding the HU DNA binding domain according to embodiments. Source: *Bifidobacterium*.

SEQ ID NO: 5 is the nucleotide sequence encoding the Mer R DNA binding domain according to embodiments. Source: *Bifidobacterium*.

SEQ ID NO: 6 is the nucleotide sequence encoding the Zinc finger DNA binding domain according to embodiments. Source: Artificial.

SEQ ID NO: 7 is the nucleotide sequence encoding the SMT hybrid protein Source: Artificial.

SEQ ID NO: 8 is the nucleotide sequence encoding the SHT hybrid protein. Source: Artificial.

SEQ. ID. NO. 9 is the nucleotide sequence encoding the SLT hybrid protein. Source: Artificial.

SEQ ID NO: 10 is the nucleotide sequence encoding the SZT hybrid protein. Source: Artificial.

SEQ ID NO: 11 is the amino acid sequence of the Trans-Activator of Transcription (Tat) transduction domain [HIV].

SEQ ID NO: 12 is the amino acid sequence of the Antennapedia (Antp) transduction domain Source: *Drosophila Melanogaster*.

SEQ ID NO: 13 is the amino acid sequence of the HIV Rev transduction domain. Source: Human HIV virus.

SEQ ID NO: 14 is the amino acid sequence of the herpes simplex virus VP22 transduction domain. Source: Human HSV virus.

SEQ ID NO: 15 is the amino acid sequence of the P-beta MPG (gp41-SV40) transduction domain. Source: SV40.

SEQ ID NO: 16 is the amino acid sequence of the Transportan (Galanin-mastoparan) transduction domain Source: Eukaryote, species unknown.

SEQ ID NO: 17 is the amino acid sequence of the Pep-1 (Trp-rich motif-SV40) transduction domain. Source: SV40

SEQ ID NO: 18 is the DNA sequence encoding the alpha amylase signal sequence comprising a cleavage site. Source: *Bifidobacterium*.

SEQ ID NO: 19 is the 46 amino acid sequence encoding the alpha amylase signal sequence including a putative cleavage site. Source: *Bifidobacterium*.

SEQ ID NO: 20 is the DNA sequence encoding the cleaved alpha amylase signal sequence. Source: *Bifidobacterium*.

SEQ ID NO: 21 is the 44 amino acid sequence of the cleaved alpha amylase signal sequence. Source: *Bifidobacterium*.

SEQ ID NO: 22 is the DNA sequence encoding the alpha arabinosidase signal sequence. Source: *Bifidobacterium*.

SEQ ID NO: 23 is the amino acid sequence for the alpha arabinosidase signal sequence. Source: *Bifidobacterium*.

SEQ ID NO: 24 is the amino acid sequence of the hybrid protein embodiment designated SHT. Source: Artificial.

SEQ ID NO: 25 is the amino acid sequence of the hybrid protein embodiment designated SLT. Source: Artificial.

SEQ ID NO: 26 is the amino acid sequence of the hybrid protein embodiment designated SMT. SOURCE: ARTIFICIAL.

SEQ ID NO: 27 is the amino acid sequence of the hybrid protein embodiment designated SZT Source: Artificial.

SEQ ID NO: 28 is a DNA sequence comprising the pDOJHR ORI. Source: *Bifidobacterium*.

SEQ ID NO: 29 is a DNA sequence comprising the pUC/*E. coli* ORI. Source: *E. coli*.

SEQ ID NO: 30 is a DNA sequence comprising the pB44 ORI. Source: *Bifidobacterium*.

SEQ ID NO: 31 is the DNA sequence encoding the TAT domain. Source: Human HIV virus.

SEQ ID NO: 32 is the DNA sequence encoding the P-beta MPG (gp41-SV40) Transduction domain. Source: SV40 virus.

SEQ ID NO: 33 is the DNA sequence encoding the Transportan (Galanin-mastoparan) transduction domain Source: eukaryote—species unknown, SEQ ID NO: 34 is the DNA sequence encoding the Pep-1 (Trp-rich motif-SV40) transduction domain. Source: SV40.

SEQ ID NO: 35 GFP forward primer Source: *Aequorea victoria*

SEQ ID NO: 36 GFP Reverse Primer. Source: *Aequorea victoria*

SEQ ID NO: 37 Spectinomycin Resistance Forward Primer. Source: *Streptomyces spectabilis.*

SEQ ID NO: 38 Spectinomycin Reverse Primer: Source: *Streptomyces spectabilis.*

SEQ ID NO: 39 CMV Forward Primer. Source: *Cytomegalovirus.*

SEQ ID NO: 40 CMV Reverse Primer. Source: *Cytomegalovirus.*

SEQ ID NO: 41 MerR DNA recognition site. Source: *Bifidobacterium.*

SEQ ID NO: 42 Lad repressor DNA binding site. Source. *E. Coli.*

SEQ ID NO: 43 Synthetic zinc finger DNA recognition site. Source: Artificial.

SEQ ID NO: 44 HU DNA binding domain. Source: *Bifidobacterium.*

SEQ ID NO: 45 Mer R DNA binding domain. Source: *Bifidobacterium.*

SEQ ID NO: 46 Zn finger DNA binding domain. Source: Artificial.

SEQ ID NO: 47 Lac I DNA binding domain. Source: *E. coli. E. coli.*

SEQ ID NO: 48 Prokaryotic expression cassette from pFRG (FIG. 2) comprising Hu Promoter and terminator. Source: Artificial/*bifidobacteria.*

SEQ ID NO: 49 Eukaryotic Expression Cassette from pFRG (FIG. 2) comprising CMV promoter, Kozak sequence and TK Poly A site and terminator, flanking GFP coding sequences to be expressed. Source: Artificial.

Definition of Terms: In this disclosure, the word "comprising" is used in a non-limiting sense to mean that items following the word are included, but items not specifically mentioned are not excluded. A reference to an element by the indefinite article "a" does not exclude the possibility that more than one of the elements is present, unless the context clearly requires that there be one and only one of the elements.

In this disclosure the recitation of numerical ranges by endpoints includes all numbers subsumed within that range including all whole numbers, all integers and all fractional intermediates (e.g., 1 to 5 includes 1, 1.5, 2, 2.75, 3, 3.80, 4, and 5 etc.).

In this disclosure the singular forms a "an", and "the" include plural referents unless the content clearly dictates otherwise. Thus, for example, reference to a composition containing "a compound" includes a mixture of two or more compounds.

In this disclosure term "or" is generally employed in its sense including "and/or" unless the content clearly dictates otherwise.

In this disclosure, unless otherwise indicated, all numbers expressing quantities or ingredients, measurement of properties and so forth used in the specification and claims are to be understood as being modified in all instances by the term "about". Accordingly, unless indicated to the contrary or necessary in light of the context, the numerical parameters set forth in the disclosure are approximations that can vary depending upon the desired properties sought to be obtained by those skilled in the art utilizing the teachings of the present disclosure and in light of the inaccuracies of measurement and quantification. Without limiting the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, their numerical values set forth in the specific examples are understood broadly only to the extent that this is consistent with the validity of the disclosure and the distinction of the subject matter disclosed and claimed from the prior art.

The nucleic acid vectors, also referred to as expression vectors, disclosed herein are able to replicate in both gram negative and gram positive bacteria. In embodiments the gram negative bacteria is *E. coli*. In embodiments the gram positive bacteria is *bifidobacteria*. In embodiments the gram positive bacterium is *staphylococcus*. In embodiments the gram positive bacterium is *streptococcus*. In embodiments the gram positive bacterium is *lactococcus*. In embodiments the gram positive bacterium is *clostridium* or is *lactobacillus*. The full range of possible target bacterial strains will be readily understood by one skilled in the art, and a listing of strains is available at LPSN bacterio.net at http://www.bacterio.net/-alintro.html, the contents of which is hereby incorporated herein where permissible by law. In particular embodiments the bacteria are probiotic bacteria or are GRAS bacteria.

In embodiments where the target gram positive bacteria is *Bifidobacteria*, then illustrative possible strains or species of *bifidobacteria*, without limitation, include:

*Bifidobacterium, Bifidobacterium actinocoloniiforme, Bifidobacterium adolescentis, Bifidobacterium angulatum, Bifidobacterium animalis, Bifidobacterium animalis* subsp. *animalis, Bifidobacterium animalis* subsp. *lactis, Bifidobacterium asteroids, Bifidobacterium biavatii, Bifidobacterium bifidum, Bifidobacterium bohemicum, Bifidobacterium bombi, Bifidobacterium bourn, Bifidobacterium breve, Bifidobacterium callitrichos, Bifidobacterium catenulatum, Bifidobacterium choerinum, Bifidobacterium coryneforme, Bifidobacterium vectocuniculi, Bifidobacterium denticolens, Bifidobacterium dentium, Bifidobacterium gallicum, Bifidobacterium gallinarum, Bifidobacterium globosum, Bifidobacterium indicum, Bifidobacterium infantis, Bifidobacterium inopinatum, Bifidobacterium kashiwanohense, Bifidobacterium lactis, Bifidobacterium longum, Bifidobacterium longum* subsp. *infantis, Bifidobacterium longum* subsp. *longum, Bifidobacterium longum* subsp. *suis, Bifidobacterium magnum, Bifidobacterium merycicum, Bifidobacterium minimum, Bifidobacterium mongoliense, Bifidobacterium pseudocatenulatum, Bifidobacterium pseudolongum, Bifidobacterium pseudolongum* sub sp. *globosum, Bifidobacterium pseudolongum* sub sp. *pseudolongum, Bifidobacterium psychraerophilum, Bifidobacterium pullorum, Bifidobacterium reuteri, Bifidobacterium ruminantium, Bifidobacterium saeculare, Bifidobacterium saguini, Bifidobacterium scardovii, Bifidobacterium stellenboschense, Bifidobacterium stercoris, Bifidobacterium subtile, Bifidobacterium suis, Bifidobacterium thermacidophilum, Bifidobacterium thermacidophilum* subsp. *porcinum, Bifidobacterium thermacidophilum* subsp. *thermacidophilum, Bifidobacterium thermophilum, Bifidobacterium tsurumiense; Bifidobacterium longum, Bifidodobacterium bifidum,* and *Bifidobacterium infantis.*

Where the target bacterium is *staphylococcus* then the illustrative possible strains or species of staphylococcus, without limitation, include:

*S. arlettae; S. agnetis; S. aureus; S. auricularis; S. capitis; S. caprae; S. carnosus; S. caseolyticus; S. chromogenes; S. cohnii; S. condimenti; S. delphini; S. devriesei; S. epidermidis; S. equorum; S. felis; S. fleurettii; S. gallinarum; S. haemolyticus; S. hominis; S. hyicus; S. intermedius; S. kloosii; S. leei; S. lentus; S. lugdunensis; S. lutrae; S. massiliensis; S. microti; S. muscae; S. nepalensis; S. pasteuri; S. pettenkoferi; S. piscifermentans; S. pseudintermedius; S. pseudolugdunensis; S. pulvereri; S. rostri; S. saccharolyticus; S. saprophyticus; S. schleiferi; S. sciuri; S. simiae; S. simulans; S. stepanovicii; S. succinus; S. vitulinus; S. warneri;* and *S. xylosus*.

In this disclosure the term "vector" refers to at least one of a plasmid, bacteriophage, cosmid, artificial chromosome, or other nucleic acid vector. In embodiments the vector encodes or is suitable to generate at least one therapeutic agent or comprises at least one therapeutic sequence. Vectors suitable for microbiological applications are well known in the art, and are routinely designed and developed for particular purposes. Some non-limiting published examples of vectors that have been used to transform bacterial strains include the following plasmids: pMW211, pBAD-DEST49, pDONRP4-P1R, pENTR-PBAD, pENTR-DUAL, pENTR-term, pBR322, pDESTR4-R3, pBGS18-N9uc8, pBS24Ub, pUbNuc, pIXY154, pBR322DEST, pBR322DEST-PBAD-DUAL-term, pJIM2093, pTG2247, pMEC10, pMEC46, pMEC127, pTX, pSK360, pACYC184, pBOE93, pBR327, pDW205, pKCL11, pKK2247, pMR60, pOU82, pR2172, pSK330, pSK342, pSK355, pUHE21-2, pEHLYA2-SD. See, for example, Stritzker, et al. Intl. J. Med. Microbiol. Vol. 297, pp. 151-162 (2007); Grangette et al., Infect. Immun. vol. 72, pp. 2731-2737 (2004), Knudsen and Karlstrom, App. and Env. Microbiol. pp. 85-92, vol. 57, no. 1 (1991), Rao et al., PNAS pp. 11193-11998, vol. 102, no. 34 (2005), each of which is incorporated herein by reference. Those skilled in the art, in light of the teachings of this disclosure, will understand that alternative embodiments of the subject matter claimed herein are possible and will understand how to combine sequences taken from known vectors in order to construct such alternative embodiments. By way of example, existing vectors from the foregoing list may be modified by inserting additional origins of replication, or additional expression cassettes (non-limiting examples of expression cassettes are presented as SEQ ID NOs 48 and 49) comprising suitable promoter and termination sequences, or additional DNA binding sequences, or coding sequences for the hybrid protein (NHP) described herein. Those skilled in the art will understand and adopt the various alternatives known in the art, and will do so using techniques well known in the art. In particular embodiments, suitable origins of replication for use in embodiments include an origin of replication comprised within pDOJHR as well as the pB44 and pUC (*E. coli*) origins of replication. These are presented herein as SEQ ID NOs 28, 30, 29 respectively. In some embodiments adjacent functional components of a vector are joined by linking sequences.

In embodiments the vector comprises a eukaryotic expression cassette (a non-limiting example comprising GFP coding sequences is presented as SEQ ID NO: 49) containing a marker sequence to confirm both transformation and gene expression in the target eukaryotic cell. It will be understood that in alternative embodiments a range of alternative marker proteins and sequences are possible and for example in selected embodiments and without limitation the marker sequence encodes GFP (green fluorescent protein), RFP (red fluorescent protein), CAT (chloramphenicol acetyltransferase), luciferase, GAL (beta-galactosidase), or GUS (beta-glucuronidase). Those skilled in the art will readily understand and use all such marker sequences and reporter genes using standard techniques and materials readily available in the art.

Vectors according to embodiments comprise one or more prokaryotic expression cassettes. A non-limiting example of a prokaryotic expression cassette suitable for the expression of sequences in gram positive bacteria, and in embodiments in staphylococcus and *bifidobacteria* is presented as SEQ ID NO: 48. In embodiments such a cassette comprises a hybrid protein and embodiments of such hybrid proteins are disclosed herein.

It will be understood that in embodiments vectors may comprise at least or only one, two, three or more eukaryotic expression cassettes, or may comprise at least or only one, two, three or more prokaryotic expression cassettes for expression in gram positive bacteria, or may comprise combinations of the foregoing.

In this disclosure the term Cell penetrating peptide ("CPP") means a protein that is able to penetrate the cell membrane of a eukaryotic cell. The term CPP includes Tat, also referred to as a trans-activator of transcription. For greater certainty, but without limitation, reference to Tat or any other CPP will be understood to mean the native sequence, and also a full range of sequence variants thereof which are suitable to carry out the desired function of the protein or protein domain in question. By way of example, a range of functional variants of the Tat protein are described in F. Salomone et al., (2010) "A novel chimeric cell-penetrating peptide with membrane-disruptive properties for efficient endosomal escape" Journal of Controlled Release 163, 293-303.

Other non-limiting examples of CPP's according to embodiments include the VP22 protein of Herpes Simplex Virus, and the protein transduction domain of the Antennapedia (Antp) protein as well as the protein transduction domains presented in Table 1, namely Tat, Rev, Antp, VP22, Pep1 and Transportan. In embodiments the CPP domain is the domain described in Salomone F., et al, "A novel chimeric cell-penetrating peptide with membrane disruptive properties for endosomal escape." J Control. Release. 2012 Oct. 2 (epub ahead of print). Table 1 shows a non-limiting selection of exemplary CPP domains.

TABLE 1

| Sequences of exemplary CPP (transduction) domains | | |
|---|---|---|
| Tat | SEQ ID NO: 11 | YGRKKRRQRRR |
| Antp | SEQ ID NO: 12 | RQIKIWFQNRRMKWKK |
| Rev | SEQ ID NO: 13 | TRQARRNRRRRWREROF |
| VP22 | SEQ ID NO: 14 | NAKTRRHERRRKLAIER |
| P-beta MPG (gp41-SV40) | SEQ ID NO: 15 | GALFLGFLGAAGSTMGAWS QPKKKRKV-cys |
| Transportan (Galanin-mastoparan) | SEQ ID NO: 16 | GWTLNSAGYLLGKINLKAL AALAKKIL |
| Pep-1 (Trp-rich motif-SV40) | SEQ ID NO: 17 | KETWWETWWTEWSQPKKKRRV |

In this disclosure the term "DNA binding domain" means a protein sequence able to reversibly but tightly or with high affinity bind specifically to a suitable DNA sequence. In embodiments a DNA binding sequence may be a Zinc finger binding domain, and while a wide range of suitable domains and their complementary DNA binding sequences will be readily identified by those skilled in the art, a number of illustrative examples are disclosed in U.S. Pat. No. 6,007,988, issued on Dec. 28, 1999. In particular embodiments hereof, the DNA binding motif or domain is or is derived from, Mer R, Zinc finger, or Histone like DNA binding protein or is or is derived from the HU protein or is or is derived from a homeobox DNA binding protein. It will be understood that the HU protein is generally considered a homeobox-like protein.

While many types of DNA binding domains will be readily identified by those skilled in the art using available databases, screening methodologies and well known techniques, non-limiting examples of suitable DNA binding domains for use in alternative embodiments can be derived from a wide range of DNA binding proteins. In embodiments suitable DNA binding domains may be of any general type, including but not limited to helix-turn-helix, Zinc finger, leucine zipper, winged helix, winged helix turn helix, helix loop helix, HMG box, Wor 3 and RNA guided binding domains. Illustrative examples of DNA binding proteins whose DNA binding domains may be utilized in embodiments include histones, histone like proteins, transcription promoters, transcription repressors, transcriptional regulators, which may be drawn from a wide range of alternate sources and operons.

In this disclosure the terms "polypeptide", "peptide", "oligopeptide" and "protein" are used interchangeably herein to refer to a polymer of amino acid residues. The terms apply to amino acid polymers in which one or more amino acid residues is an artificial chemical analogue of a corresponding naturally occurring amino acid, or is a completely artificial amino acid with no obvious natural analogue as well as to naturally occurring amino acid polymers.

In embodiments the eukaryotic expression cassettes comprised in the vectors comprise suitable Kozak sequences, and the possible variations thereon and positioning thereof will be readily understood by those skilled in the art. One non limiting example is presented as SEQ ID NO: 49.

A peptide or peptide fragment is "derived from" a parent peptide or polypeptide if it has an amino acid sequence that is homologous to the amino acid sequence of, or is a conserved fragment from, the parent peptide or polypeptide. It will be understood that such sequences will, in alternative embodiments, comprise natural amino acids or will comprise artificially created amino acids. All of the foregoing will be readily identified by those skilled in the art.

In embodiments vectors have sequences which differ from the disclosed examples. It will be understood by those skilled in the art that a range of sequence variations are possible that do not affect or do not prevent the suitability of the vector for the purposes disclosed herein. By way of example and not limitation those skilled in the art will recognise that certain DNA sequences can be varied without materially affecting the function of the vector and others cannot. Again by way of illustration and not limitation, those skilled in the art will recognise and adopt sequence modifications known to enhance the function of a selected sequence, and will reject sequence modifications known to diminish such function. With particular reference to protein coding sequences those skilled in the art will recognise variable and conserved regions and will recognise mutations likely to change the structure and/or function of the relevant protein or polypeptide and those unlikely to do so. In general it will be understood that in particular variant embodiments the nucleic acid sequence of a vector will be 100% identical to one of the examples disclosed, or will be at least about, or about, or less than about 99%, 98%, 97%, 96%, 95%, 94%, 93%, 92%, 91%, 90%, 89%, 88%, 87%, 86%, 95%, 84%, 83%, 82%, 81%, or 80% identical to one of the examples disclosed and that in embodiments such sequence identity will extend over all or only part of the length of the vector. It will be understood that in embodiments vectors will comprise alternative origins of replication, promoters, polyadenylation sites and the like. In embodiments vectors will comprise sequences inserted in the expression cassettes, and in embodiments vectors will have no insertions in the expression cassettes.

In embodiments the hybrid protein or polypeptide sequence encoded by a sequence comprised in an expression cassette according to an embodiment is 100% identical to one of the examples disclosed, or is at least about, or about, or less than about 99%, 98%, 97%, 96%, 95%, 94%, 93%, 92%, 91%, 90%, 89%, 88%, 87%, 86%, 95%, 84%, 83%, 82%, 81%, or 80% identical to one of the examples disclosed as SEQ ID NOs 24, 25, 26, 27 and such sequence identity extends over all or only part of the length of the protein or polypeptide.

In embodiments homologies and sequence identities extend over all or only a part of the sequence or sequences of interest. In embodiments homologies and sequence identities are limited to particular functional or sequence domains. In embodiments homologies and sequence identities continuous and in embodiments are separated by regions of lower sequence identity or homology.

Construction of vectors: In embodiments vectors and sequences set out herein are synthesized de novo using known techniques and commercially available DNA synthesis services. Standard techniques for the construction of the vectors of the present invention are well-known to those of ordinary skill in the art and can be found in such references as Sambrook et al., Molecular Cloning: A Laboratory Manual, 2nd ed., Cold Spring Harbor Laboratory Press, New York, (1989). A variety of strategies are available for ligating fragments of DNA, the choice of which depends on the nature of the termini of the DNA fragments and which choices can be readily made by the skilled artisan. In embodiments the sequences of vectors are determined using suitable DNA, RNA and protein sequence manipulation software, and the desired sequence is synthesized using suitable synthesis methods, a wide variety of which are readily available and will be immediately understood and implemented by those skilled in the art.

As described herein, an aspect of the present disclosure concerns isolated nucleic acids and methods of use of isolated nucleic acids. Plasmid Preparations: Plasmid preparations and replication means are well known in the art. See for example, U.S. Pat. Nos. 4,273,875 and 4,567,146 incorporated herein in their entirety. Some embodiments of the present invention include providing a portion of genetic material of a target microorganism and inserting the portion of genetic material of a target microorganism into a plasmid for use as an internal control plasmid.

Nucleic acids used as a template for amplification are isolated from cells according to standard methodologies. (Sambrook et al., 1989) The nucleic acid may be genomic DNA or fractionated or whole cell RNA. Where RNA is used, it may be desired to convert the RNA to a complementary cDNA. Pairs of primers that selectively hybridize to nucleic acids corresponding to specific sequences are contacted with the isolated nucleic acid under conditions that permit selective hybridization. Once hybridized, the nucleic acid primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintilography of incorporated radiolabel or fluorescent label or even via a system using electrical or thermal impulse signals (Affymax technology; Bellus, 1994).

Primers: The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences may be employed. Primers may be provided in double-stranded or single-stranded form, although the single-stranded form is preferred. Specific primers used to amplify portions of vectors and nucleotide sequences according to embodiments are presented as SEQ ID NOs 35-40. Those skilled in the art will readily select alternative suitable primers for particular requirements.

Template Dependent Amplification Methods: A number of template dependent processes are available to amplify the sequences present in a given template sample. One of the best known amplification methods is the polymerase chain reaction (referred to as PCR) which is described in detail in U.S. Pat. Nos. 4,683,195, 4,683,202 and 4,800,159, and in Innis et al., 1990, each of which is incorporated herein by reference in its entirety.

A reverse transcriptase PCR amplification procedure may be performed in order to quantify the amount of mRNA amplified. Methods of reverse transcribing RNA into cDNA are well known and described in Sambrook et al., 1989. Alternative methods for reverse transcription utilize thermostable DNA polymerases. These methods are described in WO 90/07641 filed Dec. 21, 1990. Polymerase chain reaction methodologies are well known in the art. Other amplification methods are known in the art besides PCR such as LCR (ligase chain reaction), disclosed in European Application o. 320 308, incorporated herein by reference in its entirety.

In another embodiment, Qbeta Replicase, may also be used as still another amplification method in the present invention. In this method, a replicative sequence of RNA which has a region complementary to that of a target is added to a sample in the presence of an RNA polymerase. The polymerase will copy the replicative sequence which may then be detected.

Nucleic Acid Synthesis: Those skilled in the art will readily recognize a range of methods and apparatuses for synthesizing desired nucleic acid sequences. By way of example and not of limitation in a series of embodiments plasmids were synthesized in silico by GeneArt®, Life Technologies™

While the scope of the of methods for making embodiments includes any suitable methods (for example, Polymerase Chain Reaction, i.e., PCR, and nucleic acid sequence based amplification, i.e., NASBA) for amplifying at least a portion of the microorganism's genetic material, for one example, the present invention describes embodiments in reference to PCR technique.

Amplification of a genetic material, e.g., DNA, is well known in the art. See, for example, U.S. Pat. Nos. 4,683,202, and 4,994,370, which are incorporated herein by reference in their entirety. By knowing the nucleotide sequences of desired genetic material or target nucleic acid sequence, specific primer sequences can be designed In one embodiment of the present invention, the primer is about, but not limited to 5 to 50 oligonucleotides long, or about 10 to 40 oligonucleotides long or more about 10 to 30 oligonucleotides long. Suitable primer sequences can be readily synthesized by one skilled in the art or are readily available from third party providers such as BRL (New England Biolabs™), etc. Other reagents, such as DNA polymerases and nucleotides, that are necessary for a nucleic acid sequence amplification such as PCR are also commercially available.

Separation Methods: Following amplification, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

Identification Methods: Amplification products must be visualized in order to confirm amplification of the desired sequences. One typical visualization method involves staining of a gel with ethidium bromide and visualization under UV light. Alternatively, if the amplification products are integrally labeled with radio- or fluorometrically-labeled nucleotides, the amplification products may then be exposed to x-ray film or visualized under the appropriate stimulating spectra, following separation.

In one embodiment, visualization is achieved indirectly. Following separation of amplification products, a labeled, nucleic acid probe is brought into contact with the amplified marker sequence. The probe preferably is conjugated to a chromophore but may be radiolabeled. In another embodiment, the probe is conjugated to a binding partner, such as an antibody or biotin, where the other member of the binding pair carries a detectable moiety.

In one embodiment, detection is by Southern blotting and hybridization with a labeled probe. The techniques involved in Southern blotting are well known to those of skill in the art and may be found in many standard books on molecular protocols. See Sambrook et al., 1989. Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

In general, prokaryotes used for cloning DNA sequences in constructing the vectors useful in the invention include for example, any gram negative bacteria such as *E. coli, E. coli* strain K12 and *bifidobacteria* and *staphylococcus* Other microbial strains which may be used include *P. aeruginosa* strain PAO1, and *E. coli* B strain and *bifidobacteria*. These examples are illustrative rather than limiting. In particular embodiments steps in the construction of vectors may include cloning and propagation in suitable *E. coli* strains or in suitable *bifidobacterium* strains.

In general, plasmid vectors containing promoters and control sequences which are derived from species compatible with the host cell are used with these hosts. The vector ordinarily carries a replication site as well as one or more marker sequences which are capable of providing phenotypic selection in transformed cells. For example, a PBBR1 replicon region which is useful in many Gram negative bacterial strains or any other replicon region that is of use in a broad range of Gram negative host bacteria can be used in the present invention.

The term "recombinant polypeptide", "recombinant protein: or "fusion protein" or "hybrid protein" or like terms is used herein to refer to polypeptides that have been artificially designed and which comprise at least two polypeptide sequences that are not found as contiguous polypeptide sequences in their initial natural environment, or to refer to polypeptides which have been expressed from a recombinant polynucleotide. In particular embodiments, fusion proteins contain joining sequences to join protein domains that are not normally associated. In broad concept, in embodiments, fusion proteins comprise at least one sequence selected from the group consisting of: a DNA binding domain, a secretion signal sequence, and a trans-activator of transcription that is functional in Eukaryotic cells. In further embodiments fusion proteins comprise a CPP domain and in embodiments the CPP domain comprises a TAT domain. The hybrid proteins comprising signal sequence, transduction domain and DNA binding domain, are also referred to herein as simply "hybrid proteins" or as "NHPs" depending on the context. It will be understood that the different domains comprised in hybrid proteins according to embodiments may be present in any arrangement and any combination and any numbers of copies consistent with their function. Thus in embodiments signal sequences may be internal or may be terminal signal sequences and there may be multiple copies of one or more of each of the domains. In embodiments vectors may comprise one, two, three, four or more DNA sequences suitable for binding by the one or more DNA binding domains comprised in a hybrid protein according to embodiments.

In embodiments vectors comprise a prokaryotic expression cassette for expressing an NHP in the gram positive bacterium and a eukaryotic expression cassette for expressing a candidate gene or sequence in a eukaryotic cell. It will be understood that in alternative embodiments the prokaryotic expression cassette will contain other proteins desired to be expressed in the target gram positive bacterium, instead of one of the hybrid proteins disclosed herein. Thus in embodiments, vectors may be used to express a sequence or gene of interest in a prokaryotic cell.

In this disclosure the terms SHT, SZT, SLT, SMT are acronyms indicating currently preferred forms of the NHP. In the foregoing acronym descriptors Z indicates the presence of at least one Zinc finger DNA binding domain an example of the DNA sequence coding for which is presented as SEQ ID NO: 6 and the amino acid sequence as SEQ ID NO: 46, H means the presence of at least one HU DNA binding domain an example of the DNA sequence coding for which is presented as SEQ ID NO: 44 and the amino acid sequence at SEQ ID NO: 44, T means a CPP or protein transduction domain examples of which are presented as SEQ ID NOs 11 through 17. S means a suitable signal sequence examples of which are presented as SEQ ID NOs 18 through 23. M means the presence of at least one Mer R DNA binding domain an example of the DNA sequence coding for which is presented as SEQ ID NO: 5 and the protein sequence of which is presented at SEQ ID NO: 45. L represents a Lac-I DNA binding domain which is presented herein as SEQ ID NO: 47, it being understood that the inventors have found that hybrid proteins comprising the Lac-I DNA binding domain are not effective for the purposes hereof and are not embodiments of the subject matter claimed herein.

In embodiments presented the signal sequence is an alpha-L-arabinosidase signal sequence SEQ ID NOs 22, 23 but in alternative embodiments is the alpha amylase signal sequence SEQ ID NOs 18, 19 or a truncated version thereof SEQ. ID NOS. 20, 21, are non-limiting alternatives. In embodiments the transduction domain T is Tat SEQ ID NO: 11, but a number of non-limiting possible alternatives are presented herein. Sequences of exemplary SHT, SMT, SZT hybrid proteins are presented as SEQ ID NOs 24, 26 and 27.

It will be understood that variant signal domains, CPP domains and DNA binding domains may be comprised in the hybrid proteins. Thus by way of example and not limitation, the S or signal sequence domain may be any suitable signal sequence, non-limiting examples being the alpha arabinosidase signal sequence, the alpha amylase signal sequence, and truncated versions of these and other signal sequences. The foregoing sequences, or their corresponding DNA sequence, are presented as SEQ ID NOs 18 through 23.

Possible CPP domains (identified as "T" in the abbreviations for the hybrid proteins according to embodiments) include Tat, Antp. Rev, VP22, PbetaMPG (gp41-SV40), Transportan (galanan mastoparan) and Pep1 (TRP rich motif SV40), or the biologically effective portions thereof. Amino acid sequences of the foregoing are presented as SEQ ID NOs 11-17.

It will be understood that in embodiments the foregoing hybrid protein constructions will be comprised in the prokaryotic gene expression cassette of the vector and the foregoing prokaryotic expression cassette will be designed to be functional in a desired bacterial strain. In particular embodiments such strain is a gram positive bacterium and in embodiments is *bifidobacterium*. In embodiments it will be *staphylococcus*. It will likewise be understood that in embodiments the desired DNA for transformation into a target cell comprises a mammalian gene expression cassette for expression of a candidate sequence in the target cell. In embodiments the mammalian cell is a human cell.

The term "expression cassette" is used herein to describe a DNA sequence context comprising one or more locations into which a selected sequence may be inserted so as to be expressible as RNA. In general an expression cassette will comprise a promoter, transcription start site, transcription termination site. A sequence inserted at an appropriate location, between the transcription start and termination sites, will then be expressed when the cassette is introduced into a suitable host cell. In embodiments the choices of flanking sequences will be chosen to function in a chosen cell. Those skilled in the art will thus insert suitable sequences to be expressed in appropriate expression cassettes so that sequences desired to be expressed in a prokaryotic cell will be in a suitable sequence context and those desired to be expressed in eukaryotic cells will likewise be in a suitable sequence context. Those skilled in the art will readily adjust the sequences, structure and other aspects of the cassette to suit particular purposes or to function in particular bacterial strains. In one series of embodiments the coding sequences for a hybrid protein according to embodiments is bounded by a HU promoter and transcription initiation site and a HU transcription termination site. In another embodiment (pFRG1.5, FIG. 1, SEQ ID NO: 2) the promoter is a ribosomal RNA promoter found in *bifidobacteria*, and the terminator is a ribosomal RNA terminator found in *bifidobacteria*. In embodiments the eukaryotic expression cassette comprises a suitable Kozak sequence.

In this disclosure the term "secretion signal", "secretion sequence", "secretion signal sequence", "signal sequence" and the like, refer to a protein motif that is effective to cause secretion of the protein across a cell membrane. In embodiments a secretion sequence is, or is derived from the alpha-L-arabinosidase signal sequence or is an alpha-amylase signal sequence or is a truncated alpha amylase signal sequence. Protein sequences for the foregoing are presented as SEQ ID NOs 23, 19 and 21 respectively and the encoding DNA sequences are presented as SEQ ID NOs 22, 18 and 20 respectively. Those skilled in the art will readily identify and implement suitable signal sequences which are useable in alternative embodiments. One listing of possible signal sequences is to be found in the signal sequence database at <www.signalpeptide.de> and in other resources such as SPdb—Signal Peptide Resource at <http://proline.bic.nus.edu.sg>.

While thousands of suitable signal sequences will be identified by those skilled in the art, using available databases, screening methodologies and well known techniques, non-limiting examples of sources for suitable signal sequences for use in alternative embodiments can optionally be derived from a range of secreted enzymes and other proteins, examples including carbohydrases such as amylases, sucrases, galactosidases, monoshaccharide transferrases, lipases, phospholipases, reductases, oxidases, peptidases, transferases, methylases, ethylases, cellulases, ligninases, secreted signalling proteins, toxins and all manner of other secreted proteins.

Construction of suitable vectors containing the desired coding and control sequences can be achieved employing standard ligation techniques. Isolated plasmids or DNA fragments are cleaved, tailored, and religated in the form desired to form the plasmids required. In embodiments the vectors are synthesized de novo using suitable nucleic acid synthesis procedures as explained elsewhere herein. A range of alternative promoters, polyadenylation signals, DNA binding domains, cell penetrating peptide domains, signal sequences and the like will be readily identified by those skilled in the art using conventional methods and resources.

For analysis to confirm correct sequences in plasmids constructed, the ligation mixtures may be used to transform a bacteria strain such as *E. coli* K12 and successful transformants selected by antibiotic resistance using suitable selection markers and in embodiments the selection markers are antibiotics such as tetracycline, ampicillin spectinomycin, penicillin, kanamycin, gentamycin, zeomycin, methicillin, hygromycin B and others, all of which will be immediately recognized and used by those skilled in the art. Plasmids from the transformants are prepared, analyzed by restriction and/or sequenced. In alternative embodiments bacteria may be selected using suitable auxotrophic selection markers, non-limiting examples of which include the LEU2 and URA3 selection markers whose nature and use are well understood by those skilled in the art. In particular embodiments the selection marker confers resistance antibiotics effective against both gram positive and gram negative bacteria and in embodiments this is spectinomycin, tetracycline or chloramphenicol or erythromycin. In alternative embodiments the vector comprises multiple selection markers to permit selection using different antibiotics in gram positive and gram negative bacteria.

Host cells can be transformed with nucleic acid vectors of this invention and cultured in conventional nutrient media modified as is appropriate for inducing promoters, selecting transformants or amplifying genes. The culture conditions, such as temperature, pH and the like, will be apparent to the ordinarily skilled artisan.

"Transformation" refers to the taking up of vector or of a desired DNA sequence by a host cell whether or not any coding sequences are in fact expressed. Numerous methods are known to the ordinarily skilled artisan, for example, Ca salts and electroporation. Successful transformation is generally recognized when any indication of the operation of the vector or stable propagation of the introduced DNA occurs within the host cell.

It will be understood that the vectors and hybrid proteins disclosed herein are of particular value where standard or commonly used transformation procedures are not reliable.

As used interchangeably herein, the terms "nucleic acid molecule(s)", "oligonucleotide(s)", and "polynucleotide(s)" and "nucleic acids" and the like include RNA or DNA (either single or double stranded, coding, complementary or antisense), or RNA/DNA hybrid sequences of more than one nucleotide in either single chain or duplex form (although each of the above species may be particularly specified), as is consistent or necessary in context. The term "nucleotide" is used herein as an adjective to describe molecules comprising RNA, DNA, or RNA/DNA hybrid sequences of any length in single-stranded or duplex form. More precisely, the expression "nucleotide sequence" encompasses the nucleic material itself and is thus not restricted to the sequence information (i.e. the succession of letters chosen among the four base letters) that biochemically characterizes a specific DNA or RNA molecule. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide.

The term "upstream" is used herein to refer to a location which is toward the 5' end of the polynucleotide from a specific reference point.

The terms "base paired" and "Watson & Crick base paired" are used interchangeably herein to refer to nucleotides which can be hydrogen bonded to one another by virtue of their sequence identities in a manner like that found in double-helical DNA with thymine or uracil residues linked to adenine residues by two hydrogen bonds and cytosine and guanine residues linked by three hydrogen bonds (See Stryer, 1995, which disclosure is hereby incorporated by reference in its entirety).

The terms "complementary" or "complement thereof" are used herein to refer to the sequences of polynucleotides which is capable of forming Watson & Crick base pairing with another specified polynucleotide throughout the entirety of the complementary region. For the purpose of the present invention, a first polynucleotide is deemed to be complementary to a second polynucleotide when each base in the first polynucleotide is paired with its complementary base. Complementary bases are, generally, A and T (or A and U), or C and G. "Complement" is used herein as a synonym from "complementary polynucleotide", "complementary nucleic acid" and "complementary nucleotide sequence". These terms are applied to pairs of polynucleotides based solely upon their sequences and not any particular set of conditions under which the two polynucleotides would actually bind. Unless otherwise stated, all complementary polynucleotides are fully complementary on the whole length of the considered polynucleotide.

Digestion of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg is of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Recovery or isolation of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally (Lawn, R. et al., Nucleic Acids Res. 9: 6103 6114 [1981], and Goeddel, D. et al., Nucleic Acids Res. 8: 4057 [1980]).

Dephosphorylation refers to the removal of the terminal 5' phosphates by treatment with bacterial alkaline phosphatase (BAP). This procedure prevents the two restriction cleaved ends of a DNA fragment from "circularizing" or forming a closed loop that would impede insertion of another DNA fragment at the restriction site. Procedures and reagents for dephosphorylation are conventional (Maniatis, T. et al., Molecular Cloning, 133 134 Cold Spring Harbor, [1982]). Reactions using BAP are carried out in 50 mM Tris at 68° C. to suppress the activity of any exonucleases which may be present in the enzyme preparations. Reactions are run for 1 hour. Following the reaction the DNA fragment is gel purified.

Ligation refers to the process of forming phosphodiester bonds between two double stranded nucleic acid fragments (Maniatis, T. et al., Id. at 146). Unless otherwise provided, ligation may be accomplished using known buffers and conditions with 10 units of T4 DNA ligase ("ligase") per 0.5 µg of approximately equimolar amounts of the DNA fragments to be ligated.

Filling or blunting refers to the procedures by which the single stranded end in the cohesive terminus of a restriction enzyme-cleaved nucleic acid is converted to a double strand. This eliminates the cohesive terminus and forms a blunt end. This process is a versatile tool for converting a restriction cut end that may be cohesive with the ends created by only one or a few other restriction enzymes into a terminus compatible with any blunt-cutting restriction endonuclease or other filled cohesive terminus. In one embodiment, blunting is accomplished by incubating around 2 to 20 µg of the target DNA in 10 mM $MgCl_2$, 1 mM dithiothreitol, 50 mM NaCl, 10 mM Tris (pH 7.5) buffer at about 37° C. in the presence of 8 units of the Klenow fragment of DNA polymerase I and 250 µM of each of the four deoxynucleoside triphosphates. The incubation generally is terminated after 30 min. phenol and chloroform extraction and ethanol precipitation.

The terms "polypeptide" and "protein", used interchangeably herein, refer to a polymer of amino acids without regard to the length of the polymer; thus, peptides, oligopeptides, and proteins are included within the definition of polypeptide. This term also does not specify or exclude chemical or post-expression modifications of the polypeptides of the invention, although chemical or post-expression modifications of these polypeptides may be included excluded as specific embodiments. Therefore, for example, modifications to polypeptides that include the covalent attachment of glycosyl groups, acetyl groups, phosphate groups, lipid groups and the like are expressly encompassed by the term polypeptide. Further, polypeptides with these modifications may be specified as individual species to be included or excluded from the present invention. The natural or other chemical modifications, such as those listed in examples above can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance Creighton (1993); Seifter et al., (1990); Rattan et al., (1992)). Also included within the definition are polypeptides which contain one or more analogs of an amino acid (including, for example, non-naturally occurring amino acids, amino acids which only occur naturally in an unrelated biological system, modified amino acids from mammalian systems, etc.), polypeptides with substituted linkages, as well as other modifications known in the art, both naturally occurring and non-naturally occurring.

As used herein, the term "operably linked" refers to a linkage of polynucleotide elements in a functional relationship. A sequence which is "operably linked" to a regulatory sequence such as a promoter means that said regulatory element is in the correct location and orientation in relation to the nucleic acid to control RNA polymerase initiation and expression of the nucleic acid of interest. For instance, a promoter or enhancer is operably linked to a coding sequence if it affects the transcription of the coding sequence.

In this disclosure the term "shuttle vector" means a DNA vector which is able to replicate in both gram positive and gram negative bacteria and comprises a eukaryotic expression cassette suitable to express a sequence or gene of interest when introduced to a eukaryotic cell and a prokaryotic expression cassette able to express a gene of interest in a eukaryotic cell. In embodiments a first and second strains of host bacteria are from different genera, in embodiments they are from different species, and in embodiments they are from different subspecies. In embodiments the gram negative bacteria is an *E. coli* and in embodiments the gram positive bacteria is *lactococcus, lactobacillus, bifidobacterium,* or *staphylococcus*. It will be understood that a wide variety of combinations of first and second strains of host bacteria are possible in alternative embodiments and the foregoing exemplary combination of *E. coli* with other strains is in no way limiting. In embodiments shuttle vectors are plasmids. Thus the nucleic acid vectors disclosed herein are shuttle vectors able to replicate in both gram positive and gram negative bacteria of suitable types.

A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene. The particular promoter employed to control the expression of a nucleic acid sequence of interest is not believed to be important, so long as it is capable of directing the expression of the nucleic acid in the targeted cell.

In embodiments the target eukaryotic cell is a mammalian cell. In embodiments the mammalian cell is a human cell and in embodiments is a cancer cell. In embodiments the cancer cell is a lung cancer cell, a colon (colorectal) cancer cell, a kidney cancer cell, or an ovarian cancer cell. In particular embodiments the cell is HEK-29 (human embryonic kidney); HT29, CaCo2 (both human adenocarcinoma); HeLa, LL2 (lung carcinoma). In embodiments the cells are cultured cells.

Where a cDNA insert is employed, typically one will typically include a polyadenylation signal to effect proper polyadenylation of the gene transcript. The nature of the polyadenylation signal is not believed to be crucial to the successful practice of the invention, and any such sequence may be employed. Also contemplated as an element of the expression construct is a terminator. These elements can serve to enhance message levels and to minimize read through from the construct into other sequences.

Kits: In some embodiments, there are disclosed kits comprising the vectors disclosed herein. In embodiments the kits comprise a quantity of vector DNA. Embodiments of exemplary nucleic acid vectors and their sequences are presented as FIGS. 1 and 2 and SEQ ID NOs 1 and 2. In embodiments kits comprise a quantity of NHP. In embodiments the kits comprise instructions.

The container means of the kits will generally include at least one vial, test tube, flask, bottle, syringe or other container means, into which the vector, cells and/or primers may be placed, and preferably, suitably aliquoted. Where an additional component is provided, the kit will also generally contain additional containers into which this component may be placed. The kits of the present invention will also typically include a means for containing the probes, primers, and any other reagent containers in close confinement for commercial sale. In embodiments a kit will include injection or blow-molded plastic containers into which the desired vials are retained and in embodiments a kit will include instructions regarding the use of the materials comprised in the kit.

In this disclosure "gene of interest", "sequence of interest", "candidate gene" or "cargo gene" and like terms, refer to a sequence or gene that it is desired to transform into a target cell or that it is desired to express in a target cell. In embodiments hereof such sequences and genes are incorporated into vectors capable of expression of such sequence in particular target cells.

In this disclosure the term "target cell" means a cell into which it is desired to introduce a candidate or cargo gene or sequence. In embodiments a target cell is a eukaryotic cell and in embodiments is a mammalian cell. In embodiments a target cell is a prokaryotic cell.

In embodiments, vectors contain sequences necessary for efficient transcription and translation of specific genes or sequences encoding specific mRNA or siRNA sequences, in a target probiotic cell and may thus comprise transcription initiation and termination sites, enhancers and the like. Similarly any expressed RNA may comprise suitable translation start sites, ribosome binding sites, and the like. All of which will be readily identified by those skilled in the art.

More generally the term "expression cassette" is used herein to describe a DNA sequence context comprising one or more locations into which a selected sequence may be inserted so as to be expressible when present in a suitable cell type. In general an expression cassette will comprise a promoter, transcription start site, transcription termination site and other necessary or desirable sequences. In embodiments the expression cassette comprises a multiple cloning site suitable to permit the convenient insertion thereinto of a DNA sequence having compatible ends, and is able to be expressed as a translatable RNA by suitable cell types. In embodiments, rather than having a multiple cloning site, each expression cassette has restriction cut sites flaking 5' and 3' ends of promoter, gene of interest and terminator. It will be understood that in order for a protein to be expressed the insertion of the DNA sequence must be in the correct reading frame. A sequence inserted at an appropriate location, between the transcription start and termination sites, will then be expressed when the cassette is introduced into a suitable host cell and in embodiments such host cell is bifidobacterial cell. It will be understood that where a chosen nucleotide sequence is said to be inserted into an expression cassette, or where it is said that an expression cassette comprises or includes a chosen nucleotide sequence, then such chosen nucleotide sequence will be inserted into such expression cassette in a form suitable for transcription and/or translation to generate a biologically active form of any protein or oligopeptide encoded thereby or will be expressible in the form of a suitable RNA species. Those skilled in the art will readily adjust the sequences, structure and other aspects of the cassette to suit particular purposes or to function in particular bacterial strains.

For clarity, this disclosure refers to both first and second expression cassettes non-limiting examples of which are presented as SEQ ID NOs 48, 49. In embodiments the first expression cassette is a prokaryotic expression cassette a non-limiting example being presented as SEQ ID NO: 48 and serves to express a desired fusion protein according to embodiments and the second expression cassette is a eukaryotic expression cassette and in embodiments serves to express a candidate DNA in a target cell. Thus in embodiments fusion proteins are encoded by a prokaryotic gene expression cassette and a cargo gene or sequence of interest is comprised in a eukaryotic or mammalian gene expression cassette.

In embodiments the construction of suitable vectors containing the desired coding and control sequences is achieved using standard ligation techniques. Isolated plasmids or DNA fragments are cleaved, tailored, and religated in the form desired to form the plasmids required. In alternative embodiments vectors, inserts, plasmids and any other nucleic acid sequences of interest, are synthesized de novo using standard nucleic acid synthesis techniques. In series of embodiments plasmids were synthesized in silico by GeneArt®, Life Technologies™, (Gene Art/Life Technologies™, Im Gewerbepark B35, Regensburg, 93059 Germany). Examples of other commercial nucleic acid synthesis providers are: DNA2.0 1140 O'Brian Drive Suite A, Menlo Park Calif., 94025 whose website is to be found at www.dna20.com; and Genewiz, 115 Corporate Boulevard, South Plainfield, N.J. 07080 with a website at www.genewiz.com.

Without limitation, the direct synthesis of desired sequences of nucleic acids and amino acids will be readily achieved by those skilled in the art using a range of known techniques. Exemplary references describing relevant synthetic methods are described in the following publications, the content of which is incorporated herein in its entirety to the full extent permissible by law: Khorana H G, Agarwal K L, Büchi H et al. (December 1972). "Studies on polynucleotides. 103. Total synthesis of the structural gene for an alanine transfer ribonucleic acid from yeast". *J. Mol. Biol.* 72 (2): 209-217; Itakura K, Hirose T, Crea R et al. (December 1977). "Expression in *Escherichia coli* of a chemically synthesized gene for the hormone somatostatin". *Science* 198 (4321): 1056-1063; Edge M D, Green A R, Heathcliffe G R et al. (August 1981). "Total synthesis of a human leukocyte interferon gene". *Nature* 292 (5825): 756-62; "Difficult to Express Proteins". *Sixth Annual PEGS Summit.* Cambridge Healthtech Institute. 2010; Liszewski, Kathy (1 May 2010). "New Tools Facilitate Protein Expression". *Genetic Engineering & Biotechnology News.* Bioprocessing 30 (9) (Mary Ann Liebert). pp. 1, 40-41; Welch M, Govindarajan M, Ness J E, Villalobos A, Gurney A, Minshull J, Gustafsson C (2009). Kudla, Grzegorz, ed. "Design Parameters to Control Synthetic Gene Expression in *Escherichia coli*". *PLoS ONE* 4 (9): e7002; "Protein Expression". DNA2.0. Retrieved 11 May 2010; Fuhrmann M, Oertel W, Hegemann P (August 1999). "A synthetic gene coding for the green fluorescent protein (GFP) is a versatile reporter in *Chlamydomonas reinhardtii*". *Plant J.* 19 (3): 353-61; Mandecki W, Bolling T J (August 1988). "FokI method of gene synthesis". *Gene* 68(1): 101-7; Stemmer W P, Crameri A, Ha K D, Brennan T M, Heyneker H L (October 1995). "Single-step assembly of a gene and entire plasmid from large numbers of oligodeoxyribonucleotides". *Gene* 164 (1): 49-53; Gao X, Yo P, Keith A, Ragan T J, Harris T K (November 2003). "Thermodynamically balanced inside-out (TBIO) PCR-based gene synthesis: a novel method of primer design for high-fidelity assembly of longer gene sequences". *Nucleic Acids Res.* 31(22): e143; Young L, Dong Q (2004). "Two-step total gene synthesis method". *Nucleic Acids Res.* 32 (7): e59; Hillson N H, Rosengarten R D, Keasling J D (2012). "j5 DNA Assembly Design Automation Software". *ACS Synthetic Biology* 1 (1): 14-21; Hoover D M, Lubkowski J (May 2002). "DNAWorks: an automated method for designing oligonucleotides for PCR-based gene synthesis". *Nucleic Acids Res.* 30(10): e43; Villalobos A, Ness J E, Gustafsson C, Minshull J, Govindarajan S (2006). "Gene Designer: a synthetic biology tool for constructing artificial DNA segments". *BMC Bioinformatics* 7: 285; Tian J, Gong H, Sheng N et al. (December 2004). "Accurate multiplex gene synthesis from programmable DNA microchips". *Nature* 432 (7020): 1050-4.

Similarly those skilled in the art will immediately recognise and use a range of suitable software applications and online resources for the prediction and design of desired nucleotide and protein sequences including hybrid sequences, plasmid and other vector sequences, coding and other sequences.

By way of example and not limitation, a variety of online DNA databases referred to elsewhere herein contain sequences of a variety of signal peptides, DNA binding domains and their recognition sequences, selection markers, resistance genes, auxotrophic mutants, promoters, and origins of replication. Thus for example:

One listing of possible signal sequences is to be found in the signal sequence database at <http://www.signalpeptide.de/index.php?m=listspdbat> and further information is to be found at the main web site at http://www.signalpeptide.de/.

Possible transduction sequences are described herein and these and other similar sequences will be readily identified using online resources.

A range of sequence analysis and manipulation software is readily available and used by those skilled in the art. By way of example and not limitation, suitable software for the manipulation and analysis of nucleotide and/or protein sequences includes SNAPGENE, pDRAW32, DNASTAR, BLAST, CS-BLAST, FASTA, MB-DNA Analysis software, DNADynamo, Plasma DNA, Sequencher; suitable motif prediction and analysis software includes but is not limited to FMM, PMS, eMOTIF, PHI-Blast, Phyloscan, and an exemplary library of protein motifs is 1-Sites. Links to all of the foregoing are to be found on the Wikipedia web page at http://en.wikipedia.org/wiki/List_of_sequence_alignment_software which was accessed on Jan. 19, 2015.

More generally extensive databases comprising DNA, RNA, and protein sequences include but are not limited to GenBank, RefSeq, TPA, PDB and the NCBI database at http://www.ncbi.nlm.nih.gov. These and other suitable tools and resources will be readily identified and used by those skilled in the art.

DESCRIPTION OF EMBODIMENTS

Embodiments of the invention are hereafter described with general reference to FIGS. 1 through 10 and SEQ ID NOs 1 through 49 all of which form a part of and are incorporated in this disclosure.

First Embodiment

In a first general aspect of the embodiment there is disclosed a nucleic acid vector comprising: a first origin of replication for replication in gram-positive bacteria and second origin of replication for replication in gram-negative bacteria, at least one selection markers for selection in both gram-positive and gram-negative bacteria; a first gene expression cassette functional in gram positive bacteria and a second gene expression cassette functional in a mammalian cell an in embodiments this is a human cell.

In embodiments the vector comprises a single selection marker effective in both gram positive and gram negative bacteria.

A first illustrative embodiment of a vector according to the first embodiment is shown in FIG. 1 and the corresponding vector sequence is presented as SEQ ID NO: 1. The design of suitable expression cassettes will be readily understood by one skilled in the art. In the embodiment pBRA2.0 SHT the first expression cassette for expression in a gram positive bacterium comprises an HU promoter and terminator flanking the NHP encoding sequences as will be seen in FIG. 1. In the embodiment pBRA2.0 SHT the second expression cassette for expression in a eukaryotic cell, which in embodiments is a mammalian cell and in embodiments is a human cell, comprises the CMV (cytomegalovirus) promoter, a KOZAK sequence and a Thymidine Kinase polyadenylation/termination sequence, the foregoing flanking an insertion sequence for the insertion of a cargo sequence. This will be seen in SEQ ID NO: 1 wherein a GFP protein is inserted into the second expression cassette.

In particular variants of the first embodiment, a first origin of replication is functional in *E. coli* and second origin of replication is functional in at least one of *Staphylococcus* and *Bifidobacteria*. In further variants a single bifunctional origin of replication is functional in *E. coli* and in at least one of *Staphylococcus* and *Bifidobacteria*.

In the embodiment pBRA2.0 SHT the vector comprises a pUC origin of replication for replication in *E. coli* and a pB44 origin of replication for replication in *Bifidobacterium*.

It will be understood that suitable origins of replication for use in a gram negative *bacterium*, namely *E. coli*, include the pUC origin of replication presented as SEQ ID NO: 29 and a wide range of other gram negative origins, which will be readily identified and adopted by those skilled in the art.

Suitable origins of replication for *Bifidobacterium* and other gram positive strains of bacteria include PB44 ORI presented as SEQ ID NO: 30, and the pDOJHR ORI presented as SEQ ID NO: 28, within which the origin is comprised.

DNA-BS denotes a nucleotide binding site (SEQ. ID. NO. 43) for a Zinc finger DNA binding protein (SEQ ID NO: 46).

It will therefore be understood that in alternative embodiments the first gram negative origin of replication will comprise a sequence having at least 90, 91, 92, 93, 94, 95, 96, 97, 98, 99 or 100% sequence identity over at least 20, 40, 60, 80 or more contiguous nucleotides to the pUC (*E. coli*) ORI presented as SEQ ID NO: 29.

It will likewise be understood that in alternative embodiments the second or gram positive origin of replication will comprise a sequence having at least 90, 91, 92, 93, 94, 95, 96, 97, 98, 99 or 100% sequence identity over at 20, 40, 60, 80 or more contiguous nucleotides to the pB44 or pDOJHR origins of replication whose sequences are presented as SEQ ID NOs 30 and 28 respectively.

In embodiments the selection marker is effective in both gram positive and gram negative bacteria. In embodiments the selection marker is resistance to spectinomycin. In embodiments the selection marker comprised in the vector is resistance to tetracycline. In embodiments the selection marker comprised in the vector is resistance to chloramphenicol.

In alternative embodiments the vector comprises separate selection markers for gram positive and gram negative bacteria. Accordingly, in embodiments the vector comprises a selection marker or a combination of selection markers selected from resistance to ampicillin, penicillin, tetracycline, chloramphenicol, streptomycin, quinolone, fluoroquinolone, gentamycin, neomycin, kanamycin, spectinomycin. Those skilled in the art will readily identify additional selection markers and the gene sequences responsible therefore. Listings of possible selection markers that can be adopted in variant embodiments are to be found in Stryer, Sambrook et al. 1989, Maniatis the contents of which are all incorporated herein by reference to wherever permissible by law.

In the illustrated embodiments the first or gram negative origin of replication is functional in *E. coli*. In the illustrated embodiments the second or gram positive origin of replication is functional in at least one of *bifidobacterium* and *staphylococcus*. In alternative embodiments the origin is functional in a bacterium selected from the group consisting of *bifidobacteria, lactococcus,* and *clostridium, staphylococcus* and *streptococcus*.

In the first embodiment the first gene expression cassette encodes a hybrid protein comprising at least one DNA binding domain, at least one cell penetrating peptide (CPP) domain, and at least one secretion signal sequence. Alternative embodiments of the NHP are possible and examples are disclosed below.

In embodiments the nucleic acid vectors according to embodiments further comprise at least one DNA motif that binds to the at least one DNA binding domain of said hybrid protein. It will be understood that in embodiments the said DNA binding domain is sequence specific and that in other embodiments, such as embodiments wherein the NHP comprises an HU domain, the binding is not sequence specific and in such embodiments the vector does need not comprise a complementary binding motif.

Second Embodiment

Figure 2:
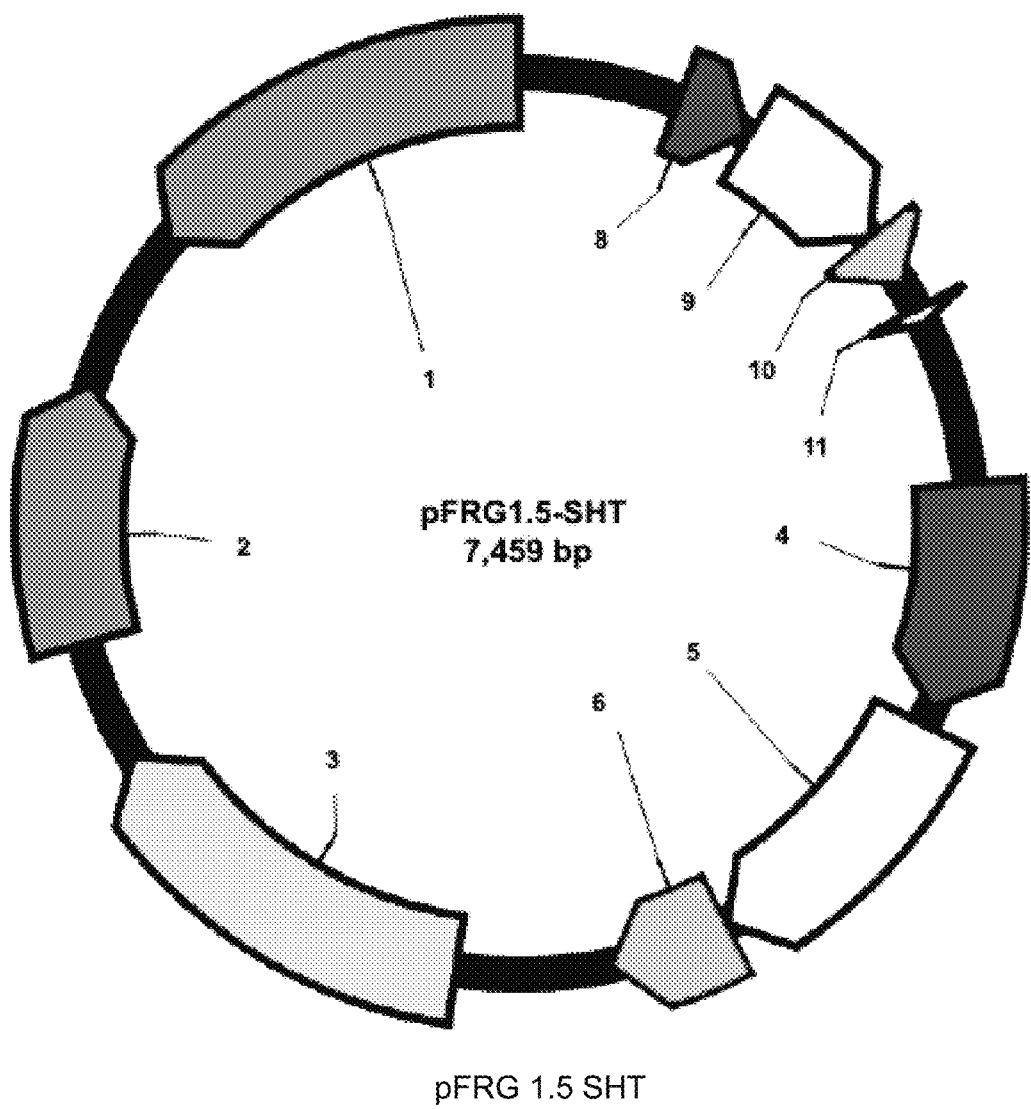
FIG. 2. shows the structure of a vector according to a second embodiment of the present subject matter and identified as pFRG1.5-SHT.

A second illustrative embodiment of a plasmid according to the subject matter hereof is presented in FIG. 2 and a sequence for an embodiment of the vector is presented as SEQ ID NO: 2. This second embodiment is designated pFR1,5 SHT, reflecting the identity of the inserted hybrid protein.

The vector comprises gram-positive origin of replication, namely the PDOJHR origin of replication (2) whose sequence is comprised within SEQ ID NO: 28 and a gram negative origin of replication, namely the pUC ORI (1) presented as SEQ ID NO: 29. The vector comprises prokaryotic and eukaryotic expression cassettes. The prokaryotic expression cassette comprises a Ribosomal RNA promoter (8) and terminator (10) flanking coding sequences (9) for the hybrid protein SHT, defined elsewhere herein. The mammalian gene expression cassette comprises a CMV promoter (4) and a TK Poly A site and terminator (6). In this case the inserted gene is a GFP reporter sequence (5).

In the example the plasmid comprises DNA sequences (11) suitable for binding to the sequence comprised in the SHT hybrid protein. The selectable marker in this plasmid is a spectinomycin resistance gene (3) but alternative selection markers, including those disclosed herein, will be readily identified and adopted by those skilled in the art. It will be understood that alternative forms of hybrid protein, alternative cargo sequences, and alternative protein binding motifs can readily be incorporated in variants of the illustrated embodiment. Likewise it will be understood that a wide range of well-known gram negative origins of replication will be selected amongst by those skilled in the art.

In a further aspect of the first embodiment there are disclosed hybrid proteins or fusion proteins. The hybrid proteins comprise at least one DNA binding domain, at least one cell penetrating peptide (CPP) domain, and at least one secretion signal sequence.

In embodiments there is disclosed a hybrid protein as described below or as otherwise disclosed herein. In embodiments the hybrid protein comprises: at least one signal sequence; at least one DNA binding domain; and at least one cell penetrating peptide (CPP) domain. It will be understood that in embodiments the protein comprises only one copy of a signal sequence domain, CPP domain and DNA binding domain but that in alternative embodiments any one, two or three of such domains may be present in more than one copy, or may comprise one, two, three or more different domains. Thus in embodiments, by way of example and not limitation, a protein may comprise multiple copies of the same DNA binding domain, or may contain copies of two, three or more different DNA binding domains. Similarly in embodiments the protein may comprise multiple copies of a CPP domain which copies may be the same or may be different. Similarly in embodiments the protein may comprise multiple signal sequences.

In embodiments the at least one CPP domain is or comprises a TAT domain, a VP22 domain, an Antp domain or a Rev domain. In alternative embodiments the CPP domain is or comprises a P-Beta MPG (gp41-SV40) domain, a Transportan (galanin mastoparan) domain, or a Pep-1 (Trp rich motif—SV40) domain. The sequences of such domains are presented herein as SEQ ID NOs 11 through 17.

In embodiments the at least one secretion signal sequence is selected from the group consisting of an alpha amylase signal sequence and an alpha arabinosidase signal sequence, or a truncated form of such signal sequences. The sequences of these exemplary signal sequences and their corresponding DNA sequences are presented as SEQ ID NOs 18-23.

In embodiments the at least one DNA binding domain is or comprises at least one sequence specific DNA binding domain. In embodiments the at least one DNA binding domain comprises at least one domain selected from the group consisting of: a Zinc finger DNA binding domain, a homeobox DNA binding domain, a MerR DNA binding domain, and a HU DNA binding domain. DNA sequences encoding a selected DNA binding domain are presented as SEQ ID NOs 3 through 6.

Sequences of variant hybrid proteins comprising the foregoing domains are presented as SEQ ID NOs 24 through 27 and corresponding DNA sequences are presented as SEQ ID NOs 7 through 10. In embodiments the hybrid protein comprises an alpha arabinosidase signal sequence (SEQ ID NO: 23), a TAT domain (SEQ ID NO: 11) and a HU DNA binding domain (SEQ ID NO: 4).

In a further series of embodiments there is disclosed a method for transforming a target cell with a desired DNA, the method comprising the step of contacting the target cell with a protein-DNA complex comprising the desired DNA and the hybrid protein according to embodiments. In embodiments the method further comprises the step of contacting said DNA with said hybrid protein to form said protein-DNA complex. In embodiments the target cell is a eukaryotic cell and in embodiments is a prokaryotic cell and in embodiments is a gram positive prokaryotic cell.

In embodiments of the method the DNA is a plasmid and in embodiments the plasmid comprises an expression cassette for expressing the hybrid protein in a gram positive bacterium. In embodiments the plasmid comprises a eukaryotic expression cassette and in embodiments the eukaryotic expression cassette comprises inserted thereinto a DNA sequence for expression in a target eukaryotic cell. In embodiments the plasmid is a nucleic acid vector according to other embodiments disclosed herein.

In other embodiments of the method the at least one DNA binding domain is a sequence specific DNA binding domain and the plasmid comprises at least one nucleotide sequence for binding to said at least one sequence specific DNA binding domain. In embodiments of the method the at least one CPP sequence has at least 90% amino acid sequence identity over 10 contiguous amino acids to SEQ ID. NO. 11, 12, 13, 14, 15, 16, or 17 In embodiments of the method said at least one signal sequence has at least 90%, 91%, 92%, 93%, 94%, 95%, 96%, 97%, 98%, 99% or 100% amino acid sequence identity over at least 10, 15, 20 or more contiguous amino acids to SEQ ID NO: 19, 21, or 23.

In embodiments of the method said at least one DNA binding domain has at least 0%, 91%, 92%, 93%, 94%, 95%, 96%, 97%, 98%, 99% or 100% amino acid sequence identity over at least 10, 15, 20 or more contiguous amino acids to the amino acid sequence encoded by SEQ ID NOs 3, 4, 5 or 6.

In embodiments of the method the cell to be transformed is a gram positive bacterium and in embodiments is a eukaryotic cell which in embodiments is a mammalian cell and in embodiments is a human cell.

In related embodiments there is disclosed a cell transformed with an exogenous DNA using the hybrid protein according to embodiments wherein the cell is a gram positive bacterium or is a mammalian cell. In embodiments there is also disclosed the use of the hybrid protein according to embodiments hereof, to transform a gram positive bacterium or a mammalian cell. In embodiments the cell is a human cell. Examples of cells transformed using embodiments are disclosed elsewhere herein.

In embodiments the cell to be transformed using the hybrid protein is a *Staphylococcus, streptococcus, Bifidobacterium, lactococcus, lactobacillus, clostridium* or any other bacterial type disclosed herein. In embodiments the cell to be transformed is a mammalian cell and in embodiments is a *bifidobacterium* or a *staphylococcus*.

In embodiments there is disclosed a bacterial cell able to synthesize the hybrid protein according to embodiments. In embodiments the cell comprises a plasmid encoding the hybrid protein in a suitable expression context and in embodiments the cell is a *bifidobacterium*.

In embodiments the hybrid protein is synthsised by a bacterial cell and in alternative embodiments the hybrid protein is synthesized in silico using methods well known in the art and as further indicated herein.

KIT EMBODIMENTS

In a further series of embodiments there are disclosed kits for transforming a target cell with a desired DNA, the kit comprising a quantity of the hybrid protein according to embodiments, and instructions to: form a complex of the said hybrid protein with the desired DNA; and contact the said complex with said target cell.

In embodiments the kits comprise suitable media or buffers and solutions for said contacting or contain recipes or components for said media or buffers.

In embodiments the hybrid protein is encoded by a vector according to embodiments and is synthesized by a suitable host gram positive bacterium using a suitable expression cassette in the vector. In alternative embodiments the NHP is artificially synthesized using solid phase synthesis of peptide according to known techniques. In alternative embodiments the NHP is synthesized by a separate bacterium. In embodiments the purified or enriched NHP is added directly to a solution comprising a vector desired to be transformed into a target prokaryotic or eukaryotic cell, and the mixture containing the DNA/protein complex is contacted with the target cell. In embodiments such contacting of the protein and DNA occurs under suitable conditions for the formation of the complex to occur. While those skilled in the art will readily determine and optimize the conditions for the binding of particular combinations of hybrid protein and DNA using existing resources and the common general knowledge in the art, specific conditions used in non-limiting examples are presented in the Examples section hereof.

In embodiments of the NHP the DNA binding domain is one of a HU DNA binding domain, a Zinc finger DNA binding domain, a homeobox DNA binding domain, a homeobox DNA binding domain and a MerR DNA binding domain, or combinations thereof. Exemplary DNA sequences encoding suitable binding domains are presented as SEQ ID NOs 3, 4, 5, 6. In a range of alternative embodiments of the embodiments presented herein suitable DNA binding domains may be of any general type, including but not limited to helix-turn-helix, Zinc finger, leucine zipper, winged helix, winged helix turn helix, helix loop helix, HMG box, Wor 3 and RNA guided binding domains. Illustrative examples of DNA binding proteins whose DNA binding domains may be utilized in embodiments include histones, histone like proteins, transcription promoters, transcription repressors, transcriptional regulators, which may be drawn from a wide range of alternate sources and operons.

In embodiments the DNA binding domain is a HU DNA binding domain from the bacterial HU DNA binding protein. The sequence of the HU binding domain is presented at SEQ ID NO: 44 and its encoding DNA as SEQ ID NO: 4

In embodiments the CPP comprises a TAT domain (SEQ ID NO: 11), a VP22 protein of Herpes Simplex Virus (SEQ ID NO: 14), or the protein transduction domain of the Antennapedia (Antp) protein (SEQ, ID. NO. 12), or combinations thereof. Those skilled in the art will recognise that additional protein transduction domains can be used in alternative variants of the embodiment. In one series of alternative embodiments the CPP domain comprises a Rev domain. Details of the foregoing and alternative possible transduction domains are described in Sugita et al., "Comparative study on transduction and toxicity of protein transduction domains" Br J Pharmacol. March 2008; 153(6): 1143-1152. FIG. 11 is a table showing the protein sequences of the four foregoing protein transduction domains and is taken from Sugita et al.

In embodiments the secretion signal sequence is alpha-L-arabinosidase (SEQ ID NO: 23), or a full length (SEQ ID NO: 19) or truncated (SEQ ID NO: 21)alpha-amylase signal sequence. The DNA sequences encoding the foregoing are presented as SEQ ID NO: 22, 18 and 20 respectively).

Thus, in embodiments, the NHP comprises an alpha-L-arabinosidase signal sequence (SEQ ID NO: 23), a Zinc finger DNA binding domain (SEQ ID NO: 46), and a TAT domain (SEQ ID NO: 11). Thus, in embodiments, the NHP comprises an alpha-L-arabinosidase signal sequence (SEQ ID NO: 23), a Zinc finger DNA binding domain (SEQ ID NO:46), and a VP22 domain (SEQ ID NO: 14). Thus, in embodiments, the NHP comprises an alpha-L-arabinosidase signal sequence (SEQ ID NO: 23), a Zinc finger DNA binding domain (SEQ ID NO: 46), and the protein transduction domain of the Antp protein (SEQ ID NO:12). Thus, in embodiments, the NHP comprises an alpha-L-arabinosidase signal sequence (SEQ ID NO: 23), a Zinc finger DNA binding domain. (SEQ ID NO: 46), Thus, in embodiments, the NHP comprises an alpha-L-arabinosidase signal sequence (SEQ ID NO: 23), a HU DNA binding domain, (SEQ ID NO: 44), and a TAT domain (SEQ ID NO: 11). Thus, in embodiments, the NHP comprises an alpha-L-arabinosidase signal sequence (SEQ ID NO: 23), a HU DNA binding domain (SEQ ID NO: 44), and a VP22 domain (SEQ ID NO: 14). Thus, in embodiments, the NHP comprises an alpha-L-arabinosidase signal sequence (SEQ ID NO: 23), a HU DNA binding domain (SEQ ID NO: 44), and the protein transduction domain of the Antp protein (SEQ ID NO: 12). Thus, in embodiments, the NHP comprises an alpha-L-arabinosidase signal sequence (SEQ ID NO: 23), a HU DNA binding domain (SEQ ID NO: 44).

A) Variants Based on Alpha-L-Arabinosidase

Thus, in embodiments, the NHP comprises an alpha-L-arabinosidase signal sequence (SEQ ID NO: 23), a Mer R DNA binding domain (SEQ ID NO: 41), and a TAT domain (SEQ ID NO: 11). Thus, in embodiments, the NHP comprises an alpha-L-arabinosidase signal sequence a Mer R DNA binding domain (SEQ ID NO: 41), and a VP22 domain (SEQ ID NO: 14). Thus, in embodiments, the NHP comprises an alpha-L-arabinosidase signal sequence a Mer R DNA binding domain (SEQ ID NO: 41), and the protein transduction domain of the Antp protein (SEQ ID NO: 12). Thus, in embodiments, the NHP comprises an alpha-L-arabinosidase signal sequence, a Mer R DNA binding domain (SEQ ID NO:41).

Thus, in embodiments, the NHP comprises an alpha-L-arabinosidase signal sequence (SEQ ID NO: 23), a HU DNA binding domain (SEQ ID NO: 44), and a TAT domain (SEQ ID NO:11). Thus, in embodiments, the NHP comprises an alpha-L-arabinosidase signal sequence, a HU DNA binding domain (SEQ ID NO: 44), and a VP22 domain (SEQ ID NO: 14). Thus, in embodiments, the NHP comprises an alpha-L-arabinosidase signal sequence, a HU DNA binding domain (SEQ ID NO: 44), and the protein transduction domain of the Antp protein (SEQ ID NO: 12). Thus, in embodiments, the NHP comprises an alpha-L-arabinosidase signal sequence, a HU DNA binding domain (SEQ ID NO: 44).

b) Variants Based on Alpha Amylase Signal Sequence

Thus, in embodiments, the NHP comprises an alpha-amylase signal sequence (SEQ ID NOs 19, 21), a Zinc finger DNA binding domain (SEQ ID NO: 46), and a TAT domain (SEQ ID NO:11). Thus, in embodiments, the NHP comprises an alpha-L-amylase signal sequence (SEQ ID NOs 19, 21), a Zinc finger DNA binding domain (SEQ ID NO: 46), and a VP22 domain (SEQ ID NO: 14). Thus, in embodiments, the NHP comprises an alpha-L-amylase signal sequence (SEQ ID NOs 19, 21), a Zinc finger DNA binding domain (SEQ ID NO: 46), and the protein transduction domain of the Antp protein (SEQ ID NO: 12). Thus, in embodiments, the NHP comprises an alpha-L-amylase signal sequence (SEQ ID NOs 19, 21), a Zinc finger DNA binding domain (SEQ ID NO: 46).

Thus, in embodiments, the NHP comprises an alpha-L-amylase signal sequence (SEQ ID NOs 19, 21), a homeobox DNA binding domain and a TAT domain (SEQ ID NO: 11). Thus, in embodiments, the NHP comprises an alpha-L-amylase signal sequence (SEQ ID NOs, 19, 21), a homeobox DNA binding domainand a VP22 domain (SEQ ID NO: 14). Thus, in embodiments, the NHP comprises an alpha-L-amylase signal sequence (SEQ ID NOs 19, 21), a homeobox DNA binding domain, and the protein transduction domain of the Antp protein (SEQ ID NO: 12). Thus, in embodiments, the NHP comprises an alpha-L-amylase signal sequence (SEQ ID NOs 19, 21), a homeobox DNA binding domain.

Thus, in embodiments, the NHP comprises an alpha-L-amylase signal sequence (SEQ ID NOs 19, 21), a Mer R DNA binding domain (SEQ ID NO: 45), and a TAT domain (SEQ ID NO: 11). Thus, in embodiments, the NHP comprises an alpha-L-amylase signal sequence (SEQ ID NOs 19, 21), a Mer R DNA binding domain (SEQ ID NO: 45), and a VP22 domain (SEQ ID NO:14). Thus, in embodiments, the NHP comprises an alpha-L-amylase signal sequence, a Mer R DNA binding domain (SEQ ID NO: 45), and the protein transduction domain of the Antp protein (SEQ ID NO: 12). Thus, in embodiments, the NHP comprises an alpha-L-amylase signal sequence, a Mer R DNA binding domain (SEQ ID NO: 45). Thus, in embodiments, the NHP comprises an alpha-L-amylase signal sequence (SEQ ID NOs 19, 21), a HU DNA binding domain (SEQ ID NO: 44), and a TAT domain (SEQ ID NO: 11). Thus, in embodiments, the NHP comprises an alpha-L-amylase signal sequence, a HU DNA binding domain (SEQ ID NO: 44), and a VP22 domain (SEQ ID NO: 14). Thus, in embodiments, the NHP comprises an alpha-L-amylase signal sequence (SEQ ID NOs 19, 21), a HU DNA binding domain (SEQ ID NO: 44), and the protein transduction domain of the Antp protein (SEQ ID NO: 12). Thus, in embodiments, the NHP comprises an alpha-L-amylase signal sequence (SEQ ID NOs 19, 21), a HU DNA binding domain (SEQ ID NO: 44), and a CPP domain non limiting examples of which are presented as SEQ ID NOs 11 through 17.

In embodiments each component domains of the NHP is substantially full length. In embodiments each of the component domains of the NHP is a functional but partial domain.

Thus in embodiments there are disclosed the foregoing NHPs, as well as nucleic acid sequences encoding such NHP's and vectors comprising the nucleic acid sequences encoding the NHPs. Further in embodiments the encoding sequences are operatively linked to and transcribable by a host bacterium as part of a eukaryotic expression cassette.

In a series of embodiments of the first embodiment, the nucleic acid vectors comprise a cargo or candidate or exogenous gene or sequence is inserted into the eukaryotic expression cassette of the vector. The cargo gene may be any gene or nucleic acid sequence. In particular examples the gene is a marker gene such as GFP or is a tumor suppressor. It will be understood that the range of possible sequences that may be inserted into the eukaryotic expression cassette is not limited in any way. One skilled in the art will readily understand the adaptation and insertion of suitable sequences for expression in vectors according to this disclosure.

In embodiments the cargo or candidate sequence is a fluorescent or marker protein.

In embodiments the vector comprises at least one DNA motif for binding of a suitable DNA binding domain of a protein or of a hybrid protein according to an embodiment, has at least 90%, 91%, 92%, 93%, 94%, 95%, 96%, 97%, 98%, 99% or 100% sequence identity to SEQ ID NO: 41 or 43 over at least about 10, 15, 20, or more contiguous nucleotides.

In embodiments the selection marker is effective in both gram positive and gram negative bacteria in embodiments the selection marker is resistance to spectinomycin. In embodiments the selection marker comprised in the vector is resistance to tetracycline. In embodiments the selection marker comprised in the vector is resistance to chloramphenicol. In embodiments the selection marker is any antibiotic effective against both gram negative and gram positive bacteria.

Third Embodiment

In a third series of embodiments there are disclosed methods and compositions for transforming cells with DNA and expressing an exogenous or candidate or cargo DNA sequence in a target eukaryotic cell. In embodiments the target cell is a mammalian cell. In embodiments the target cell is a cancer cell. In embodiments the cancer cell is a lung or colon carcinoma cell and in embodiments is HEK-29 (human embryonic kidney); HT29, CACO (both human adenocarcinoma); HeLa, LL2 (lung carcinoma) Thus in one variant of the embodiment there is disclosed a method for transforming a eukaryotic target cell with a candidate DNA sequence, the method comprising the steps of: a) expressing in a first cell the hybrid protein from the first expression cassette of a nucleic acid vector according to the present invention, to form a complex between said hybrid protein and said nucleic acid vector; and b) contacting the target cell with the formed hybrid protein and nucleic acid vector complex, wherein said candidate DNA sequence is comprised in the second expression cassette.

In a further aspect of the embodiment there is disclosed a method for transforming a eukaryotic target cell with a candidate DNA sequence, the method comprising the step of: contacting the eukaryotic target cell with a nucleic acid vector complex formed by binding a vector according to the present invention with a hybrid protein comprising a signal sequence, a CPP sequence and a DNA binding sequence suitable to bind the vector.

In a further aspect of the embodiment there is disclosed a method for transforming a prokaryotic target cell with a candidate DNA sequence, the method comprising the step of: contacting the prokaryotic target cell with a nucleic acid vector complex formed by binding a vector according to the present invention with a hybrid protein comprising a signal sequence, a CPP sequence and a DNA binding sequence suitable to bind the vector. In particular embodiments the hybrid protein-DNA complex is suitable to transform *bifidobacteria*, *E. coli* and *staphylococcus*.

Fourth Series of Embodiments

In alternative embodiments there are disclosed cells containing the nucleic acid vector according to any of the other embodiments. In embodiments the cell is a prokaryote a eukaryote, a mammalian cell, a human cell, a cancer cell, a probiotic bacterium, a gram negative bacterium or a gram positive bacterium. In embodiments the cell is a bacterial cell, or is a gram positive or gram negative cell. In embodiments the cell is a human kidney cell, a human adenocarcinoma cell or a human lung carcinoma cell. In embodiments the cell is an HEK-29 cell (human embryonic kidney); an HT29, CaCo2 cell (both human adenocarcinoma); or an HeLa or LL2 (lung carcinoma) In embodiments a bacterial cell is *E. coli, bifidobacteria, lactococcus*, and *clostridium, staphylococcus* or *streptococcus*.

Fifth Series of Embodiments

In embodiments there are disclosed kits comprising vectors according to embodiments, or NHPs according to embodiments, or a combination of vectors and NHPs according to embodiments.

In embodiments there is disclosed a kit for transforming a cell with the vector according to claim 1, the kit comprising a quantity of the vector and a quantity of the vector and quantity of a hybrid protein comprising a DNA binding domain, a signal sequence domain and a CPP domain. In embodiments the kit further comprises a quantity of the nucleic acid vector.

In use the fusion protein according to an embodiment is used to transform a target prokaryotic cell or a target eukaryotic cell with a desired DNA. In embodiments the desired DNA is a plasmid or other vector. In embodiments the desired DNA comprises an expression cassette suitable to be expressed in the target prokaryotic cell.

In embodiments said at least one recognition nucleotide sequence has at least 90%, 91%, 92%, 93%, 94%, 95%, 96%, 97$, 98%, 99% or more sequence identity to SEQ ID. NO. 41 which is the MerR DNA motif or to SEQ ID NO: 43 which is the Zinc Finger DNA motif.

In embodiments the fusion protein comprises, sequentially: signal sequence—HU DNA binding domain—TAT domain; or signal sequence—Mer R DNA binding domain—TAT domain; or signal sequence—Zn finger DNA binding domain—TAT domain; or signal sequence—zinc finger DNA binding domain—TAT domain. The nucleotide sequences encoding non-limiting examples of hybrid proteins according to embodiments are presented as SEQ ID NOs 7 through 10, and amino acid sequences are presented as SEQ ID NOs 24 through 27.

In embodiments said at least one recognition nucleotide sequence has at least about 99%, 98%, 97%, 96%, 95%, 94%, 93%, 92%, 91% or 90% sequence identity to SEQ ID NO: 41 or 43 over a sequence of at least 10, 15, or 20 contiguous nucleotides.

Example 1

Preparation of NHP

NHP Preparation:

A NHP library was designed and created. This library was used to test hypothesis regarding the DNA binding, transfection and transformation capabilities of NHPs. The library consisted of: H (HU. SEQ ID NO: 44), M (Mer R SEQ ID NO: 45), L (Lac I SEQ ID NO: 47), Z (Zn finger SEQ ID NO: 46), and of combinations of a CPP domain and DNA binding domain HT (Hu—TAT combining SEQ ID NOs 44 and 11 in sequence), TH (Tat HU combining SEQ ID NOs 11 and 44 in sequence), LT (Lac Tat combining SEQ ID NOs 47 and 11 in sequence), TL (Tat—Lac I combining SEQ ID NOs 11 and 47 in sequence), TM (Tat-Mer R combining SEQ ID NOs 11 and 45 in sequence), MT (Mer R—Tat combining SEQ ID NOs 45 and 11 in sequence), TZ (Tat-Zn finger combining SEQ ID NOs 11 and 46 in sequence), ZT (Zn finger Tat combining SEQ ID NOs 46 and 1 in sequence), SHT (arabinosidase signa, Hu, Tat SEQ ID NO: 24), THS (Tat-Hu-arabinosidase signal) and SZT (arabinosidase signal sequence, Zn finger, Tat SEQ ID NO: 27). All proteins were chemically synthesized by solid phase peptide synthesis by LifeTein™ LCC.

The NHP library was used to characterize plasmid DNA binding abilities. It was demonstrated that all NHP's except those comprising a Lac-I DNA binding protein domain bound to plasmid DNA.

Figure 3:
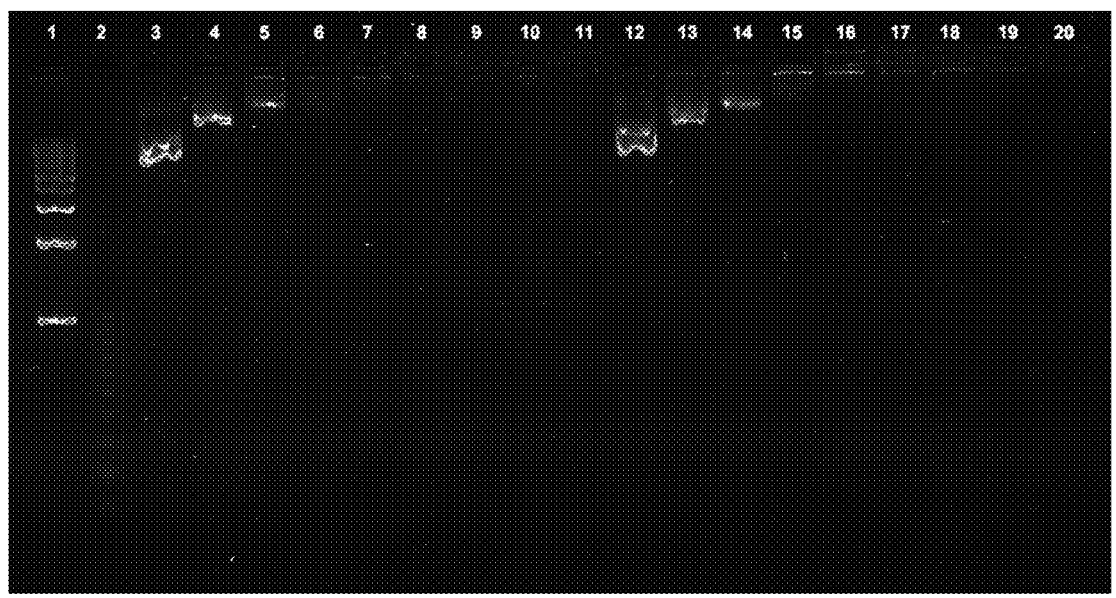
FIG. 3 shows a gel shift assay demonstrating the binding of SHT and SZT hybrid proteins with pBRA2.0 SHT. SHT and SZT interact with pBRA2.0 and result in gel-shift with increasing concentrations of peptide.

The different hybrid proteins display significant differences in binding affinities. FIG. 3 depicts the ability of SHT and SZT (SEQ ID NOs 24 and 27 respectively) to bind to a plasmid DNA (pBRA2.0 FIG. 1 and SEQ ID NO: 1). FIG. 3 shows that as concentrations of SHT (SEQ ID NO: 24) and SZT (SEQ ID NO: 27) increase, plasmid migration on a gel electrophoresis assay are retarded.

The NHP library was used to characterize plasmid DNA transfection into various mammalian cell lines including HEK-293, Hela, CaCo-2, LL2 and HT-29s. Various plasmids encoding the Green Fluorescent Protein (GFP) gene under control of the Cytomegalovirus promoter were bound to NHPs from the library. The NHP-bound plasmids were then incubated with the various cell lines, and examined under fluorescent microscopy to detect GFP expression. As expected, DNA binding domains alone did not result in plasmid transfection; however HT, LT, MT, ZT, SHT (SEQ ID NO: 24) and SZT (SEQ ID NO: 27) did result in plasmid transfection with ZT, SHT and SZT having the best transfection efficiencies. Reverse orientation NHPs such as TL, TZ, TS, TM and THS result in very limited plasmid transfection. This suggests that the TAT domain and DNA binding domains are necessary for plasmid transfection, specifically in the orientation with TAT domain on the amino-terminal. In addition, these findings also suggest that the secretion signal domain S, improves the transfection efficiency. FIG. 10 depicts SHT and SZT mediated transfection of the pBRA2.0 SHT plasmid (SEQ ID NO: 1) in HEK-293 and Hela cell lines. All other cell lines tested demonstrated consistent results.

A portion of the NHP library was used to examine the ability to transform bacteria with plasmid DNA. The NHP library included HT, ZT, TH, TZ, SHT and SZT. NHP-mediated transformation assays were tested on *Bifidobacteria longum, Staphylococcus aureus* and *Escherichia coli*. It was demonstrated that only SHT (SEQ ID NO: 24) and SZT (SEQ ID NO: 27) were able to transform *Bifidobacteria longum*, whereas HT, ZT, TH and TZ were unable to, suggesting that the secretion signal is necessary for this transformation ability. This experiment was then repeated with *Staphyloccocus aureus* and *Escherichia coli* confirming that SHT and SZT have cross-species transformation abilities. Compared to the traditional transformation method from gram-positive bacteria, electrotransformation, the use of SHT has been demonstrated to be superior, resulting in a higher rate of transformants. As SHT and SZT transform diverse bacterial species, it is believed that other bacterial species, both gram-positive and gram-negative will be able to effectively be transformed via this method. This includes species difficult to transform, similar to *Bifidobacteria longum*, which genera include, *lactococcus, clostridium, bacilius*, and *streptococcus*.

NHP-mediated gene delivery to both bacterial as well as mammalian target cells may therefore function through a cell-mediated internalization process. It is believed that the process requires the TAT domain and is enhanced with secretion signal domain. For bacterial cell transformation, it is believed that a species specific section signal plays a significant role in transformation efficiencies, based on the reduced transformation efficiencies observed in *Staphylococcus aureus* and *Escherichia coli* assays compared to *Bifidobacteria longum*.

Example 2

Plasmid Preparation

A DNA plasmid was designed and created to use *Bifidobacteria longum* as a vector for NHP-mediated gene delivery to mammalian cells (FIGS. 1 and 2). The vector is comprised of 6 components that encode information allowing the *bifidobacteria* to carry out its designed function. The genetic components encoded include: (a) A mammalian expression cassette; (b) A prokaryotic expression cassette, encoding a novel hybrid protein; (c) A origin of replication in *E. coli*; (d) An origin of replication in *bifidobacteria longum*; (e) A selectable marker; (f) Specific DNA binding sites for the novel hybrid protein. A more detailed explanation of the structure of the two vectors is presented above in the descriptions of embodiments.

Briefly, in the plasmid pBRA2.0 SHT (FIG. 1 and SEQ ID NO: 1) the first expression cassette for expression in a gram positive bacterium comprises an HU promoter and terminator flanking the NHP encoding sequences as will be seen in FIG. 1. In pBRA2.0 SHT the second expression cassette for expression in a human cell, comprises the CMV (cytomegalovirus) promoter, a KOZAK sequence and a Thymidine Kinase polyadenylation/termination sequence, the foregoing flanking an insertion sequence for the insertion of a cargo sequence. This will be seen in SEQ ID NO: 1 wherein a GFP protein is inserted into the second expression cassette. In the embodiment pBRA2.0 SHT the vector comprises a pUC origin of replication for replication in E. coli and a pB44 origin of replication for replication in Bifidobacterium. DNA-BS denotes a nucleotide binding site (SEQ. ID. NO. 43) for a Zinc finger DNA binding protein (SEQ ID NO: 46).

Plasmid pFRG1.5 SHT is shown in FIG. 2 and SEQ ID NO: 2 and the numbers refer to the numbering of features in FIG. 2. The vector comprises gram-positive origin of replication, namely the PDOJHR origin of replication (2) whose sequence is comprised within SEQ ID NO: 28 and a gram negative origin of replication, namely the pUC ORI (1) presented as SEQ ID NO: 29. The prokaryotic expression cassette comprises a Ribosomal RNA promoter (8) and terminator (10) flanking coding sequences (9) for the hybrid protein SHT, defined elsewhere herein. The mammalian gene expression cassette comprises a CMV promoter (4) and a TK Poly A site and terminator (6). In this case the inserted gene is a GFP reporter sequence (5). The plasmid comprises DNA sequences (11) suitable for binding by the sequence comprised in the SHT hybrid protein. The selectable marker in the pFRG1.5 plasmid is a spectinomycin resistance gene (3).

Once the vector is inserted into the bifidobacteria, components (b), (d) and (f) are designed to activate due to interactions with the bifidobacteria cell machinery. As a result, the novel hybrid protein is expressed, binding to a specific binding site on the vector, and results in the entire vector-novel hybrid protein complex being secreted out of the bifidobacteria and delivered into mammalian cells. Once in the mammalian cell, the mammalian expression cassette component activates due to interactions with the cell machinery and it expresses the therapeutic gene to carry out a desired function. Components (c) and (e) are not therapeutically relevant but are required during the construction and validation of the technology.

The function of each component was tested experimentally after having the vector synthesized from GeneArt Inc.

A Mammalian Gene Expression Cassette

The ability of the vector to express the mammalian gene expression cassette was examined in various mammalian cell culture lines including LL2, Hela, Hek-293, HT-29 and CaCo-2 cells. A mammalian expression cassette that contained the Green Fluorescent Protein gene was used, allowing the use of fluorescent microscopy to detect proper function of the genetic component.

FIG. 5 depicts pBRA2.0 SHT (SEQ ID NO: 1) transfection in HeLa and HEK-293 cell lines, and resulting mammalian expression cassette function.

A Prokaryotic Gene Expression Cassette

Figure 9:
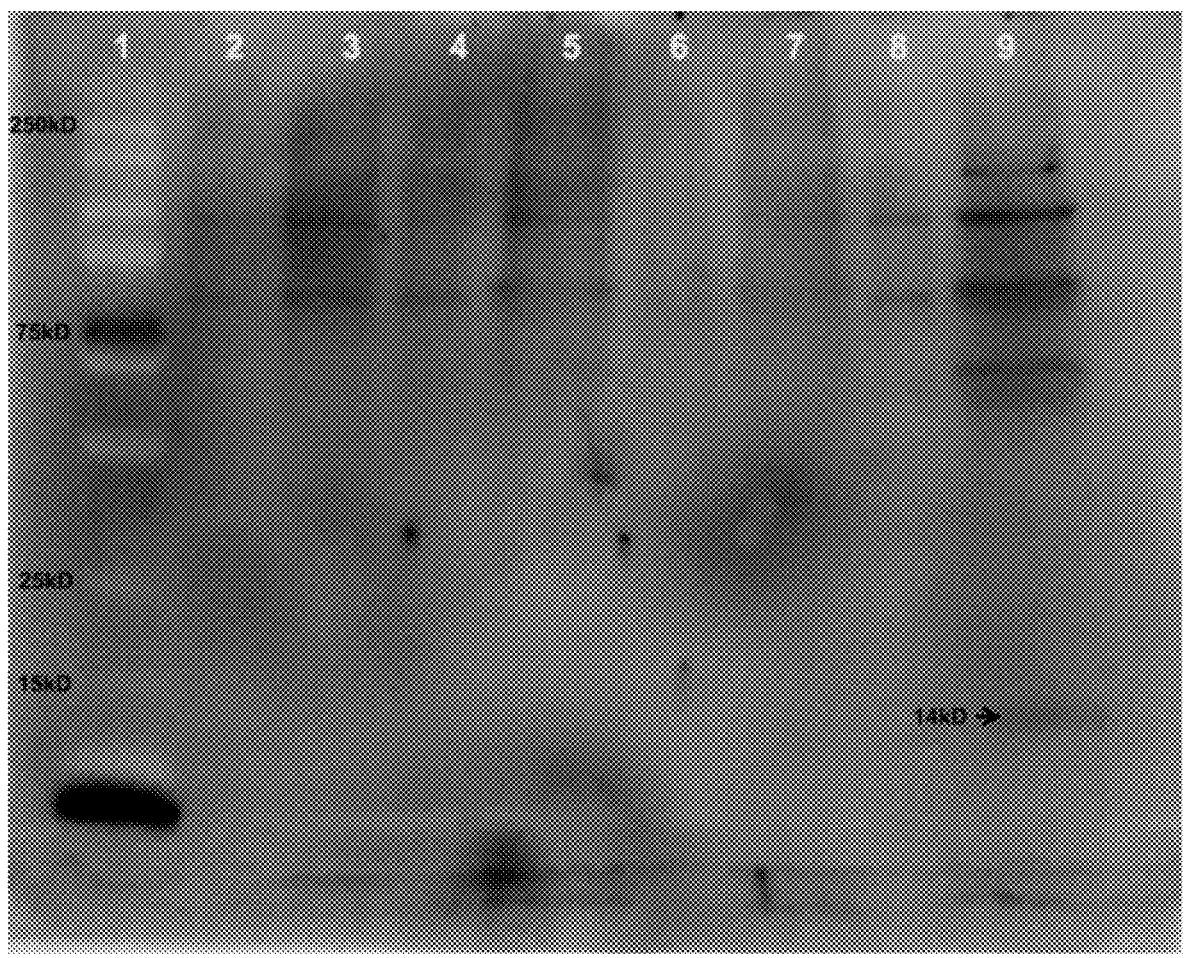
FIG. 9 shows immunoblotting analysis of the SZT hybrid protein demonstrating the expression of the SZT protein in *Bifidobacterium*.

The ability of the vector to express the prokaryotic mammalian gene expression cassette in Bifidobacteria longum was examined. To do this, immunoblot analysis on cell lysate of Bifidobacteria longum was performed. FIG. 9 depicts the immunoblot, with a band being detected at the predicted NHP size of 14 kDa in lane 9.

An Origin of Replication in E. coli and Selectable Marker

Figure 4:
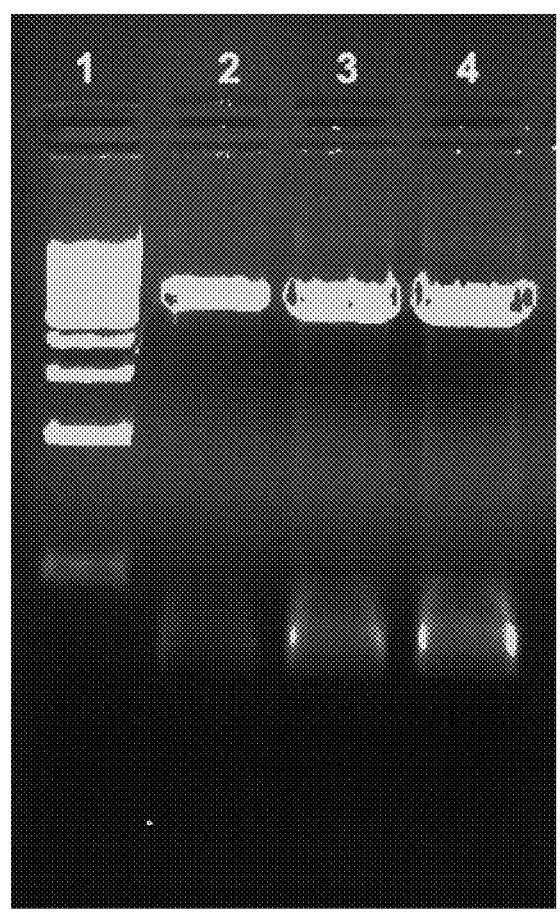
FIG. 4 shows the results of transforming *E. coli* with pBRA2.0-SHT vector according to an embodiment of the present subject matter, to confirm the effectiveness of the *E. coli* (pUC) origin of replication.

To test this component, E. coli cells were transformed with pBRA2.0 SHT (SEQ ID NO: 1). After propagating them, plasmid were purified followed by gel electrophoresis to confirm positive transformants and the function of the origin of replication. FIG. 4 depicts the gel electrophoresis of pBRA2.0 SHT (SEQ ID NO: 1, FIG. 1) purified from E. coli and confirms positive transformants. After transformation the culture was propagated in spectinomycin containing culture broth. Propagation in this broth suggests the plasmid is being replicated and the selectable marker functions.

An Origin of Replication in Bifidobacteria longum and Selectable Marker

To test this component, bifidobacteria cells were transformed with pBRA2.0 SHT (SEQ ID NO: 1, FIG. 1) purified from E. coli. After transformation the culture were propagated in spectinomycin containing culture broth. Propagation in this broth suggests the plasmid is being replicated and the selectable marker functions.

A Specific DNA Binding Site for NHPs

To test this function, purified pBRA2.0 SHT (SEQ ID NO: 1, FIG. 1) was used and bound with SHT and SZT (SEQ ID NOs 24 and 27) proteins. FIG. 3 depicts this binding assay with pBRA2.0 SHT migration being retarded with increasing NHP concentrations. Additionally, SHT and SZT mediated pBRA2.0 SHT delivery to various cell lines were performed. The positive result is the expression of the mammalian gene expression cassette encoding GFP. FIG. 5 depicts GFP positive cells post NHP-mediated pBRA2.0 SHT (SEQ ID NO: 1, FIG. 1) transfection.

Collective Vector Function:

After validating the components of the vector independently their collective function as a gene delivery system were examined. To do so, NHP-bound pBRA2.0 SHT (SEQ ID NO: 1, FIG. 1) was screened for in the supernatant of Bifidobacteria longum cultures.

Figure 6:
FIG. 6 shows the secretion of pBRA2.0 SHT from *Bifidobacterium longum* cells hosting the vector.

The first step was to detect pBRA2.0 SHT (SEQ ID NO: 1, FIG. 1) plasmid DNA via PCR (FIG. 6). After rigorous centrifugation, supernatants of wild-type bifidobacteria, pTM13 positive transformants and pBRA2.0 SHT positive transformants were collected. pTM13 is the same vector as pBRA2.0 SHT without the prokaryotic gene expression cassette encoding NHP, as a result we anticipated no plasmid secretion in pTM13 transformants. After the PCR, positive controls confirmed the validity of the PCR reaction, whereas negative control, including wild-type and pTM13 positive transformants did not have template amplification. Only pBRA2.0 SHT positive transformants provided amplified template from isolated supernatant.

Figure 7:
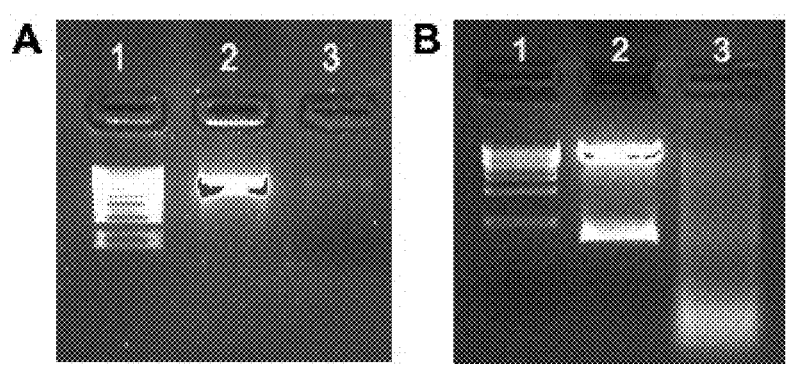
FIG. 7 shows digestion products of pBRA2.0 SHT from cell supernatant of pBRA2.0 SHT infected *Bifidobacterium longum* cells.
Figure 8:
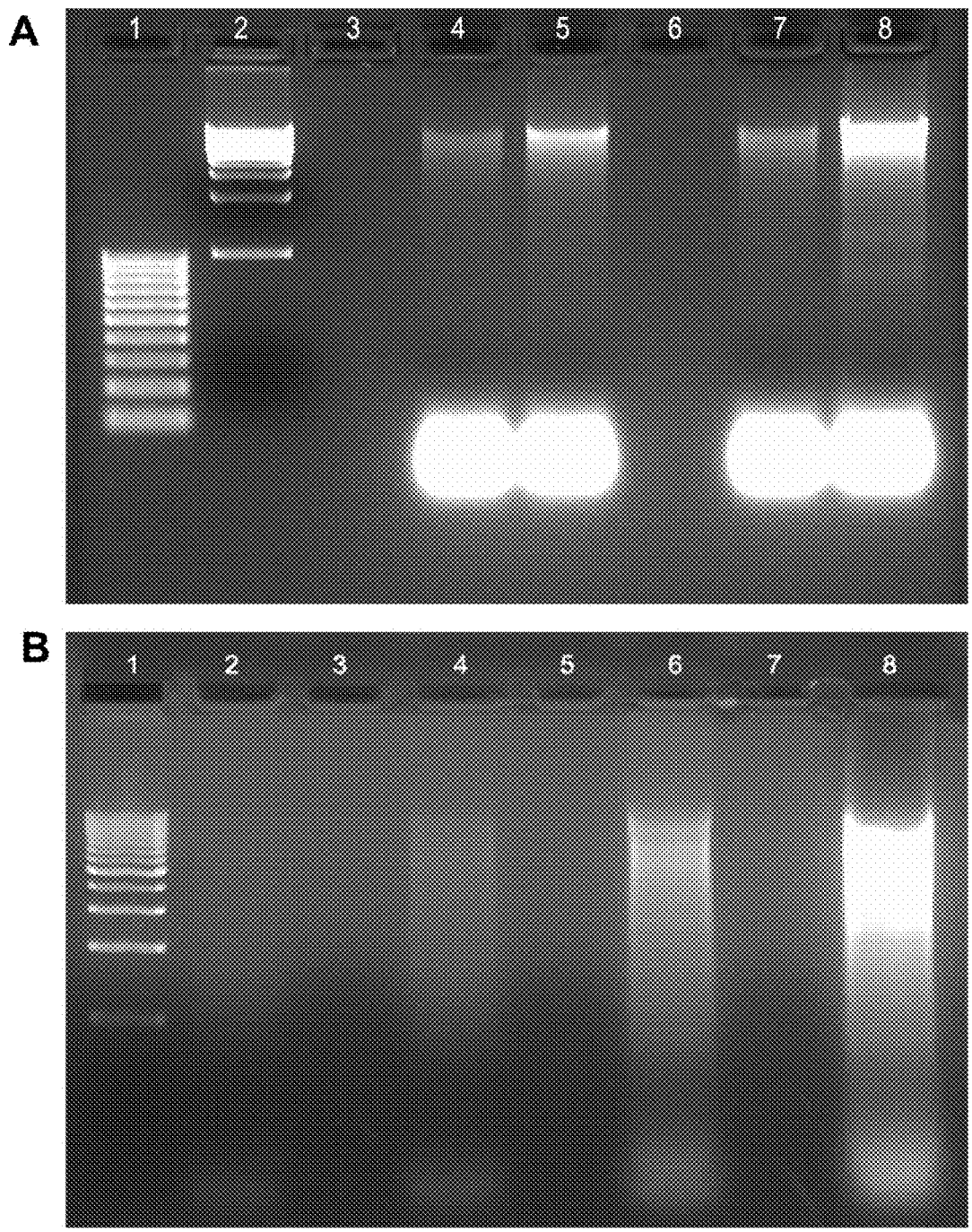
FIG. 8 shows the visualisation and digestion of concentrate cell supernatants showing secretion of pBRA2.0 SHT and its characterisation.

Second, pBRA2.0 SHT (SEQ ID NO: 1, FIG. 1) was isolated from the supernatant, using plasmid purification protocols on the collected supernatant that included modified Qiagen™ prep kits, as well as traditional phenol-chloroform purification protocols (FIGS. 7 and 8). The figures depict an isolated vector corresponding to the size of pBRA2.0 SHT (SEQ ID NO: 1, FIG. 1), and upon restriction digest analysis, was confirmed to be pBRA2.0 SHT.

It is believed that increasing the expression of NHP and the copy number of the vector will provide sufficient NHP-bound vector to detect NHP-mediated gene delivery in mammalian cells. To do this, a vector having enhanced versions of component (b) and component (d) such as pFRG1.5 (SEQ ID NO: 2, FIG. 2). It is also believed that changing the components to become species specific, for another species is relatively straight forward, as other gene expression cassettes, origins of replications, and selectable markers can be identified through genomic analysis. Based on the current designs, it is believed that the vector can be specifically designed and tested to work in species similar to *Bifidobacteria* such as *lactococcus, clostridium, staphylococcus, streptococcus* and *bacilius*.

Example 3

Culture Techniques, Serial Passagegs, Plating and Storage of Bifidobacterial Cells

*Bifidobacterium longum* cells were subcultured in screw capped anaerobic tubes containing 7-7.5 mL RCB (Reinforced Clostridial broth). After 18-24 hours of incubation, the cells were plated on RCBA (Reinforced Clostridial agar) and incubated for 24-48 hours at 37° C. under anaerobic conditions. A single colony was picked and again subcultured in screw capped anaerobic tubes containing 7-7.5 mL RCB. This procedure of 2 serial subcultures or passages (10% V/V) was used as a starter culture for all the experiments. After the cells reach an $OD_{600\ nm}$ of 1.4-1.8, cell pellets were collected and frozen at −80° C. for future use. Also, a glycerol stock of 2 mL of active culture is added to 0.5-1 mL 50% of sterile glycerol in a cryo vial and stored at −80° C. To obtain an active bacterial cell culture, the cells were constantly passaged every 2 days in sterile RCB tubes.

Example 4

Electrotransformation in *Bifidobacterium longum*

Preparation of Cells for Electroporation

*Bifidobacterium longum* overnight culture (10% V/V) was inoculated in fresh Reinforced Clostridial broth (RCB) in 10 mL screw capped anaerobic tubes and incubated at 37° C. under anaerobic conditions. This culture was serially passaged in sterile RCB tube again under anaerobic conditions at 37° C. until an $OD_{600\ nm}$ of 0.6-0.7 was reached. Once the cells reached mid-exponential phase, the cells were first chilled on ice and centrifuged at 4,500 rpm for 15 min at 4° C. in a 15 mL Falcon tube. After centrifugation, the cell pellet was resuspended and washed twice with ice-cold 0.5 M sucrose in eppendorf tubes. After, the cells were resuspended in 1/250 of the original culture volume (10 mL), which is 300 µL of ice-cold electroporation citrate buffer consisting of 1 mM ammonium citrate+0.5 M sucrose (pH-6) at 4° C. for 2.5 hours.

Electroporation Protocol

Plasmid DNA (400, 600, 800, 1000 ng: 800 ng best) were mixed with 80 µL cell suspension in a precooled Bio-Rad™ Gene Pulser™ disposable cuvette with an interelectrode distance of 0.2 cm. A Bio-Rad™ Gene Pulser™ was used to deliver a high-voltage electric pulse of 2000 V along with 25 µF capacitance and 200Ω resistance. Following electroporation, the transformant mixture was transferred in eppendorf tubes containing 900-920 µL of sterile RCB containing 0.5 M sucrose and the cells were incubated at 37° C. for 3-4 h inside the anaerobic glove bag. This procedure is required for cell recovery and the expression of antibiotic resistance marker. After cell recovery, the cells were subcultured on sterile RCB containing 25, 50, and 100 µg/mL of Ampicillin and Spectinomycin antibiotics respectively and incubated at 37° C. for 2-4 days.

Selection of Transformants

For selection, RCBS and RCBAS (Reinforced Clostridial medium with spectinomycin for vector PTM13) were used for selection of transformants. The concentrations used for selection of positive transformants were 50 µg/mL, 75 µg/mL, 100 µg/mL, 125 µg/mL and 150 µg/mL spectinomycin in tubes and agar plates. For preparing liquid selective media, the above-mentioned concentrations of spectinomycin were added to sterile RCBS tubes inside the anaerobic glove bag aseptically. For selection of transformants after electroporation, 50-100 µL of transformant mixture was plated using spread plate technique on to sterile RCAS agar plates pre-spread with appropriate concentrations of spectinomycin and incubated for 48-72 h at 37° C. inside the glove bag. Control plates containing the same concentrations of spectinomycin were used for both sterile tubes and agar plates containing (10% V/V for liquid broth and 50-100 µL of culture for agar plates) wildtype *Bifidobacerium longum* cells. After 48-72 hours or even further sometimes, the positive transformant colonies were picked using a sterile loop inside the glove bag and subcultured in tubes containing selective RCBS with 125 µg/mL spectinomycin. No growth was observed on the control RCBAS plates with the same concentrations of spectinomycin even after a week.

Screening Positive Transformants:

Plasmid Isolation

Harvest the cells (6-7 mL culture) at 5,000 rpm at 4° C. for 15 min after overnight growth from single colonies from the selective agar plates in 15 mL Falcon tubes. Wash the pellets with 1 mL of PBS once to remove excess end products in the medium. Resuspend pellets with 570 µL of solution A {6.7% sucrose, 50 mM Tris-HCl, 1 mM EDTA (pH-8.0)} and prewarm at 37° C. for 5 min. Cell lysis was performed by the addition of 145 µL of solution B {25 mM Tris-HCl (pH-8.0), 20 mg/mL Lysozyme} and incubated at 37° C. for 40-45 min. Further, 72 µL of solution C {0.25 mM EDTA, 50 mM Tris-HCl (pH-8.0)} and 42 µL of solution D {20% SDS, 50 mM Tris-HCl, 20 mM EDTA (pH-8.0)} were added, mixed gently and incubated for 10 min at 37° C. After incubation, the tubes were mixed briefly by inverting for few seconds and the genomic DNA was denatured by adding 42 µL of 3M NaOH and gently mixing for 10 min. The solution was neutralized by adding 75 µL of 2 M Tris-HCl (pH-7.0) for 3 min and the DNA was precipitated using 107 µL of 5 M NaCl for 1 min by gentle mixing. The precipitated genomic DNA was removed by centrifugation at 14,000 rpm for 10-15 min at 4° C. The supernatant was added to a new eppendorf tube containing 700 µL of phenol:chloroform:isoamyl alcohol mixture (25:24:1) and mixed vigorously. Following that, the mixture was centrifuged at 14,000 rpm for 15-20 min at room temperature. After centrifugation, the upper aqueous phase was transferred to a new tube by careful aspiration or gentle pipetting and treated with 600 µL of isopropanol and the DNA was precipitated for 30 min on ice. Then, the tubes were centrifuged at 14,000 rpm for 15-20 min at 4° C. After centrifugation, the supernatant was discarded and the pellets were washed with ice-cold (−20° C.) 70% ethanol.

After centrifugation at 14,000 rpm for 10 min, the supernantant was discarded and the pellets were air-dried for 5-10 min. The plasmid DNA pellets were resuspended in 35 µL of nuclease free water or Tris-HCl buffer. 1.5 µL of RNAse was added and incubated at 37° C. for 15-30 min.

Restriction Digestion and Agarose Gel Electrophoresis

17 µL of Plasmid DNA (550-600 ng) were added to a mixture containing 2 µL of EcoR1, 4 µL of reaction buffer, and 17 µL of water. The digestion mixture was incubated at 37° C. for 2-2.5 h. Then, the reaction was heat inactivated at 65° C. for 10-15 min. The samples including transformant (cut, uncut) plasmid DNA, control: wildtype grown in the absence of antibiotic (cut, uncut), control: wildtype grown in the presence of antibiotic (cut, uncut), vector DNA (PTM13)

cut/uncut, and DNA ladders were loaded on 1.5% agarose gel and electrophoresed to see the appropriate band patterns.

Other Plasmid Isolation Protocols

Buffers needed: TES (25 mM Tris-Cl, 10 mM EDTA, 50 mM sucrose); KOAc: 3 M K$^+$, 5 M acetate (3 M potassium-acetate, 2 M acetic acid—glacial is 17 M); PBS, phosphate buffered saline pH 7.0.

1 mL of fresh culture grown anaerobically at 37° C. with mid-log phase OD (~8-10 h) was used for plasmid isolation. Centrifuge 20 min at 4,000 RPM at 4° C. in centrifuge. Discard the supernatant, and wash in 5 mL of PBS buffer (pH 7.0). Centrifuge again and discard supernatant. Add 300-400 μL TES containing 6 mg/mL lysozyme and 40 μg/mL mutanolysin and resuspend the pellet in a 2 mL eppendorf tube. Incubate at 37° C. for 60 minutes. With O'Sullivan's method, used 200 μL of 25% sucrose with 30 mg/mL lysozyme as resuspension buffer and incubated for 15-20 min at 37° C. Meanwhile, 0.2 N NaOH and 2% SDS was freshly made to perform lysis. Add 600 μL SDS/NaOH mix to each tube. Incubate on ice for 5 min. With O'Sullivan's method, also tried with 400 μL of lysis buffer (3% SDS and 0.2 N NaOH) and mixed by inversion and incubating at room temperature for 5-7 min. Add 500 μL KOAc (3M K$^+$, 5M acetate). Incubate on ice for 2 min. Shake vigorously and centrifuge at 17,200 g/12,000 rpm, 4° C., for 15 min. With O'Sullivan's method, used 300 μL of ice-cold 3 M sodium acetate (pH-4.8) and mixed by inverting the tube and centrifuged at 13,500 rpm for 15 min at 4° C. Remove supernatant (~1 mL) into a fresh 2 mL tube and discard the pellet and remaining supernatant. Add ½ volume (500 μL) of isopropanol. Centrifuge at 17,200 g/12,000 rpm (room temperature) for 10 min. Discard the supernatant. With O'Sullivan's method, the supernatant was collected in a new eppendorf and mixed with room temperature 650 μL isopropanol and centrifuged at 13, 500 rpm for 10 min at 4° C. Wash pellet with 1 mL 70% ethanol. Air dry for 2-5 min on bench. Resuspend in 500 μL TE buffer. Add 500 μL 5M LiCl. Incubate on ice for 5 min. Centrifuge at 17,200 g/12,000 rpm for 10 min. Pour supernatant into an Eppendorf. Add 1 mL isopropanol. Incubate on the bench for 10 min. Centrifuge at 17,200 g/12,000 rpm for 10 min. Discard the supernatant. Wash the pellets with 100 μL 70% ethanol. Resuspend in 375 μL TE buffer. Add 5 μL 1 mg/mL RNase A. Incubate at 37° C. for 30 min. The same protocol was performed without LiCl step after 70% ethanol wash, the air-dried pellets were resuspended in TE and subjected to RNAase A treatment. With O'Sullivan's method, the DNA pellets were resuspended in 500 μL of sterile nuclease free water after isopropanol step and then subjected to phenol-chloroform purification. Add 700 μL phenol:chloroform:isoamyl alcohol. Vortex until thoroughly mixed. Centrifuge at top speed of microfuge for 2 min. Pipette aqueous phase (the top one) into new Eppendorf. Then repeat the procedure twice with the same volume of chloroform:isoamyl alcohol to remove any phenol. Add 750 μL straight ethanol and 125 μL 3M sodium acetate. Put at −80° C. for 30 min or −20° C. overnight. With O'Sullivan's method, the upper phase was mixed with 1 mL of ethanol (−20° C.) and centrifuged at 13,500 rpm for 15 min at 4° C. Centrifuge at 13,600 g/12,000 rpm, 4° C., for >15 min. Discard the supernatant. Wash pellet with ~100 μL 70% ethanol. Resuspend in 200 μL Tris buffer per 40 mL of original cells. With O'Sullivan's method, the DNA pellets were washed with 70% ethanol, air-dried and resuspended in 50 μL of TE containing RNAse A.

Example 5

PBRA2.0 SHT

The structure of pBRA2.0 SHT is shown in FIG. 1 and as SEQ ID NO: 1. pBRA2.0 SHT and its nucleotide sequence is presented as SEQ ID NO: 1 The vector is a plasmid and as indicated in FIG. 1 it comprises a spectinomycin resistance gene SmR, an *E. coli* pUC origin of replication and a *Bifidobacterium longum* origin of replication derived from pB44. The eukaryotic expression cassette comprises a CMV (cytomegalovirus) promoter, and a Thymidine kinase terminator and polyadenylation site from the HSV virus. A candidate or cargo sequence (designated as "GOI") can be inserted in the correct reading frame for expression through operation of the CMV promoter.

The vector also comprises an expression cassette for expression of a cargo fusion protein or NHP. As will be seen in the Figure, the prokaryotic expression cassette is framed by the Hu promoter HuP and terminator HuT. The desired NHP open reading frame is inserted between the two in the appropriate reading frame and under the control of the Hu promoter.

The HuT sequence is followed by the DNA-BS sequence which is a DNA motif bound to by a Zinc finger DNA binding domain. It will be understood that in different variants the protein chosen may have the sequence SHT, SZT, SMT, SLT (SEQ ID NOs 24, 25, 26, 27). In the examples presented here the NHP has the SHT structure, the coding nucleotide sequence for which is shown as SEQ ID NO: 24, and its corresponding DNA sequence as SEQ ID NO: 8.

In this embodiment the Signal sequence is alpha arabinosidase, SEQ ID NOs 22, 23, the DNA binding domain is the Hu domain the DNA sequence for which is presented as SEQ ID NO: 4 and the CPP domain is the TAT domain SEQ ID NO: 11. The pBRA 2.0 plasmid sequence was assembled from individual DNA sequences and synthesized commercially by LifeTein™ LCC.

Example 6 pFRG1.5

The Structure of pFRG1.5 SHT is Shown in FIG. 2 and its Nucleotide Sequence is Shown as SEQ ID NO: 2

The vector comprises gram-positive origin of replication, namely the pDOJHR origin of replication whose sequence is presented as a part of SEQ ID NO: 28 and a gram negative origin of replication, namely the pUC ORI (*E. coli* ORI) presented as SEQ ID NO: 29. The vector comprises prokaryotic and eukaryotic expression cassettes. The prokaryotic expression cassette comprises a ribosomal RNA promoter and terminator flanking coding sequences fort the hybrid protein SZT, defined elsewhere herein. The mammalian gene expression cassette comprises a CMV promoter and a TK Poly A site and terminator. In this case the inserted gene is a GFP sequence.

In the example the plasmid comprises DNA sequences suitable for binding a Zinc finger consensus sequence. The selectable marker in this plasmid is a spectinomycin resistance gene. pFRG was were obtained commercially and was synthesized using standard methods.

Example 7

Validation of Vector

In the example a pBRA2.0 SHT plasmid containing the GFP marker was transformed into bifidobacterial cells. The bifidobacterial cells were confirmed as hosting the plasmid, and expressing the encoded NHP protein. Secretion of the pBRA2.0 plasmid from the bifidobacterial cells was confirmed directly.

pBRA2.0 SHT E. coli Transformation Assay to Validate the Function of the E. coli ORI pBRA2.0 SHT was purified from transformed E. coli DH5α chemically competent cells to validate the E. coli ORI on pBRA2.0 SHT. Positive transformants were selected for on agar plates containing 100 µg/µL of spectinomycin. Cells were subject to plasmid purification using Qiagen QIAprep Spin Miniprep Kit following manufacturers protocols and subject to restriction enzyme digest using EcoR1 and visualized on a 0.8% agarose gel.

FIG. 4 shows the results of running samples of the resulting DNA digests on an agarose gel. Lanes are as follows: 1. 1 kb ladder, 2. Chemically synthesized vector, 3. pBRA2.0 SHT positive transformant A, 4. pBRA2.0 SHT positive transformant B.

pBRA2.0 SHT Transfection Assay, Validation of the Eukaryotic ORF pBRA2.0 SHT (SEQ ID NO: 1, FIG. 1) was subject to transfection for validation of eukaryotic open reading frame on pBRA2.0 SHT. pBRA2.0 SHT was transfected into human cell lines using Lipofectamine™ (Life Technologies™) following manufacturers protocols. Cells were visualized using direct fluorescence microscopy for GFP expression. The results are shown in FIG. 5: Panel 1 HEK-293 cells: A. control; B. pBRA2.0 SHT; C. pBRA2.0 SHT+ Lipofectamine™. Panel 2 HeLa cells: A. control; B. pBRA2.0 SHT; C. pBRA2.0 SHT+Lipofectamine™.

A comparison of the experimental panels 1C and 2C of FIG. 5 with the controls demonstrates the expression of GFP from the eukaryotic expression cassette in these cells.

Validation of Secretion of Vector. PCR Screening of pTM13 and pRBA2.0 Supernatants, Validation of pBRA2.0 SHT Secretion Cultures were grown to OD 1.8 where 1 mL of supernatant for wild-type, pTM13 (a plasmid not containing the SHT sequence) and pBRA2.0 SHT cultures were subjected to plasmid purification using Qiagen™ QIAprep™ Spin Miniprep Kit following manufacturers protocols. Resulting eluates were subject to PCR using pTM13/pBRA2.0 SHT specific primers to validate plasmid secretion from pBRA2.0 SHT transformants. A series of primer pairs useable to identify the presence of the plasmid are presented as SEQ ID NOs 25 and 36 (primer pair to amplify GFP sequences); SEQ ID NOs 37 and 38 (primer pair to amplify spectinomycin resistance gene sequences); and SEQ ID NOs 39 and 40 (primer pair to amplify CMV sequences). As a further confirmation of the results, the amplicons were sequenced to confirm sequence identity by at the Center for Molecular Medicine and Therapeutics at the DNA Sequencing Core Facility in Vancouver B.C. Results are shown in FIG. 6. 1: 1 kb Ladder; 2: 100 bp Ladder; 3: PCR negative control-GFP primers, no template; 4: PCR negative control-SpecR primers, no template; 5: PCR negative control-CMV primers, no template; 6: PCR positive control-GFP, pBRA-SHT plasmid. DNA; 7: PCR positive control-SpecR, pBRA-SHT plasmid. DNA; 8: PCR positive control-CMV, pBRA-SHT plasmid DNA; 9: PCR positive control-GFP, pTM13C plasmid DNA; 10: PCR positive control-SpecR, pTM13C plasmid DNA; 11: PCR positive control-CMV, pTM13C plasmid DNA; 12: Control B. longum P. DNA-GFP; 13: Control B. longum P. DNA-SpecR; 14: Control B. longum P. DNA-CMV; 15: PTM13-transformant supernatant-P. DNA-GFP; 16: PTM13-transformant supernatant-P. DNA-SpecR; 17: PTM13-transformant supernatant-P. DNA-CMV; 18: pBRA-SHT transformant supernatant-P. DNA-GFP; 19: pBRA-SHT transformant supernatant-P. DNA-SpecR; 20: pBRA-SHT transformant supernatant-P. DNA-CMV.

Thus the results of this experiment demonstrate that pBRA vector is secreted by the bacteria, whereas the pTM13 plasmid is not.

Visualization and Digestion of pBRA2.0 SHT Supernatant, Validation of pBRA2.0 SHT Secretion and Characterization pBRA2.0 SHT culture was grown to OD1.8 where 1 mL of supernatant of culture was subjected to plasmid purification using Qiagen™ QIAprep™ Spin Miniprep Kit following manufacturers protocols. Eluate was subject to restriction enzyme digest and visualized on a 0.8% PAGE to validate pBRA2.0 SHT secretion from positive transformants. The results are shown in FIG. 7. Panel A: 1. 1 kb ladder; 2. pBRA2.0 SHT; 3. pBRA2.0 SHT from pDNA Miniprep Kit. Panel B: 1. 1 kb ladder; 2. pBRA2.0 SHT digested with EcoR1; 3. pBRA2.0 SHT from pDNA Miniprep Kit digested with EcoR1.

The results of this experiment more fully confirm the secretion of pBRA2.0 SHT from the bacterial cells.

Visualizations and Digestions of Concentrated Supernatants, Validation of pBRA2.0 SHT Secretion and Characterization Wild-type, pTM13, pBRA2.0-SHT (pBRA comprising SHT SEQ ID NO: 24 in the prokaryotic expression cassette and pBRA2.0-SZT (comprising instead the SZT protein SEQ ID NO: 27) cultures were grown to an OD of 1.8. 7 mL of supernatant were concentrated under each of the aforesaid conditions using 3000 MWCO concentrators and samples were subject to phenol-chloroform plasmid DNA extraction. Results were subject to restriction enzyme digest using EcoR1 and visualized on a 0.8% PAGE to valid DNA secretion in pBRA2.0 SHT transformants. Results are shown in FIG. 8. Panel A—Phenol-chloroform samples: 1. 1 kb ladder; 2. 100 bp ladder; 3. Blank; 4. Wild-type, 5. pTM13 transformants, 6. Blank; 7. pBRA2.0-SHT; 8. pBRA2.0-SZT. Panel B: -Phenol-chloroform samples digested with EcoR1. 1. 1 kb ladder; 2. Wild-type; 3. Blank; 4. pTM13 transformants; 5. Blank; 6. pBRA2.0-SHT transformants; 7. Blank; 8 pBRA2.0-SZT transformants.

Example 8

Western Blot Analysis of SZT, SHT Validation of Bifidobacterium Specific ORF

Wild-type, and pTM13, pBRA2.0-SHT and pBRA2.0-SZT transformed cultures were grown to an OD of 1.8. Samples were loaded onto an 0.8% PACM gel and subject to electrophoresis, and transferred to a membrane for immunoblot analysis using anti-TAT antibodies to detect the expression of our hybrid proteins SHT and SZT SEQ ID NO: 27, to validate the functionality of the Bifidobacterium specific promoter and terminator. Samples were prepped from freshly grown cells washed three timex in sterile PBS. Cells were pelleted and subject to sonication in deionized water with three pulses of 20 seconds with 30 second intervals in an ice bath. Samples were quantified using via Bradford and aliquots of each sample were mixed with 4× SDS loading dye and boiled at 95 degree Celsius for 10 minutes and quenched on ice. These results suggest the promoter and terminator functionality of the HU design on pBRA2.0 is sufficient for protein expression. Results are shown in FIG. 9. 1. Precision Plus Protein™ Prestained Standards (Bio-Rad); 2. Wild-type, 3. Wild-type; 4. pTM13;

5. pTM13; 6. pBRA2.0-SHT; 7. pBRA2.0-SHT; 8. pBRA2.0-SZT; 9. pBRA2.0-SZT.

SHT and SZT Interact with pBRA2.0 SHT and Result in Gel-Shift with Increasing Concentrations of Peptide pBRA2.0 SHT was incubated with SHT or SZT SEQ ID NO: 27 in binding buffer at room temperature for 15 minutes and subject to PAGE. Results are shown in FIG. 3. 1. 1 kb ladder; 2. 100 bp ladder; 3. 500 ng of pBRA2.0 SHT; 4. 500 ng of pBRA2.0 SHT+2 ng of SHT; 5. 500 ng of pBRA2.0 SHT+5 ng of SHT; 6. 500 ng of pBRA2.0 SHT+10 ng of SHT; 7. 500 ng of pBRA2.0 SHT+20 ng of SHT; 8. 500 ng of pBRA2.0 SHT+30 ng of SHT, 9. 500 ng of pBRA2.0 SHT+40 ng of SHT; 10. 500 ng of pBRA2.0 SHT+50 ng of SHT; 11. Blank; 12. 500 ng of pBRA2.0 SHT; 13. 500 ng of pBRA2.0 SHT+2 ng of SZT; 14. 500 ng of pBRA2.0 SHT+5 ng of SZT; 15. 500 ng of pBRA2.0 SHT+10 ng of SZT; 16. 500 ng of pBRA2.0 SHT+20 ng of SZT; 17. 500 ng of pBRA2.0 SHT+30 ng of SZT, 18. 500 ng of pBRA2.0 SHT+40 ng of SZT; 19. 500 ng of pBRA2.0 SHT+50 ng of SZT; 20. Blank.

Example 10

Complexes of PBRA2.0 SHT DNA and SHT Protein and of PBRA2.0 SHT DNA and SZT Protein can Transfect and Express GFP in Mammalian Cell Lines SHT and SZT SEQ ID NO: 27 were subject to DNA binding assay followed by transfection assay to validate the cell-penetrating functional domain of each peptide. pBRA2.0 SHT was transfected into human cell lines using Lipofectamine (Life Technologies) following manufacturers protocols as a positice control. Cells were visualized using direct fluorescence microscopy for GFP expression. The results are shown in FIG. 10. Panel 1—HEK-293 cells: A. control; B. pBRA2.0 SHT; C. pBRA2.0 SHT+Lipofectamine; D. pBRA2.0-SHT complex Pane 2—HeLa cells: A. control; B. pBRA2.0 SHT; C. pBRA2.0 SHT+Lipofectamine; D. pBRA2.0-SZT complex.

Example 11

Transformation of Cells Using Hybrid Protein

A hybrid protein comprising arabinosidase signal, HU DNA binding domain and Tat transduction sequence, was bound to pBRA2.0 SHT plasmid DNA in binding buffer (150 mM NaCl 50 mM Tris pH 7.2) Unless otherwise set out below, procedures were the same as set out for Example 1 above. Protocol for the Hybrid Protein-pBRA2.0 Binding Assay were as follows:

1. Aliquot 1 ng of SHT and 150 ng of pBRA2.0 1 into a 1.5 mL Eppendorf tube containing 50 μL of NHP Binding Buffer (50 mM NaCl 50 mM Tris pH 7.2).
2. Repeat step one, while increase concentration of SHT independently by 10, 20, 30, 50, 100, 500 and 1000 ng for resultant laddering effect to determine concentration dependent Novel Hybrid Protein-pBRA2.0 Binding.
3. Leave at room temperature for 30 minutes and visualize on a 0.8% agarose gel electrophoresis.

Protocol for the Hybrid Protein-pBRA2.0 Transformation Assay:

1. Aliquot 5 μg of SHT and 400 ng of pBRA2.0 1 into a 1.5 mL Eppendorf tube containing 50 μL of NHP Binding Buffer (50 mM NaCl 50 mM Tris pH 7.2 and leave at room temperature for 30 minutes.
2. Resuspend 150 μL of $5 \times 10^8$ cells/mL into reaction mixture (Step 1).
3. Under anaerobic conditions, gently rock tube for 30 minutes containing protein-DNA complexes.
4. Add 800 μL of RCB for cell recovery under anaerobic conditions, incubate at 37° C. for 4 hours.
5. Plate 80 μL of reaction mixture on RCA-spectinomycin (200 μg/mL) resistance plates and incubate for 3 days at 37° C. under anaerobic conditions.
6. Screen for positive transformants.

SEQUENCE LISTINGS

The following sequence listings are incorporated herein and form an integral part of this disclosure.

```
SEQ ID NO: 1: pBRA2.0-SHT
CCAGGCCCGTGGAGGCGAGGAAGACGGACGGCGACGGCAAGGGCCATTGGACGAG

CGTGGCGGGGTATGGCGAGGTGTTCACGACCACGGAGCTGTTCGACGTGACGGCCG

CGCGTGACCACTTCGACGGCACCGTGGAGGCCGGGGAATGCCGTTTCTGCGCGTTTG

ACGCGCGCAACCGCGAACATCATGCGCGGAACGCCGGAAGGTTGTTCTAGCGGCCG

TGTCCGCGCCTCTGGGGCGGTTGCGCCTGCCATGGAGATCTGGGGCCGAGTCGGCCG

CGGGCTTCGAGGGAGGCGACGAGAGCACATCGCCCGCCTCAGGCGACGAGAGCAC

ATCGCCCGCCTCGGTCGGCCGCGAGGCGACGAGAGCACATCGCCCGGGCCGAGTCG

GCCGCGGGCTTCGAGGGAGGTGGGCGCGGCGGCCATGAAGTGGCTTGACAAGCATA

ATCTTGTCTGATTCGTCTATTTTCATACCCCCTTCGGGGAAATAGATGTGAAAACCCT

TATAAAACGCGGGTTTTCGCAGAAACATGCGCTAGTATCATTGATGACAACATGGAC

TAAGCAAAAGTGCTTGTCCCCTGACCCAAGAAGGATGCTTTCTCGAGATGACCCTGA

CCGGCACCCTGCGCAAAGCGTTTGCGACCACCCTGGCGGCGGCGATGCTGATTGGC

ACCCTGGCGGGCTGCAGCAGCGCGGCATACAACAAGTCTGACCTCGTTTCGAAGAT

CGCCCAGAAGTCCAACCTGACCAAGGCTCAGGCCGAGGCTGCTGTTAACGCCTTCC
```

```
AGGATGTGTTCGTCGAGGCTATGAAGTCCGGCGAAGGCCTGAAGCTCACCGGCCTG
TTCTCCGCTGAGCGCGTCAAGCGCCCGGCTCGCACCGGCCGCAACCCGCGCACTGGC
GAGCAGATTGACATTCCGGCTTCCTACGGCGTTCGTATCTCCGCTGGCTCCCTGCTG
AAGAAGGCCGTCACCGAGTATGGACGGAAGAAGCGCAGGCAGCGACGGCGATGAT
CTAGACTTCTGCTCGTAGCGATTACTTCGAGCATTACTGACGACAAAGACCCCGACC
GAGATGGTCGGGGTCTTTTTGTTGTGGTGCTGTGACGTGTTGTCCAACCGTATTATTC
CGGACTAGTTCAGCGAAGCTTCGACGAGAGCACATCGCCCGCCTCAGGCGACGAGA
GCACATCGCCCGCCTCGGTCGGCCGCGAGGCGACGAGAGCGCCTCGAAGCTTTTTTT
TTTTTGGGGCGGCTTTTTTTTTTTAAGCTTTATCTGCTCCCTGCTTGTGTGTTGGAGGT
CGCTGAGTAGTGCGCGAGCAAAATTTAAGCTACAACAAGGCAAGGCTTGACCGACA
ATTGCATGAAGAATCTGCTTAATTTAAGCTACAACAAGGCAAGGCTTGACCGACAAT
TGCATGAAGAATCTGCTAGGTACTGGCTTAACTATGCGGCATCAGAGCAGATTGTAC
TGAGAGTGCACCATATGCGGTGTGAAATACCGCACAGAATATTATTGAAGCATTTAT
CAGGGTTATTGTCTCATGAGCGGATACATATTTGAATGTATTTAGAAAGCGGCCGCG
TTAGGCGTTTTCGCGATGTACGGGCCAGATATACGCGTTGACATTGATTATTGACTA
GTTATTAATAGTAATCAATTACGGGGTCATTAGTTCATAGCCCATATATGGAGTTCC
GCGTTACATAACTTACGGTAAATGGCCCGCCTGGCTGACCGCCCAACGACCCCGCC
CATTGACGTCAATAATGACGTATGTTCCCATAGTAACGCCAATAGGGACTTTCCATT
GACGTCAATGGGTGGAGTATTTACGGTAAACTGCCCACTTGGCAGTACATCAAGTGT
ATCATATGCCAAGTACGCCCCCTATTGACGTCAATGACGGTAAATGGCCCGCCTGGC
ATTATGCCCAGTACATGACCTTATGGGACTTTCCTACTTGGCAGTACATCTACGTATT
AGTCATCGCTATTACCATGGTGATGCGGTTTTGGCAGTACATCAATGGGCGTGGATA
GCGGTTTGACTCACGGGGATTTCCAAGTCTCCACCCCATTGACGTCAATGGGAGTTT
GTTTTGGCACCAAAATCAACGGGACTTTCCAAAATGTCGTAACAACTCCGCCCCATT
GACGCAAATGGGCGGTAGGCGTGTACGGTGGGAGGTCTATATAAGCAGAGCTCGTT
TAGTGAACCGTCAGATCGCCTGGAGACGCCATCCACGCTGTTTTGACCTCCATAGAA
GACACCGGGACCGATCCAGCCTCCGGACTCTAGAGGATCGAAGAATTCGCCACCAT
GGTGAGCAAGGGCGAGGAGCTGTTCACCGGGGTGGTGCCCATCCTGGTCGAGCTGG
ACGGCGACGTAAACGGCCACAAGTTCAGCGTGTCCGGCGAGGGCGAGGGCGATGCC
ACCTACGGCAAGCTGACCCTGAAGTTCATCTGCACCACCGGCAAGCTGCCCGTGCCC
TGGCCCACCCTCGTGACCACCCTGACCTACGGCGTGCAGTGCTTCAGCCGCTACCCC
GACCACATGAAGCAGCACGACTTCTTCAAGTCCGCCATGCCCGAAGGCTACGTCCA
GGAGCGCACCATCTTCTTCAAGGACGACGGCAACTACAAGACCCGCGCCGAGGTGA
AGTTCGAGGGCGACACCCTGGTGAACCGCATCGAGCTGAAGGGCATCGACTTCAAG
GAGGACGGCAACATCCTGGGGCACAAGCTGGAGTACAACTACAACAGCCACAACGT
CTATATCATGGCCGACAAGCAGAAGAACGGCATCAAGGTGAACTTCAAGATCCGCC
ACAACATCGAGGACGGCAGCGTGCAGCTCGCCGACCACTACCAGCAGAACACCCCC
ATCGGCGACGGCCCCGTGCTGCTGCCCGACAACCACTACCTGAGCACCCAGTCCGCC
CTGAGCAAAGACCCCAACGAGAAGCGCGATCACATGGTCCTGCTGGAGTTCGTGAC
CGCCGCCGGGATCACTCTCGGCATGGACGAGCTGTACAAGTAGGAATTCTTCGATCC
CTACCGGTTAGTAATGAGTTTAAACGGGGGAGGCTAACTGAAACACGGAAGGAGAC
```

-continued

```
AATACCGGAAGGAACCCGCGCTATGACGGCAATAAAAAGACAGAATAAAACGCAC
GGGTGTTGGGTCGTTTGTTCATAAACGCGGGGTTCGGTCCCAGGGCTGGCACTCTGT
CGATACCCCACCGAGACCCCATTGGGGCCAATACGCCCGCGTTTCTTCCTTTTCCCC
ACCCCACCCCCCAAGTTCGGGTGAAGGCCCAGGGCTCGCAGCCAACGTCGGGGCGG
CAGGCCCTGCCATAGCGCGGCCGCTCGTAAAGTCTGGAAACGCGGAAGTCAGCGCC
CTGCACCATTATGTTCCGGATCTGCATCGCAGGATGCTGCTGGCTACCCTGTGGAAC
ACCTACATCTGTATTAACGAAGCGCTGGCATTGACCCTGAGTGATTTTTCTCTGGTCC
CGCCGCATCCATACCGCCAGTTGTTTACCCTCACAACGTTCCAGTAACCGGGCATGT
TCATCATCAGTAACCCGTATCGTGAGCATGGGATCCATCATGCCTCCTCTAGACCAG
CCAGGACAGAAATGCCTCGACTTCGCTGCTACCCAAGGTTGCCGGGTGACGCACAC
CGTGGAAACGGATGAAGGCACGAACCCAGTGGACATAAGCCTGTTCGGTTCGTAAG
CTGTAATGCAAGTAGCGTATGCGCTCACGCAACTGGTCCAGAACCTTGACCGAACG
CAGCGGTGGTAACGGCGCAGTGGCGGTTTTCATGGCTTGTTATGACTGTTTTTTTGG
GGTACAGTCTATGCCTCGGGCATCCAAGCAGCAAGCGCGTTACGCCGTGGGTCGAT
GTTTGATGTTATGGAGCAGCAACGATGTTACGCAGCAGGGCAGTCGCCCTAAAACA
AAGTTAAACATCATGAGGGAAGCGGTGATCGCCGAAGTATCGACTCAACTATCAGA
GGTAGTTGGCGTCATCGAGCGCCATCTCGAACCGACGTTGCTGGCCGTACATTTGTA
CGGCTCCGCAGTGGATGGCGGCCTGAAGCCACACAGTGATATTGATTTGCTGGTTAC
GGTGACCGTAAGGCTTGATGAAACAACGCGGCGAGCTTTGATCAACGACCTTTTGG
AAACTTCGGCTTCCCCTGGAGAGAGCGAGATTCTCCGCGCTGTAGAAGTCACCATTG
TTGTGCACGACGACATCATTCCGTGGCGTTATCCAGCTAAGCGCGAACTGCAATTTG
GAGAATGGCAGCGCAATGACATTCTTGCAGGTATCTTCGAGCCAGCCACGATCGAC
ATTGATCTGGCTATCTTGCTGACAAAAGCAAGAGAACATAGCGTTGCCTTGGTAGGT
CCAGCGGCGGAGGAACTCTTTGATCCGGTTCCTGAACAGGATCTATTTGAGGCGCTA
AATGAAACCTTAACGCTATGGAACTCGCCGCCCGACTGGGCTGGCGATGAGCGAAA
TGTAGTGCTTACGTTGTCCCGCATTTGGTACAGCGCAGTAACCGGCAAAATCGCGCC
GAAGGATGTCGCTGCCGACTGGGCAATGGAGCGCCTGCCGGCCCAGTATCAGCCCG
TCATACTTGAAGCTAGACAGGCTTATCTTGGACAAGAAGAAGATCGCTTGGCCTCGC
GCGCAGATCAGTTGGAAGAATTTGTCCACTACGTGAAAGGCGAGATCACCAAGGTA
GTCGGCAAATAACCCTCGAGCCACCCATGACCAAAATCCCTTAACGTGAGTTACGC
GTCGTTCCACTGAGCGTCAGACCCCGTAGAAAAGATCAAAGGATCTTCTTGAGATCC
TTTTTTTCTGCGCGTAATCTGCTGCTTGCAAACAAAAAAACCACCGCTACCAGCGGG
ATCCATGCAGCTGCGTAAGGAGAAAATACCGCATCAGGCGCTCTTCCGCTTCCTCGC
TCACTGACTCGCTGCGCTCGGTCGTTCGGCTGCGGCGAGCGGTATCAGCTCACTCAA
AGGCGGTAATACGGTTATCCACAGAACGTACGATGTGAGCAAAAGGCCAGCAAAAG
GCCAGGGACCGTAAAAAGGCCGCGTTGCTGGCGTTTTTCCATAGGCTCCGCCCCCCT
GACGAGCATCACAAAAATCGACGCTCAAGTCAGAGGTGGCGAAACCCGACAGGACT
ATAAAGATACCAGGCGTTTCCCCCTGGAAGCTCCCTCGTGCGCTCTCCTGTTCCGAC
CCTGCCGCTTACCGGATACCTGTCCGCCTTTCTCCCTTCGGGAAGCGTGGCGCTTTCT
CATAGCTCACGCTGTAGGTATCTCAGTTCGGTGTAGGTCGTTCGCTCCAAGCTGGGC
```

-continued

```
TGTGTGCACGAACCCCCCGTTCAGCCCGACCGCTGCGCCTTATCCGGTAACTATCGT

CTTGAGTCCAACCCGGTAAGACACGACTTATCGCCACTGGCAGCAGCCACTGGTAA

CAGGATTAGCAGAGCGAGGTATGTAGGCGGTGCTACAGAGTTCTTGAAGTGGTGGC

CTAACTACGGCTACACTAGAAGAACAGTATTTGGTATCTGCGCTCTGCTGAAGCCAG

TTACCTTCGGAAAAAGAGTTGGTAGCTCTTGATCCGGCAAACAAACCACCGCTGGTA

GCGGTGGTTTTTTTGTTTGCAAGCAGCAGATTACGCGCAGAAAAAAAGGATCTCAAG

AAGATCCTTTGATCTTTTCTACGGGCGTACGTCTTCCTTTTTCATCCCGGAGACGGTC

ACAGCTTGTCTGTAAGCGGATGCCGGGAGCAGACAAGCCCGTCAGGGCGCGTCAGC

GGGTGTTGGCGGGTGTCGGGGCGCAGCCATGACCCAGTCACGTAGCGATAGCGGAG

TGTATACTGGCTTAACTATGCGGCATCAGAGCAGATTGTACTGAGAGTGCACCATAT

GCGGTGTGAAATACCGCACAGAATATTATTGAAGCATTTATCAGGGTTATTGTCTCA

TGAGCGGATACATATTTGAATGTATTTAGAAAAATAAACAAATAGGGGTTCCGCGC

ACATTTCCCCGAAAAGTGCCACCTGACGTCTAAGAAACCATTATTATCATGACATTA

ACCTATAAAAATAGGCGTATCACGAGGCCCTTTCGTCTTCAAGAAAGATCTCCATGG

GAGAACCACGGGCCGGACGGATACCAGCCGCCCTCATACGAGCCGGTCAACCCCGA

ACGCAGGACCGCCCAGACGCCTTCCGATGGCCTGATCTGACGTCCGAAAAAAGGCG

CCGTGCGCCCTTTTTAAATCTTTTAAAATCTTTTTACATTCTTTTAGGCCCTCCGCAGC

CCTACTCTCCCAACGGGTTTCGGACGGTACTTAGTACAAAAGGGGAGCGAACTTAGT

ACAAAAGGGGAGCGAACTTAGTACAAAAGGGGAGCGAACTTAGTACAAAAGGGGA

GCGAACTAGTAAATAAATAAACTTTGTACTAGTATGGAGTCATGTCCAATGAGATCG

TGAAGTTCAGCAACCAGTTCAACAACGTCGCGCTGAAGAAGTTCGACGCCGTGCAC

CTGGACGTGCTCATGGCGATCGCCTCAAGGGTGAGGGAGAAGGGCACGGCCACGGT

GGAGTTCTCGTTCGAGGAGCTGCGCGGCCTCATGCGATTGAGGAAGAACCTGACCA

ACAAGCAGCTGGCAGACAAGATCGTGCAGACGAACGCGCGCCTGCTGGCGCTGAAC

TACATGTTCGAGGATTCGGGCAAGATCATCCAGTTCGCGCTGTTCACGAAGTTCGTC

ACCGACCCGCAGGAGGCGACTCTCGCGGTTGGGGTCAACGAGGAGTTCGCTTTCCT

GCTCAACGACCTGACCAGCCAGTTCACGCGCTTCGAGCTGGCCGAGTTCGCCGACCT

CAAGAGCAAGTACGCCAAGGAGTTCTACAGGCGCGCCAAGCAGTACCGCAGCTCGG

GAATCTGGAAGATCAGCCGCGATGAGTTCTGCCGACTGCTTGGCGTATCCGATTCCA

CGGCAAAATCCACCGCCAACCTGAACAGGGTCGTGCTGAAGACGATCGCCGAAGAG

TGTGGGCCTCTCCTTGGCCTGAAGATCGAGCGCCAGTACGTGAAACGCAGGCTGTCG

GGCTTCGTGTTCACGTTCGCCCGCGAGACCCCTCCGGTGATCGACG

SEQ ID NO: 2: pFRG1.5 SHT
ACGCGCTGGAGATGTTCAACGAGTAGATCGCCACGGCGACCTCCTTCCACGCGTGC

GGGCACGGGGATTCTCAAGGGGCCGGCCCGAGGCCCCTTGAGCCCGCCGGGAGGCG

CCCCCGGCAGGGCGGGAATCCAAAGGGCGGAGCCCTGTGGCCCTCCCCGGGCAGGG

GCGGGATCGTCAAGGGCGGAGCCCTTGGCCCCCTCGGGAGAGCGCACTGACACAAT

GCTACCTCCGGTAGCATTAAGTGCGCCCTCCGCCATGCGGAGGGACGGGCCGCGAC

CGGATATGCGGGGAACGTCCACGACGCGTCTTCCGTGTCCTCCGTCCTGCCTTGTGC

CGTCGATTATAATCCTCGGATAACGGACGATGATTGAACCGATTGGAGGAAACGAG

ATGCCGAAGAGTTTCGCGCAGCAGATCGAGGACGACGAGAACAAGATCAAGCGCAT
```

-continued

```
CCGGGAGCACCAGCGCATGGTCAGGGCCAAACAAGCCAAACAGGAGCGCAACGCC

CGCACCAAAAGGCTCGTGGAGACCGGAGCGATAGTGGAAAAAGCGCACGGCGGCG

CGTACGACGACGAAGGACGGCAGACGTTCTCGGATGGTCTGAACGGCATCATCTCG

GTCTACGACCCGTCCCGCGGCGGCAACGTGGACATGAGAGTCATCGACGTAATCGA

CCGGCGCATCCCCAGATTGCCAAGGTCCGAAACCACAACAGGCACGGCAGCGGCGG

CATCGCGAACCGTGCAAGCCACCGCACCACAGCCAGCCCACGCCCAACCGCAAAGC

TTCACGCCCAACCCCCAGCGCATCGAACACCGGACAGGAGCACAGCAGCCGGATCG

GTGGGCCTAGCCGGGACGGCGCAGCCCTCGCTCCGCTGGGCTGAAATATCTGACTTG

GTTCGTAACATATTTCCGACATGTCGGAAATATGTCGTATCATCGTTGCTATGAGTA

CTGAACTTCGTGAGCAGTGGGAGCAGCTTTACCTGCCGCTGCGCCCGCTGTGCACGA

ACGACTTCATCGAGGGCGTGTACCGGCAGCCCAGGGCGAAGGCGCTGGAGGGCTAC

CGGTACATCGAGGCGAACCCCAAGACCGTCAGCGACCTGCTCGTGGTCGACATCGA

CGACGCGAACGCCCGCGCGATGGCCCTATGGGAGCATGAGGGGATGCTGCCCAACG

TGATCGTGGAGAACCCGAGAAACGGCCACGCGCACGCCGTGTGGGCGCTGGCCGCC

CCGTTCAGTCGCACCGAATACGCGCGGCGCAAGCCGCTCGCCCTGGCCGCGGCGGT

CACGGAGGGGCTGCGCCGCTCGTGCGACGGGACAAGGGATATTCGGGGCTGATGA

CCAAGAACCCGCTGCACGAGGCGTGGAACAGCGAACTGGTCACCGATCACCTGTAC

GGGCTGGACGAACTGCGCGAGGCGCTGGAGGAGTCCGGGGACATGCCGCCGGCCTC

GTGGAAGCGCACGAAACGGCGCAACGTGGTCGGATTGGGCCGCAACTGCCATCTGT

TCGAGACGGCGCGCACATGGGCGTACAGGGAGGTGCGCCACCACTGGGGAGACAG

CGAGGGGCTGCGGCTGGCCATCTCGGCCGAGGCGCACGAAATGAACGCCGAACTGT

TCCCCGAGCCACTGGCATGGTCGGAGGTCGAGCAGATCGCCAAGAGCATCCACAAG

TGGATCGTCACCCAAAGCCGCATGTGGCGCGACGGCCCCACCGTCTACGAGGCGAC

ATTCATCACCGTCCAAAGCGCCCGAGGGAAAAAGTCAGGCAAGGCCAGACGAGAA

ACATTCGAACTATTCGCGAGCGAGGAGATGACGTAATGGTTATTCAAACGTTTTTGG

GGCGGCTTTTGGGCCCATGTGAGCAAAAGGCCAGCAAAAGGCCAGGGACCGTAAAA

AGGCCGCGTTGCTGGCGTTTTTCCATAGGCTCCGCCCCCCTGACGAGCATCACAAAA

ATCGACGCTCAAGTCAGAGGTGGCGAAACCCGACAGGACTATAAAGATACCAGGCG

TTTCCCCCTGGAAGCTCCCTCGTGCGCTCTCCTGTTCCGACCCTGCCGCTTACCGGAT

ACCTGTCCGCCTTTCTCCCTTCGGGAAGCGTGGCGCTTTCTCATAGCTCACGCTGTAG

GTATCTCAGTTCGGTGTAGGTCGTTCGCTCCAAGCTGGGCTGTGTGCACGAACCCCC

CGTTCAGCCCGACCGCTGCGCCTTATCCGGTAACTATCGTCTTGAGTCCAACCCGGT

AAGACACGACTTATCGCCACTGGCAGCAGCCACTGGTAACAGGATTAGCAGAGCGA

GGTATGTAGGCGGTGCTACAGAGTTCTTGAAGTGGTGGCCTAACTACGGCTACACTA

GAAGAACAGTATTTGGTATCTGCGCTCTGCTGAAGCCAGTTACCTTCGGAAAAAGAG

TTGGTAGCTCTTGATCCGGCAAACAAACCACCGCTGGTAGCGGTGGTTTTTTTGTTTG

CAAGCAGCAGATTACGCGCAGAAAAAAAGGATCTCAAGAAGATCCTTTGATCTTTT

CTACGGGTTTTTTGGGGCGGCTTTGAATTCTTTTTTTTGGGGCGGCTTTTTTTTTATG

CGCTCACGCAACTGGTCCAGAACCTTGACCGAACGCAGCGGTGGTAACGGCGCAGT

GGCGGTTTTCATGGCTTGTTATGACTGTTTTTTTGGGGTACAGTCTATGCCTCGGGCA

TCCAAGCAGCAAGCGCGTTACGCCGTGGGTCGATGTTTGATGTTATGGAGCAGCAAC
```

-continued

```
GATGTTACGCAGCAGGGCAGTCGCCCTAAAACAAAGTTAAACATCATGAGGGAAGC
GGTGATCGCCGAAGTATCGACTCAACTATCAGAGGTAGTTGGCGTCATCGAGCGCC
ATCTCGAACCGACGTTGCTGGCCGTACATTTGTACGGCTCCGCAGTGGATGGCGGCC
TGAAGCCACACAGTGATATTGATTTGCTGGTTACGGTGACCGTAAGGCTTGATGAAA
CAACGCGGCGAGCTTTGATCAACGACCTTTTGGAAACTTCGGCTTCCCCTGGAGAGA
GCGAGATTCTCCGCGCTGTAGAAGTCACCATTGTTGTGCACGACGACATCATTCCGT
GGCGTTATCCAGCTAAGCGCGAACTGCAATTTGGAGAATGGCAGCGCAATGACATT
CTTGCAGGTATCTTCGAGCCAGCCACGATCGACATTGATCTGGCTATCTTGCTGACA
AAAGCAAGAGAACATAGCGTTGCCTTGGTAGGTCCAGCGGCGGAGGAACTCTTTGA
TCCGGTTCCTGAACAGGATCTATTTGAGGCGCTAAATGAAACCTTAACGCTATGGAA
CTCGCCGCCCGACTGGGCTGGCGATGAGCGAAATGTAGTGCTTACGTTGTCCCGCAT
TTGGTACAGCGCAGTAACCGGCAAAATCGCGCCGAAGGATGTCGCTGCCGACTGGG
CAATGGAGCGCCTGCCGGCCCAGTATCAGCCCGTCATACTTGAAGCTAGACAGGCTT
ATCTTGGACAAGAAGAAGATCGCTTGGCCTCGCGCGCAGATCAGTTGGAAGAATTT
GTCCACTACGTGAAAGGCGAGATCACCAAGGTAGTCGGCAAATAAGGTACCGTTAG
GCGTTTTCGCGATGTACGGGCCAGATATACGCGTTGACATTGATTATTGACTAGTTA
TTAATAGTAATCAATTACGGGGTCATTAGTTCATAGCCCATATATGGAGTTCCGCGT
TACATAACTTACGGTAAATGGCCCGCCTGGCTGACCGCCCAACGACCCCCGCCCATT
GACGTCAATAATGACGTATGTTCCCATAGTAACGCCAATAGGGACTTTCCATTGACG
TCAATGGGTGGAGTATTTACGGTAAACTGCCCACTTGGCAGTACATCAAGTGTATCA
TATGCCAAGTACGCCCCCTATTGACGTCAATGACGGTAAATGGCCCGCCTGGCATTA
TGCCCAGTACATGACCTTATGGGACTTTCCTACTTGGCAGTACATCTACGTATTAGTC
ATCGCTATTACCATGGTGATGCGGTTTTGGCAGTACATCAATGGGCGTGGATAGCGG
TTTGACTCACGGGGATTTCCAAGTCTCCACCCCATTGACGTCAATGGGAGTTTGTTTT
GGCACCAAAATCAACGGGACTTTCCAAAATGTCGTAACAACTCCGCCCCATTGACG
CAAATGGGCGGTAGGCGTGTACGGTGGGAGGTCTATATAAGCAGAGCTCGTTTAGT
GAACCGTCAGATCGCCTGGAGACGCCATCCACGCTGTTTTGACCTCCATAGAAGACA
CCGGGACCGATCCAGCCTCCGGACTCTAGAGGATCGAAGCTAGCCACCATGGTGAG
CAAGGGCGAGGAGCTGTTCACCGGGGTGGTGCCCATCCTGGTCGAGCTGGACGGCG
ACGTAAACGGCCACAAGTTCAGCGTGTCCGGCGAGGGCGAGGGCGATGCCACCTAC
GGCAAGCTGACCCTGAAGTTCATCTGCACCACCGGCAAGCTGCCCGTGCCCTGGCCC
ACCCTCGTGACCACCCTGACCTACGGCGTGCAGTGCTTCAGCCGCTACCCCGACCAC
ATGAAGCAGCACGACTTCTTCAAGTCCGCCATGCCCGAAGGCTACGTCCAGGAGCG
CACCATCTTCTTCAAGGACGACGGCAACTACAAGACCCGCGCCGAGGTGAAGTTCG
AGGGCGACACCCTGGTGAACCGCATCGAGCTGAAGGGCATCGACTTCAAGGAGGAC
GGCAACATCCTGGGGCACAAGCTGGAGTACAACTACAACAGCCACAACGTCTATAT
CATGGCCGACAAGCAGAAGAACGGCATCAAGGTGAACTTCAAGATCCGCCACAACA
TCGAGGACGGCAGCGTGCAGCTCGCCGACCACTACCAGCAGAACACCCCCATCGGC
GACGGCCCCGTGCTGCTGCCCGACAACCACTACCTGAGCACCCAGTCCGCCCTGAGC
AAAGACCCCAACGAGAAGCGCGATCACATGGTCCTGCTGGAGTTCGTGACCGCCGC
```

```
CGGGATCACTCTCGGCATGGACGAGCTGTACAAGTAGATCTTCGATCCCTACCGGTT

AGTAATGAGTTTAAACGGGGGAGGCTAACTGAAACACGGAAGGAGACAATACCGG

AAGGAACCCGCGCTATGACGGCAATAAAAAGACAGAATAAAACGCACGGGTGTTG

GGTCGTTTGTTCATAAACGCGGGGTTCGGTCCCAGGGCTGGCACTCTGTCGATACCC

CACCGAGTCCCCATTGGGGCCAATACGCCCGCGTTTCTTCCTTTTCCCCACCCCACCC

CCCAAGTTCGGGTGAAGGCCCAGGGCTCGCAGCCAACGTCGGGGCGGCAGGCCCTG

CCATAGCTTTTTGGGGCGGCTTTTCTCGAGTCCTTCCTTAAGGACGTGCTCGTCAATT

TTTGTTTTGAGAGTCATCTATTCGGATGCTTTTCATGAAGTTTTTTATGACCCTGACC

GGCACCCTGCGCAAGGCCTTCGCCACCACCCTGGCCGCCGCCATGCTGATCGGCACC

CTGGCCGGCTGCTCCTCCGCCGCATACAACAAGTCTGACCTCGTTTCGAAGATCGCC

CAGAAGTCCAACCTGACCAAGGCTCAGGCCGAGGCTGCTGTTAACGCCTTCCAGGA

TGTGTTCGTCGAGGCTATGAAGTCCGGCGAAGGCCTGAAGCTCACCGGCCTGTTCTC

CGCTGAGCGCGTCAAGCGCCCGGCTCGCACCGGCCGCAACCCGCGCACTGGCGAGC

AGATTGACATTCCGGCTTCCTACGGCGTTCGTATCTCCGCTGGCTCCCTGCTGAAGA

AGGCCGTCACCGAGTATGGACGGAAGAAGCGCAGGCAGCGACGGCGATGAGGAAG

AAGCGCAGGCAGCGACGGCGATGAGGGTTTGCGCTTGCGTCGTGGAGGGAGCGGAA

CGCCGAAAAAGGATCC

SEQ ID NO: 3: Lac I DNA binding domain
AAATATGTAACGTTATACGATGTCGCAGAGTATGCCGGTGTCTCTCATCAGACCGTT

TCCCGCGTGGTGAACCAGGCCAGCCACGTTTCTGCGAAAACGCGGGAAAAAGTGGA

AGCGGCGATGGCGGAGCTGAATTACATTCCCAACCGCGTGGCACAACAACTGGCGG

GCAAACAGTCGTTGCTGATT

SEQ ID NO: 4: HU DNA binding domain
GCATACAACAAGTCTGACCTCGTTTCGAAGATCGCCCAGAAGTCCAACCTGACCAA

GGCTCAGGCCGAGGCTGCTGTTAACGCCTTCCAGGATGTGTTCGTCGAGGCTATGAA

GTCCGGCGAAGGCCTGAAGCTCACCGGCCTGTTCTCCGCTGAGCGCGTCAAGCGCCC

GGCTCGCACCGGCCGCAACCCGCGCACTGGCGAGCAGATTGACATTCCGGCTTCCTA

CGGCGTTCGTATCTCCGCTGGCTCCCTGCTGAAGAAGGCCGTCACCGAG

SEQ ID NO: 5: Mer R DNA binding domain
GAAAACAATTTGGAGAACCTGACCATTGGCGTTTTCGCCAGGACGGCCGGGGTCAA

TGTGGAGACCATCCGGTTCTATCAGCGCAAGGGCTTGCTCCCGGAACCGGACAAGC

CTTACGGCAGCATTCGCCGCTATGGCGAGACGGATGTAACGCGGGTGCGCTTCGTGA

AATCAGCCCAGCGGTTGGGCTTCAGCCTGGATGAGATCGCCGAGCTGCTGCGGCTG

GAGGATGGCACCCATTGCGAGGAAGCCAGCAGCCTGGCCGAGCACAAGCTCAAGG

ACGTGCGCGAGAGGATGGCTGACCTGGCGCGCATGGAGGCCGTGCTGTCTGATTTG

GTGTGCGCCTGCCATGCGCGAAGGGGGAACGTTTCCTGCCCGCTGATCGCGTCACTA

CAGGGTGGAGCAAGCTTGGCAGGTTCGGCTATGCCT

SEQ ID NO: 6: Zinc finger DNA binding domain.
GAAAAACTGCGCAACGGCAGCGGCGATCCGGGCAAAAAAAAACAGCATGCGTGCC

CGGAATGCGGCAAAAGCTTTAGCCAGAGCAGCGATCTGCAGCGCCATCAGCGCACC

CATACCGGCGAAAAACCGTATAAATGCCCGGAATGCGGCAAAAGCTTTAGCCGCAG

CGATGAACTGCAGCGCCATCAGCGCACCCATACCGGCGAAAAACCGTATAAATGCC

CGGAATGCGGCAAAAGCTTTAGCCGCAGCGATCATCTGAGCCGCCATCAGCGCACC
```

CATCAGAACAAAAAA

SEQ ID NO: 7: Coding sequence for SMT protein
ATGACCCTGACCGGCACCCTGCGCAAAGCGTTTGCGACCACCCTGGCGGCGGCGAT

GCTGATTGGCACCCTGGCGGGCTGCAGCAGCGCGGAAAACAATTTGGAGAACCTGA

CCATTGGCGTTTTCGCCAGGACGGCCGGGGTCAATGTGGAGACCATCCGGTTCTATC

AGCGCAAGGGCTTGCTCCCGGAACCGGACAAGCCTTACGGCAGCATTCGCCGCTAT

GGCGAGACGGATGTAACGCGGGTGCGCTTCGTGAAATCAGCCCAGCGGTTGGGCTT

CAGCCTGGATGAGATCGCCGAGCTGCTGCGGCTGGAGGATGGCACCCATTGCGAGG

AAGCCAGCAGCCTGGCCGAGCACAAGCTCAAGGACGTGCGCGAGAGGATGGCTGA

CCTGGCGCGCATGGAGGCCGTGCTGTCTGATTTGGTGTGCGCCTGCCATGCGCGAAG

GGGGAACGTTTCCTGCCCGCTGATCGCGTCACTACAGGGTGGAGCAAGCTTGGCAG

GTTCGGCTATGCCTTATGGACGGAAGAAGCGCAGGCAGCGACGGCGATGA

SEQ ID NO: 8: Coding sequence for SHT protein
ATGACCCTGACCGGCACCCTGCGCAAAGCGTTTGCGACCACCCTGGCGGCGGCGAT

GCTGATTGGCACCCTGGCGGGCTGCAGCAGCGCGGCATACAACAAGTCTGACCTCG

TTTCGAAGATCGCCCAGAAGTCCAACCTGACCAAGGCTCAGGCCGAGGCTGCTGTT

AACGCCTTCCAGGATGTGTTCGTCGAGGCTATGAAGTCCGGCGAAGGCCTGAAGCTC

ACCGGCCTGTTCTCCGCTGAGCGCGTCAAGCGCCCGGCTCGCACCGGCCGCAACCCG

CGCACTGGCGAGCAGATTGACATTCCGGCTTCCTACGGCGTTCGTATCTCCGCTGGC

TCCCTGCTGAAGAAGGCCGTCACCGAGTATGGACGGAAGAAGCGCAGGCAGCGACG

GCGATGA

SEQ ID NO: 9: Coding sequence for SLT
ATGACCCTGACCGGCACCCTGCGCAAAGCGTTTGCGACCACCCTGGCGGCGGCGAT

GCTGATTGGCACCCTGGCGGGCTGCAGCAGCGCGAAATATGTAACGTTATACGATGT

CGCAGAGTATGCCGGTGTCTCTCATCAGACCGTTTCCCGCGTGGTGAACCAGGCCAG

CCACGTTTCTGCGAAAACGCGGGAAAAAGTGGAAGCGGCGATGGCGGAGCTGAATT

ACATTCCCAACCGCGTGGCACAACAACTGGCGGGCAAACAGTCGTTGCTGATTTATG

GACGGAAGAAGCGCAGGCAGCGACGGCGATGA

SEQ ID NO: 10: cODING SEQUENCE FOR SZT
ATGACCCTGACCGGCACCCTGCGCAAAGCGTTTGCGACCACCCTGGCGGCGGCGAT

GCTGATTGGCACCCTGGCGGGCTGCAGCAGCGCGGAAAAACTGCGCAACGGCAGCG

GCGATCCGGGCAAAAAAAAACAGCATGCGTGCCCGGAATGCGGCAAAAGCTTTAGC

CAGAGCAGCGATCTGCAGCGCCATCAGCGCACCCATACCGGCGAAAAACCGTATAA

ATGCCCGGAATGCGGCAAAAGCTTTAGCCGCAGCGATGAACTGCAGCGCCATCAGC

GCACCCATACCGGCGAAAAACCGTATAAATGCCCGGAATGCGGCAAAAGCTTTAGC

CGCAGCGATCATCTGAGCCGCCATCAGCGCACCCATCAGAACAAAAAATATGGACG

GAAGAAGCGCAGGCAGCGACGGCGATGA

SEQ ID NO: 18: Alpha-amylase Sequence with extra amino acids that permit cleavage
Atgaaacatcggaaacccgcaccggcctggcataggctggggctgaagattagcaagaaagtggtggtcggcatcaccgcc gcggcgaccgccttcggcggactggcaatcgccagcaccgcagcacaggccagcacc SEQ ID NO: 19: 46 amino acid Alpha amylase Signal peptide with putative cleavage site
MKHRKPAPAWHRLGLKISKKVVVGITAAATAFGGLAIASTAAQAST SEQ ID NO: 20: Cleaved alpha amylase signal peptide
atgaaacatcggaaacccgcaccggcctggcataggctggggctgaagattagcaagaaagtggtggtcg gcatcaccgccgcggcgaccgccttcggcggactggcaatcgccagcaccgcagcacaggcc SEQ ID NO: 21: 44 amino acid predicted cleaved alpha amylase signal peptide
(no cleavage signal)
MKHRKPAPAWHRLGLKISKKVVVGITAAATAFGGLAIASTAAQA SEQ ID NO: 22: Arabinosidase signal peptide coding sequence.
ACCCTGACCGGCACCCTGCGCAAAGCGTTTGCGACCACCCTGGCGGCGGCGATGCT

GATTGGCACCCTGGCGGGCTGCAGCAGCGCG

SEQ ID NO: 23: Arabinosidase signal peptide
TLTGTLRKAFATTLAAAMLIGTLAGCSSA

SEQ ID NO: 24: SHT HYBRID PROTEIN (133 AMINO ACIDS)
MTLTGTLRKAFATTLAAAMLIGTLAGCSSAAYNKSDLVSKIAQKSNLTKAQAEAAVNA

FQDVFVEAMKSGEGLKLTGLFSAERVKRPARTGRNPRTGEQIDIPASYGVRISAGSLLKK

AVTEYGRKKRRQRRR

SEQ ID NO: 25: SLT HYBRID PROTEIN (104 AMINO ACIDS)
MTLTGTLRKAFATTLAAAMLIGTLAGCSSAKYVTLYDVAEYAGVSHQTVSRVVNQASH

VSAKTREKVEAAMAELNYIPNRVAQQLAGKQSLLIYGRKKRRQRRR

SEQ ID NO: 26: SMT HYBRID PROTEIN (184 AMINO ACIDS)
MTLTGTLRKAFATTLAAAMLIGTLAGCSSAENNLENLTIGVFARTAGVNVETIRFYQRK

GLLPEPDKPYGSIRRYGETDVTRVRFVKSAQRLGFSLDEIAELLRLEDGTHCEEASSLAE

HKLKDVRERMADLARMEAVLSDLVCACHARRGNVSCPLIASLQGGASLAGSAMPYGR

KKRRQRRR

SEQ ID NO: 27: SZT HYBRID PROTEIN (139 AMINO ACIDS)
MTLTGTLRKAFATTLAAAMLIGTLAGCSSAEKLRNGSGDPGKKKQHACPECGKSFSQSS

DLQRHQRTHTGEKPYKCPECGKSFSRSDELQRHQRTHTGEKPYKCPECGKSFSRSDHLS

RHQRTHQNKKYGRKKRRQRRR

SEQ ID NO: 28: SEQUENCE COMPRISING PDOHJR ORI
ACGCGCTGGAGATGTTCAACGAGTAGATCGCCACGGCGACCTCCTTCCACGCGTGC

GGGCACGGGGATTCTCAAGGGGCCGGCCCGAGGCCCCTTGAGCCCGCCGGGAGGCG

CCCCCGGCAGGGCGGGAATCCAAAGGGCGGAGCCCTGTGGCCCTCCCCGGGCAGGG

GCGGGATCGTCAAGGGCGGAGCCCTTGGCCCCCTCGGGAGAGCGCACTGACACAAT

GCTACCTCCGGTAGCATTAAGTGCGCCCTCCGCCATGCGGAGGGACGGGCCGCGAC

CGGATATGCGGGGAACGTCCACGACGCGTCTTCCGTGTCCTCCGTCCTGCCTTGTGC

CGTCGATTATAATCCTCGGATAACGGACGATGATTGAACCGATTGGAGGAAACGAG

ATGCCGAAGAGTTTCGCGCAGCAGATCGAGGACGACGAGAACAAGATCAAGCGCAT

CCGGGAGCACCAGCGCATGGTCAGGGCCAAACAAGCCAAACAGGAGCGCAACGCC

CGCACCAAAAGGCTCGTGGAGACCGGAGCGATAGTGGAAAAAGCGCACGGCGGCG

CGTACGACGACGAAGGACGGCAGACGTTCTCGGATGGTCTGAACGGCATCATCTCG

GTCTACGACCCGTCCCGCGGCGGCAACGTGGACATGAGAGTCATCGACGTAATCGA

CCGGCGCATCCCCAGATTGCCAAGGTCCGAAACCACAACAGGCACGGCAGCGGCGG

CATCGCGAACCGTGCAAGCCACCGCACCACAGCCAGCCCACGCCCAACCGCAAAGC

TTCACGCCCAACCCCCAGCGCATCGAACACCGGACAGGAGCACAGCAGCCGGATCG

GTGGGCCTAGCCGGGACGGCGCAGCCCTCGCTCCGCTGGGCTGAAATATCTGACTTG

GTTCGTAACATATTTCCGACATGTCGGAAATATGTCGTATCATCGTTGCTATGAGTA

CTGAACTTCGTGAGCAGTGGGAGCAGCTTTACCTGCCGCTGCGCCCGCTGTGCACGA

ACGACTTCATCGAGGGCGTGTACCGGCAGCCCAGGGCGAAGGCGCTGGAGGGCTAC

CGGTACATCGAGGCGAACCCCAAGACCGTCAGCGACCTGCTCGTGGTCGACATCGA

CGACGCGAACGCCCGCGCGATGGCCCTATGGGAGCATGAGGGGATGCTGCCCAACG

TGATCGTGGAGAACCCGAGAAACGGCCACGCGCACGCCGTGTGGGCGCTGGCCGCC

CCGTTCAGTCGCACCGAATACGCGCGGCGCAAGCCGCTCGCCCTGGCCGCGGCGGT

CACGGAGGGGCTGCGCCGCTCGTGCGACGGGACAAGGGATATTCGGGGCTGATGA

CCAAGAACCCGCTGCACGAGGCGTGGAACAGCGAACTGGTCACCGATCACCTGTAC

GGGCTGGACGAACTGCGCGAGGCGCTGGAGGAGTCCGGGGACATGCCGCCGGCCTC

GTGGAAGCGCACGAAACGGCGCAACGTGGTCGGATTGGGCCGCAACTGCCATCTGT

TCGAGACGGCGCGCACATGGGCGTACAGGGAGGTGCGCCACCACTGGGGAGACAG

CGAGGGGCTGCGGCTGGCCATCTCGGCCGAGGCGCACGAAATGAACGCCGAACTGT

TCCCCGAGCCACTGGCATGGTCGGAGGTCGAGCAGATCGCCAAGAGCATCCACAAG

TGGATCGTCACCCAAAGCCGCATGTGGCGCGACGGCCCCACCGTCTACGAGGCGAC

ATTCATCACCGTCCAAAGCGCCCGAGGGAAAAAGTCAGGCAAGGCCAGACGAGAA

ACATTCGAACTATTCGCGAGCGAGGAGATGACGTAA

SEQ ID NO: 29 : *E. COLI*/PUCORI.
ATGTGAGCAAAAGGCCAGCAAAAGGCCAGGGACCGTAAAAAGGCCGCGTTGCTGG

CGTTTTTCCATAGGCTCCGCCCCCTGACGAGCATCACAAAAATCGACGCTCAAGTC

AGAGGTGGCGAAACCCGACAGGACTATAAAGATACCAGGCGTTTCCCCCTGGAAGC

TCCCTCGTGCGCTCTCCTGTTCCGACCCTGCCGCTTACCGGATACCTGTCCGCCTTTC

TCCCTTCGGGAAGCGTGGCGCTTTCTCATAGCTCACGCTGTAGGTATCTCAGTTCGGT

GTAGGTCGTTCGCTCCAAGCTGGGCTGTGTGCACGAACCCCCCGTTCAGCCCGACCG

CTGCGCCTTATCCGGTAACTATCGTCTTGAGTCCAACCCGGTAAGACACGACTTATC

GCCACTGGCAGCAGCCACTGGTAACAGGATTAGCAGAGCGAGGTATGTAGGCGGTG

CTACAGAGTTCTTGAAGTGGTGGCCTAACTACGGCTACACTAGAAGAACAGTATTTG

GTATCTGCGCTCTGCTGAAGCCAGTTACCTTCGGAAAAAGAGTTGGTAGCTCTTGAT

CCGGCAAACAAACCACCGCTGGTAGCGGTGGTTTTTTTGTTTGCAAGCAGCAGATTA

CGCGCAGAAAAAAAGGATCTCAAGAAGATCCTTTGATCTTTTCTACGGGTTTTTTG

GGGCGGCTTT

SEQ ID NO: 30: PB44 ORI
CCCTCATACGAGCCGGTCAACCCCGAACGCAGGACCGCCCAGACGCCTTCCGATGG

CCTGATCTGACGTCCGAAAAAAGGCGCCGTGCGCCCTTTTTAAATCTTTTAAAATCT

TTTTACATTCTTTTAGGCCCTCCGCAGCCCTACTCTCCCAACGGGTTTCGGACGGTAC

TTAGTACAAAAGGGGAGCGAACTTAGTACAAAAGGGGAGCGAACTTAGTACAAAA

GGGGAGCGAACTTAGTACAAAAGGGGAGCGAACTAGTAAATAAATAAACTTTGTAC

TAGTATGGAGTCATGTCCAATGAGATCGTGAAGTTCAGCAACCAGTTCAACAACGTC

GCGCTGAAGAAGTTCGACGCCGTGCACCTGGACGTGCTCATGGCGATCGCCTCAAG

GGTGAGGGAGAAGGGCACGGCCACGGTGGAGTTCTCGTTCGAGGAGCTGCGCGGCC

TCATGCGATTGAGGAAGAACCTGACCAACAAGCAGCTGGCAGACAAGATCGTGCAG

ACGAACGCGCGCCTGCTGGCGCTGAACTACATGTTCGAGGATTCGGGCAAGATCAT

CCAGTTCGCGCTGTTCACGAAGTTCGTCACCGACCCGCAGGAGGCGACTCTCGCGGT

TGGGGTCAACGAGGAGTTCGCTTTCCTGCTCAACGACCTGACCAGCCAGTTCACGCG

```
CTTCGAGCTGGCCGAGTTCGCCGACCTCAAGAGCAAGTACGCCAAGGAGTTCTACA

GGCGCGCCAAGCAGTACCGCAGCTCGGGAATCTGGAAGATCAGCCGCGATGAGTTC

TGCCGACTGCTTGGCGTATCCGATTCCACGGCAAAATCCACCGCCAACCTGAACAGG

GTCGTGCTGAAGACGATCGCCGAAGAGTGTGGGCCTCTCCTTGGCCTGAAGATCGA

GCGCCAGTACGTGAAACGCAGGCTGTCGGGCTTCGTGTTCACGTTCGCCCGCGAGAC

CCCTCCGGTGATCGACGCCAGGCCCGTGGAGGCGAGGAAGACGGACGGCGACGGC

AAGGGCCATTGGACGAGCGTGGCGGGGTATGGCGAGGTGTTCACGACCACGGAGCT

GTTCGACGTGACGGCCGCGCGTGACCACTTCGACGGCACCGTGGAGGCCGGGGAAT

GCCGTTTCTGCGCGTTTGACGCGCGCAACCGCGAACATCATGCGCGGAACGCCGGA

AGGTTGTTCTAGCGGCCGTGTCCGCGCCTCTGGGCGGTTGCGCCTGCCATGGAGAT

CT

SEQ ID NO: 31: TAT
TATGGACGGAAGAAGCGCAGGCAGCGACGGCGA

SEQ ID NO: 32: P-beta MPG (gp41-5V40)
GGCGCGCTGTTTCTGGGCTTTCTGGGCGCGGCGGGCAGCACCATGGGCGCGTGGAG

CCAGCCGAAAAAAAAACGCAAAGTG

SEQ ID NO: 33: Transportan (Galanin-mastoparan)
GGCTGGACCCTGAACAGCGCGGGCTATCTGCTGGGCAAAATTAACCTGAAAGCGCT

GGCGGCGCTGGCGAAAAAAATTCTG

SEQ ID NO: 34: Pep-1 (Trp-rich motif-5V40)
AAAGAAACCTGGTGGGAAACCTGGTGGACCGAATGGAGCCAGCCGAAAAAAAAAC

GCCGCGTG

SEQ ID NO: 35: GFP forward primer
GAATTCGCCACCATGGTGAGCAAGGG

SEQ ID NO: 36 GFP Reverse Primer (Compliment):
TGGACGAGCTGTACAAGTAGGAATTC

SEQ ID NO: 37: Spectinomycin Forward Primer:
ATGCGCTCACGCAACTGGTCCAGAACCTT

SEQ ID NO: 38: Spectinomycin Reverse Primer (Compliment):
TTATTTGCCGACTACCTTGGTGATCTCGC SEQ ID NO: 39 CMV Forward Primer:
GTTAGGCGTTTTCGCGATGTACGGGCCAGATA SEQ ID NO: 40: CMV Reverse Primer (Compliment):
GTGGCGAATTCTTCGATCCTCTAGAGTCCGGAG SEQ ID NO: 41: MerR DNA recognition site
AAGCTTGTCGACCTGCAGCCTTGGCGCTTGACTCCGTACATGAGTACGGAAGTAAGG

TTACGCTATCCTTGGCTGCAGAAGCTT

SEQ ID NO: 42: LacI repressor DNA binding site
AAGCTTCAGTGAGCGCAACGCAATTAATGTGAGTTAGCTCACTCATTAGGCACCCCA

GGCTTTACACTTTATGCTTCCGGCTCGTATGTTGTGTGGAATTGTGAGCGCTCACAAA

AGCTT

SEQ ID NO: 43: Synthetic zinc finger DNA recognition site
AAGCTTTTTTTTTTTGGGGCGGCTTTTTTTTTTAAGCTT SEQ ID NO: 44: HU DNA binding domain
AYNKSDLVSKIAQKSNLTKAQAEAAVNAFQDVFVEAMKSGEGLKLTGLFSAERVKRPA

RTGRNPRTGEQIDIPASYGVRISAGSLLKKAVTE

SEQ ID NO: 45: Mer R DNA binding domain
MENNLENLTIGVFARTAGVNVETIRFYQRKGLLPEPDKPYGSIRRYGETDVTRVRFVKS
```

-continued

AQRLGFSLDEIAELLRLEDGTHCEEASSLAEHKLKDVRERMADLARMEAVLSDLVCAC

HARRGNVSCPLIASLQGGASLAGSAMP

SEQ ID NO: 46: Zn finger DNA binding domain
MEKLRNGSGDPGKKKQHACPECGKSFSQSSDLQRHQRTHTGEKPYKCPECGKSFSRSD

ELQRHQRTHTGEKPYKCPECGKSFSRSDHLSRHQRTHQNKK

SEQ ID NO: 47: Lac I DNA binding domain
MKYVTLYDVAEYAGVSHQTVSRVVNQASHVSAKTREKVEAAMAELNYIPNRVAQQLA

GKQSLLI

SEQ ID NO: 48: Prokaryotic expression cassette comprising Hu Promoter and terminator
TCCTTCCTTAAGGACGTGCTCGTCAATTTTTGTTTTGAGAGTCATCTATTCGGATGCT

TTTCATGAAGTTTTTTGGAAGAAGCGCAGGCAGCGACGGCGATGAGGGTTTGCGCTT

GCGTCG

SEQ ID NO: 49: Eukaryotic Expression Cassette comprising CMV promoter, Kozak sequence
and TK Poly A site and terminator, flanking GFP coding sequences to be expressed
GGTTAGGCGTTTTCGCGATGTACGGGCCAGATATACGCGTTGACATTGATTATTGAC

TAGTTATTAATAGTAATCAATTACGGGGTCATTAGTTCATAGCCCATATATGGAGTT

CCGCGTTACATAACTTACGGTAAATGGCCCGCCTGGCTGACCGCCCAACGACCCCCG

CCCATTGACGTCAATAATGACGTATGTTCCCATAGTAACGCCAATAGGGACTTTCCA

TTGACGTCAATGGGTGGAGTATTTACGGTAAACTGCCCACTTGGCAGTACATCAAGT

GTATCATATGCCAAGTACGCCCCCTATTGACGTCAATGACGGTAAATGGCCCGCCTG

GCATTATGCCCAGTACATGACCTTATGGGACTTTCCTACTTGGCAGTACATCTACGT

ATTAGTCATCGCTATTACCATGGTGATGCGGTTTTGGCAGTACATCAATGGGCGTGG

ATAGCGGTTTGACTCACGGGGATTTCCAAGTCTCCACCCCATTGACGTCAATGGGAG

TTTGTTTTGGCACCAAAATCAACGGGACTTTCCAAAATGTCGTAACAACTCCGCCCC

ATTGACGCAAATGGGCGGTAGGCGTGTACGGTGGGAGGTCTATATAAGCAGAGCTC

GTTTAGTGAACCGTCAGATCGCCTGGAGACGCCATCCACGCTGTTTTGACCTCCATA

GAAGACACCGGGACCGATCCAGCCTCCGGACTCTAGAGGATCGAAGCTAGCCACCA

TGGTGAGCAAGGGCGAGGAGCTGTTCACCGGGGTGGTGCCCATCCTGGTCGAGCTG

GACGGCGACGTAAACGGCCACAAGTTCAGCGTGTCCGGCGAGGGCGAGGGCGATGC

CACCTACGGCAAGCTGACCCTGAAGTTCATCTGCACCACCGGCAAGCTGCCCGTGCC

CTGGCCCACCCTCGTGACCACCCTGACCTACGGCGTGCAGTGCTTCAGCCGCTACCC

CGACCACATGAAGCAGCACGACTTCTTCAAGTCCGCCATGCCCGAAGGCTACGTCC

AGGAGCGCACCATCTTCTTCAAGGACGACGGCAACTACAAGACCCGCGCCGAGGTG

AAGTTCGAGGGCGACACCCTGGTGAACCGCATCGAGCTGAAGGGCATCGACTTCAA

GGAGGACGGCAACATCCTGGGGCACAAGCTGGAGTACAACTACAACAGCCACAAC

GTCTATATCATGGCCGACAAGCAGAAGAACGGCATCAAGGTGAACTTCAAGATCCG

CCACAACATCGAGGACGGCAGCGTGCAGCTCGCCGACCACTACCAGCAGAACACCC

CCATCGGCGACGGCCCCGTGCTGCTGCCCGACAACCACTACCTGAGCACCCAGTCCG

CCCTGAGCAAAGACCCCAACGAGAAGCGCGATCACATGGTCCTGCTGGAGTTCGTG

ACCGCCGCCGGGATCACTCTCGGCATGGACGAGCTGTACAAGTAGATCTTCGATCCC

TACCGGTTAGTAATGAGTTTAAACGGGGGAGGCTAACTGAAACACGGAAGGAGACA

ATACCGGAAGGAACCCGCGCTATGACGGCAATAAAAAGACAGAATAAAACGCACG

GGTGTTGGGTCGTTTGTTCATAAACGCGGGGTTCGGTCCCAGGGCTGGCACTCTGTC

GATACCCCACCGAGTCCCCATTGGGGCCAATACGCCCGCGTTTCTTCCTTTTCCCCAC

CCCACCCCCAAGTTCGGGTGAAGGCCCAGGGCTCGCAGCCAACGTCGGGGCGGCA

GGCCCTGCCATAGCTTTTTGGGGCGGCTTTT

The embodiments and examples presented herein are illustrative of the general nature of the subject matter claimed and are not limiting. It will be understood by those skilled in the art how these embodiments can be readily modified and/or adapted for various applications and in various ways without departing from the spirit and scope of the subject matter claimed. Phrases, words and terms employed herein are illustrative and are not limiting. Where permissible by law, all references cited herein are incorporated by reference in their entirety. It will be appreciated that any aspects of the different embodiments disclosed herein may be combined in a range of possible alternative embodiments, and alternative combinations of features, all of which varied combinations of features are to be understood to form a part of the subject matter claimed. Particular embodiments may alternatively comprise or consist of or exclude any one or more of the elements disclosed.

The embodiments of the invention in which an exclusive right or privilege is claimed are defined as follows:

1. A method of transforming a *Bifidobacteria* sp. bacterium with a DNA plasmid, the method comprising contacting the *Bifidobacteria* sp. bacterium with a hybrid protein in complex with the DNA plasmid, the hybrid protein comprising:

(i) at least one *Bifidobacteria* signal peptide selected from the group consisting of an alpha amylase signal peptide and an alpha arabinosidase signal peptide;

(ii) at least one DNA binding domain which binds to the DNA plasmid, the at least one DNA binding domain positioned C-terminal in the hybrid protein relative to the at least one *Bifidobacteria* signal peptide; and (iii) at least one cell penetrating peptide (CPP) domain positioned C-terminal in the hybrid protein relative to the at least one DNA binding domain.

2. The method of claim 1, wherein the at least one *Bifidobacteria* signal peptide is an alpha arabinosidase signal peptide.

3. The method of claim 1, wherein the at least one DNA binding domain is a sequence specific DNA binding domain and wherein the DNA plasmid comprises at least one nucleotide sequence which binds to said at least one sequence specific DNA binding domain.

4. The method of claim 1, wherein the at least one DNA binding domain comprises at least one domain selected from the group consisting of: a Zinc finger DNA binding domain, a homeobox DNA binding domain, a MerR DNA binding domain, and a HU DNA binding domain.

5. The method of claim 1, wherein the *Bifidobacteria* sp. bacterium is *Bifidobacterium longum*, wherein the at least one DNA binding domain comprises SEQ ID NO:44, 45, or 46, and wherein the at least one *Bifidobacteria* signal peptide comprises SEQ ID NO:19 or 23.

6. The method of claim 1, wherein the hybrid protein comprises the sequence set forth in SEQ ID NO:24.

7. The method of claim 6, wherein the *Bifidobacteria* sp. bacterium is *Bifidobacterium longum*.

8. The method of claim 3, wherein the at least one sequence specific DNA binding domain comprises the sequence set forth in SEQ ID NO:46, and the at least one nucleotide sequence which binds to the at least one sequence specific DNA binding domain comprises the sequence set forth in SEQ ID NO:43.

9. The method of claim 8, wherein the hybrid protein comprises the sequence set forth in SEQ ID NO:27.

10. The method of claim 9, wherein the *Bifidobacteria* sp. bacterium is *Bifidobacterium longum*.

* * * * *

SEQUENCE LISTING

```
<160> NUMBER OF SEQ ID NOS: 49

<210> SEQ ID NO 1
<211> LENGTH: 7176
<212> TYPE: DNA
<213> ORGANISM: Artificial Sequence
<220> FEATURE:
<223> OTHER INFORMATION: pBRA2.0 SHT wherein the eukaryotic expression
      cassette encodes GFP protein and the prokaryotic expression
      cassette encodes the SHT protein (synthetic pBRA2.0 SHT)

<400> SEQUENCE: 1
ccaggcccgt ggaggcgagg aagacggacg gcgacggcaa gggccattgg acgagcgtgg      60
cggggtatgg cgaggtgttc acgaccacgg agctgttcga cgtgacggcc gcgcgtgacc     120
acttcgacgg caccgtggag gccggggaat gccgtttctg cgcgtttgac gcgcgcaacc     180
gcgaacatca tgcgcggaac gccggaaggt tgttctagcg gccgtgtccg cgcctctggg     240
gcggttgcgc ctgccatgga gatctgggc cgagtcggcc gcgggcttcg agggaggcga     300
cgagagcaca tcgcccgcct caggcgacga gagcacatcg cccgcctcgg tcggccgcga     360
ggcgacgaga gcacatcgcc cgggccgagt cggccgcggg cttcgaggga ggtgggcgcg     420
gcggccatga agtggcttga caagcataat cttgtctgat tcgtctattt tcatacccc      480 ttcggggaaa tagatgtgaa aacccttata aaacgcgggt tttcgcagaa acatgcgcta     540
gtatcattga tgacaacatg gactaagcaa aagtgcttgt cccctgaccc aagaaggatg     600 cttttctcgag atgaccctga ccggcaccct gcgcaaagcg tttgcgacca ccctggcggc     660
ggcgatgctg attggcaccc tggcgggctg cagcagcgcg gcatacaaca agtctgacct     720
cgtttcgaag atcgcccaga agtccaacct gaccaaggct caggccgagg ctgctgttaa     780
cgccttccag gatgtgttcg tcgaggctat gaagtccggc gaaggcctga agctcaccgg     840
cctgttctcc gctgagcgcg tcaagcgccc ggctcgcacc ggccgcaacc cgcgcactgg     900
cgagcagatt gacattccgg cttcctacgg cgttcgtatc tccgctggct ccctgctgaa     960
gaaggccgtc accgagtatg gacggaagaa gcgcaggcag cgacggcgat gatctagact    1020
tctgctcgta gcgattactt cgagcattac tgacgacaaa gacccgacc gagatggtcg     1080 gggtcttttt gttgtggtgc tgtgacgtgt tgtccaaccg tattattccg gactagttca    1140
gcgaagcttc gacgagagca catcgcccgc ctcaggcgac gagagcacat cgcccgcctc    1200
ggtcggccgc gaggcgacga gagcgcctcg aagcttttt tttttggg cggcttttt      1260 ttttttaagct ttatctgctc cctgcttgtg tgttggaggt cgctgagtag tgcgcgagca    1320
aaatttaagc tacaacaagg caaggcttga ccgacaattg catgaagaat ctgcttaatt    1380
```

```
taagctacaa caaggcaagg cttgaccgac aattgcatga agaatctgct aggtactggc    1440
ttaactatgc ggcatcagag cagattgtac tgagagtgca ccatatgcgg tgtgaaatac    1500
cgcacagaat attattgaag catttatcag ggttattgtc tcatgagcgg atacatattt    1560
gaatgtattt agaaagcggc cgcgttaggc gttttcgcga tgtacgggcc agatatacgc    1620
gttgacattg attattgact agttattaat agtaatcaat tacggggtca ttagttcata    1680
gcccatatat ggagttccgc gttacataac ttacggtaaa tggcccgcct ggctgaccgc    1740
ccaacgaccc ccgcccattg acgtcaataa tgacgtatgt tcccatagta acgccaatag    1800
ggactttcca ttgacgtcaa tgggtggagt atttacggta aactgcccac ttggcagtac    1860
atcaagtgta tcatatgcca gtacgcccc ctattgacgt caatgacggt aaatggcccg    1920
cctggcatta tgcccagtac atgaccttat gggactttcc tacttggcag tacatctacg    1980
tattagtcat cgctattacc atggtgatgc ggttttggca gtacatcaat gggcgtggat    2040
agcggtttga ctcacgggga tttccaagtc tccaccccat tgacgtcaat gggagtttgt    2100
tttggcacca aaatcaacgg gactttccaa aatgtcgtaa caactccgcc ccattgacgc    2160
aaatgggcgg taggcgtgta cggtgggagg tctatataag cagagctcgt ttagtgaacc    2220
gtcagatcgc ctggagacgc catccacgct gttttgacct ccatagaaga caccgggacc    2280
gatccagcct ccggactcta gaggatcgaa gaattcgcca ccatggtgag caagggcgag    2340
gagctgttca ccggggtggt gcccatcctg gtcgagctgg acggcgacgt aaacggccac    2400
aagttcagcg tgtccggcga gggcgagggc gatgccacct acggcaagct gaccctgaag    2460
ttcatctgca ccaccggcaa gctgcccgtg ccctggccca ccctcgtgac caccctgacc    2520
tacggcgtgc agtgcttcag ccgctacccc gaccacatga gcagcacga cttcttcaag    2580 tccgccatgc ccgaaggcta cgtccaggag cgcaccatct tcttcaagga cgacggcaac    2640
tacaagaccc gcgccgaggt gaagttcgag ggcgacaccc tggtgaaccg catcgagctg    2700
aagggcatcg acttcaagga ggacggcaac atcctggggc acaagctgga gtacaactac    2760
aacagccaca acgtctatat catggccgac aagcagaaga acggcatcaa ggtgaacttc    2820
aagatccgcc acaacatcga ggacggcagc gtgcagctcg ccgaccacta ccagcagaac    2880
acccccatcg gcgacggccc cgtgctgctg cccgacaacc actacctgag cacccagtcc    2940
gccctgagca agaccccaa cgagaagcgc gatcacatgg tcctgctgga gttcgtgacc    3000
gccgccggga tcactctcgg catggacgag ctgtacaagt aggaattctt cgatccctac    3060
cggttagtaa tgagtttaaa cggggaggc taactgaaac acggaaggag acaataccgg    3120
aaggaacccg cgctatgacg gcaataaaaa gacagaataa aacgcacggg tgttgggtcg    3180
tttgttcata aacgcggggt tcggtcccag ggctggcact ctgtcgatac ccaccgaga    3240 ccccattggg gccaatacgc ccgcgtttct tccttttccc caccccaccc cccaagttcg    3300
ggtgaaggcc cagggctcgc agccaacgtc ggggcggcag gccctgccat agcgcggccg    3360
ctcgtaaagt ctggaaacgc ggaagtcagc gccctgcacc attatgttcc ggatctgcat    3420
cgcaggatgc tgctggctac cctgtggaac acctacatct gtattaacga agcgctggca    3480
ttgaccctga gtgattttc tctggtcccg ccgcatccat accgcagtt gtttaccctc    3540 acaacgttcc agtaaccggg catgttcatc atcagtaacc cgtatcgtga gcatgggatc    3600
catcatgcct cctctagacc agccaggaca gaaatgcctc gacttcgctg ctacccaagg    3660
ttgccgggtg acgcacaccg tggaaacgga tgaaggcacg aacccagtgg acataagcct    3720
```

```
gttcggttcg taagctgtaa tgcaagtagc gtatgcgctc acgcaactgg tccagaacct    3780
tgaccgaacg cagcggtggt aacggcgcag tggcggtttt catggcttgt tatgactgtt    3840
tttttggggt acagtctatg cctcgggcat ccaagcagca agcgcgttac gccgtgggtc    3900
gatgtttgat gttatggagc agcaacgatg ttacgcagca gggcagtcgc cctaaaacaa    3960
agttaaacat catgagggaa gcggtgatcg ccgaagtatc gactcaacta tcagaggtag    4020
ttggcgtcat cgagcgccat ctcgaaccga cgttgctggc cgtacatttg tacgctccg     4080 cagtggatgg cggcctgaag ccacacagtg atattgattt gctggttacg gtgaccgtaa    4140
ggcttgatga acaacgcggc gagctttga tcaacgacct tttggaaact tcggcttccc     4200
ctggagagag cgagattctc cgcgctgtag aagtcaccat tgttgtgcac gacgacatca    4260
ttccgtggcg ttatccagct aagcgcgaac tgcaatttgg agaatggcag cgcaatgaca    4320
ttcttgcagg tatcttcgag ccagccacga tcgacattga tctggctatc ttgctgacaa    4380
aagcaagaga acatagcgtt gccttggtag gtccagcggc ggaggaactc tttgatccgg    4440
ttcctgaaca ggatctattt gaggcgctaa atgaaacctt aacgctatgg aactcgccgc    4500
ccgactgggc tggcgatgag cgaaatgtag tgcttacgtt gtcccgcatt tggtacagcg    4560
cagtaaccgg caaaatcgcg ccgaaggatg tcgctgccga ctgggcaatg gagcgcctgc    4620
cggcccagta tcagcccgtc atacttgaag ctagacaggc ttatcttgga caagaagaag    4680
atcgcttggc ctcgcgcgca gatcagttgg aagaatttgt ccactacgtg aaaggcgaga    4740
tcaccaaggt agtcggcaaa taaccctcga gccacccatg accaaaatcc cttaacgtga    4800
gttacgcgtc gttccactga gcgtcagacc ccgtagaaaa gatcaaagga tcttcttgag    4860
atcctttttt tctgcgcgta atctgctgct tgcaaacaaa aaaaccaccg ctaccagcgg    4920
gatccatgca gctgcgtaag gagaaaatac cgcatcaggc gctcttccgc ttcctcgctc    4980
actgactcgc tgcgctcggt cgttcggctg cggcgagcgg tatcagctca ctcaaaggcg    5040
gtaatacggt tatccacaga acgtacgatg tgagcaaaag gccagcaaaa ggccagggac    5100
cgtaaaaagg ccgcgttgct ggcgtttttc cataggctcc gcccccctga cgagcatcac    5160
aaaaatcgac gctcaagtca gaggtggcga acccgacag gactataaag ataccaggcg     5220
tttccccctg gaagctccct cgtgcgctct cctgttccga ccctgccgct taccggatac    5280
ctgtccgcct ttctcccttc gggaagcgtg gcgctttctc atagctcacg ctgtaggtat    5340
ctcagttcgg tgtaggtcgt tcgctccaag ctgggctgtg tgcacgaacc ccccgttcag    5400
cccgaccgct gcgccttatc cggtaactat cgtcttgagt ccaacccggt aagacacgac    5460
ttatcgccac tggcagcagc cactggtaac aggattagca gagcgaggta tgtaggcggt    5520
gctacagagt tcttgaagtg gtggcctaac tacggctaca ctagaagaac agtatttggt    5580
atctgcgctc tgctgaagcc agttaccttc ggaaaaagag ttggtagctc ttgatccggc    5640
aaacaaacca ccgctggtag cggtggtttt tttgtttgca agcagcagat tacgcgcaga    5700
aaaaaaggat ctcaagaaga tcctttgatc ttttctacgg cgtacgtct tccttttca      5760 tcccggagac ggtcacagct tgtctgtaag cggatgccgg gagcagacaa gcccgtcagg    5820
gcgcgtcagc gggtgttggc gggtgtcggg gcgcagccat gacccagtca cgtagcgata    5880
gcggagtgta tactggctta actatgcggc atcagagcag attgtactga gagtgcacca    5940
tatgcggtgt gaaataccgc acagaatatt attgaagcat ttatcagggt tattgtctca    6000
tgagcggata catatttgaa tgtatttaga aaaataaaca ataggggtt ccgcgcacat     6060 ttccccgaaa agtgccacct gacgtctaag aaaccattat tatcatgaca ttaacctata    6120
```

-continued

```
aaaataggcg tatcacgagg cccttttcgtc ttcaagaaag atctccatgg gagaaccacg    6180
ggccggacgg ataccagccg ccctcatacg agccggtcaa ccccgaacgc aggaccgccc    6240
agacgccttc cgatggcctg atctgacgtc cgaaaaaagg cgccgtgcgc ccttttaaaa    6300
tcttttaaaa tcttttttaca ttcttttagg ccctccgcag ccctactctc caacggggtt    6360
tcggacggta cttagtacaa aaggggagcg aacttagtac aaaaggggag cgaacttagt    6420
acaaaagggg agcgaactta gtacaaaagg ggagcgaact agtaaataaa taaactttgt    6480
actagtatgg agtcatgtcc aatgagatcg tgaagttcag caaccagttc aacaacgtcg    6540
cgctgaagaa gttcgacgcc gtgcacctgg acgtgctcat ggcgatcgcc tcaagggtga    6600
gggagaaggg cacggccacg gtggagttct cgttcgagga gctgcgcggc ctcatgcgat    6660
tgaggaagaa cctgaccaac aagcagctgg cagacaagat cgtgcagacg aacgcgcgcc    6720
tgctggcgct gaactacatg ttcgaggatt cgggcaagat catccagttc gcgctgttca    6780
cgaagttcgt caccgacccg caggaggcga ctctcgcggt tggggtcaac gaggagttcg    6840 cttttcctgct caacgacctg accagccagt tcacgcgctt cgagctggcc gagttcgccg    6900
acctcaagag caagtacgcc aaggagttct acaggcgcgc caagcagtac cgcagctcgg    6960
gaatctggaa gatcagccgc gatgagttct gccgactgct tggcgtatcc gattccacgg    7020
caaaatccac cgccaacctg aacagggtcg tgctgaagac gatcgccgaa gagtgtgggc    7080
ctctccttgg cctgaagatc gagcgccagt acgtgaaacg caggctgtcg ggcttcgtgt    7140
tcacgttcgc ccgcgagacc cctccggtga tcgacg                              7176

<210> SEQ ID NO 2
<211> LENGTH: 5946
<212> TYPE: DNA
<213> ORGANISM: Artificial Sequence
<220> FEATURE:
<223> OTHER INFORMATION: pFRG1.5-SHT wherein the eukaryotic expression
      cassette comprises the green fluorescent protein (GFP) gene
      (synthetic pFRG1.5-SHT)

<400> SEQUENCE: 2
acgcgctgga gatgttcaac gagtagatcg ccacggcgac ctccttccac gcgtgcgggc      60
acggggattc tcaaggggcc ggcccgaggc cccttgagcc cgccgggagg cgccccggc     120 agggcgggaa tccaaagggc ggagccctgt ggccctcccc gggcaggggc gggatcgtca    180
agggcggagc ccttggcccc ctcgggagag cgcactgaca caatgctacc tccggtagca    240
ttaagtgcgc cctccgccat gcggagggac gggccgcgac cggatatgcg gggaacgtcc    300
acgacgcgtc ttccgtgtcc tccgtcctgc cttgtgccgt cgattataat cctcggataa    360
cggacgatga ttgaaccgat tggaggaaac gagatgccga agagtttcgc gcagcagatc    420
gaggacgacg agaacaagat caagcgcatc cgggagcacc agcgcatggt cagggccaaa    480
caagccaaac aggagcgcaa cgcccgcacc aaaaggctcg tggagaccgg agcgatagtg    540
gaaaaagcgc acggcggcgc gtacgacgac gaaggacggc agacgttctc ggatggtctg    600
aacggcatca tctcggtcta cgacccgtcc cgcggcggca acgtggacat gagagtcatc    660
gacgtaatcg accggcgcat ccccagattg ccaaggtccg aaaccacaac aggcacggca    720
gcggcggcat cgcgaaccgt gcaagccacc gcaccacagc cagcccacgc ccaaccgcaa    780
agcttcacgc ccaacccccca gcgcatcgaa caccggacag gagcacagca gccgatcgg    840 tgggcctagc cggacggcg cagccctcgc tccgctgggc tgaaatatct gacttggttc    900
```

```
gtaacatatt tccgacatgt cggaaatatg tcgtatcatc gttgctatga gtactgaact     960
tcgtgagcag tgggagcagc tttacctgcc gctgcgcccg ctgtgcacga acgacttcat    1020
cgagggcgtg taccggcagc ccagggcgaa ggcgctggag ggctaccggt acatcgaggc    1080
gaacccaag accgtcagcg acctgctcgt ggtcgacatc gacgacgcga acgcccgcgc     1140
gatggcccta tgggagcatg aggggatgct gcccaacgtg atcgtggaga acccgagaaa    1200
cggccacgcg cacgccgtgt gggcgctggc cgccccgttc agtcgcaccg aatacgcgcg    1260
gcgcaagccg ctcgccctgg ccgcggcggt cacggagggg ctgcgccgct cgtgcgacgg    1320
ggacaaggga tattcggggc tgatgaccaa gaacccgctg cacgaggcgt ggaacagcga    1380
actggtcacc gatcacctgt acgggctgga cgaactgcgc gaggcgctgg aggagtccgg    1440
ggacatgccg ccggcctcgt ggaagcgcac gaaacgcgcc aacgtggtcg gattgggccg    1500
caactgccat ctgttcgaga cggcgcgcac atgggcgtac agggaggtgc gccaccactg    1560
gggagacagc gaggggctgc ggctggccat ctcggccgag gcgcacgaaa tgaacgccga    1620
actgttcccc gagccactgg catggtcgga ggtcgagcag atcgccaaga gcatccacaa    1680
gtggatcgtc acccaaagcc gcatgtggcg cgacggcccc accgtctacg aggcgacatt    1740
catcaccgtc caaagcgccc gagggaaaaa gtcaggcaag gccagacgag aaacattcga    1800
actattcgcg agcgaggaga tgacgtaatg gttattcaaa cgttttggg gcggcttttg     1860
ggcccatgtg agcaaaaggc cagcaaaagg ccagggacce taaaaaggcc gcgttgctgg    1920
cgttttccca taggctccgc ccccctgacg agcatcacaa aaatcgacgc tcaagtcaga    1980
ggtggcgaaa cccgacagga ctataaagat accaggcgtt tccccctgga agctccctcg    2040
tgcgctctcc tgttccgacc ctgccgctta ccggatacct gtccgccttt ctcccttcgg    2100
gaagcgtggc gctttctcat agctcacgct gtaggtatct cagttcggtg taggtcgttc    2160
gctccaagct gggctgtgtg cacgaacccc ccgttcagcc cgaccgctgc gccttatccg    2220
gtaactatcg tcttgagtcc aacccggtaa gacacgactt atcgccactg gcagcagcca    2280
ctggtaacag gattagcaga gcgaggtatg taggcggtgc tacagagttc ttgaagtggt    2340
ggcctaacta cggctacact agaagaacag tatttggtat ctgcgctctg ctgaagccag    2400
ttaccttcgg aaaaagagtt ggtagctctt gatccggcaa acaaaccacc gctggtagcg    2460
gtggtttttt tgtttgcaag cagcagatta cgcgcagaaa aaaaggatct caagaagatc    2520
ctttgatctt ttctacgggt ttttttgggg cggctttgaa ttcttttttt tggggcggct    2580
tttttttat gcgctcacgc aactggtcca gaaccttgac cgaacgcagc ggtggtaacg     2640
gcgcagtggc ggttttcatg gcttgttatg actgttttt tggggtacag tctatgcctc     2700
gggcatccaa gcagcaagcg cgttacgccg tgggtcgatg tttgatgtta tggagcagca    2760
acgatgttac gcagcagggc agtcgcccta aaacaaagtt aaacatcatg agggaagcgg    2820
tgatcgccga agtatcgact caactatcag aggtagttgg cgtcatcgag cgccatctcg    2880
aaccgacgtt gctggccgta catttgtacg gctccgcagt ggatggcggc ctgaagccac    2940
acagtgatat tgatttgctg gttacggtga ccgtaaggct tgatgaaaca acgcggcgag    3000
ctttgatcaa cgacctttg gaaacttcgg cttccctgg agagagcgag attctccgcg     3060
ctgtagaagt caccattgtt gtgcacgacg acatcattcc gtggcgttat ccagctaagc    3120
gcgaactgca atttggagaa tggcagcgca atgacattct gcaggtatc ttcgagccag     3180
ccacgatcga cattgatctg gctatcttgc tgacaaaagc aagagaacat agcgttgcct    3240
tggtaggtcc agcggcggag gaactctttg atccggttcc tgaacaggat ctatttgagg    3300
```

```
cgctaaatga aaccttaacg ctatggaact cgccgcccga ctgggctggc gatgagcgaa    3360
atgtagtgct tacgttgtcc cgcatttggt acagcgcagt aaccggcaaa atcgcgccga    3420
aggatgtcgc tgccgactgg gcaatggagc gcctgccggc ccagtatcag cccgtcatac    3480
ttgaagctag acaggcttat cttgacaaga agaagatcg cttggcctcg cgcgcagatc     3540
agttggaaga atttgtccac tacgtgaaag gcgagatcac caaggtagtc ggcaaataag    3600
gtaccgttag gcgttttcgc gatgtacggg ccagatatac gcgttgacat tgattattga    3660
ctagttatta atagtaatca attacggggt cattagttca tagcccatat atggagttcc    3720
gcgttacata acttacggta atggcccgc ctggctgacc gcccaacgac ccccgcccat     3780
tgacgtcaat aatgacgtat gttcccatag taacgccaat agggactttc cattgacgtc    3840
aatgggtgga gtatttacgg taaactgccc acttggcagt acatcaagtg tatcatatgc    3900
caagtacgcc ccctattgac gtcaatgacg gtaaatggcc cgcctggcat tatgcccagt    3960
acatgacctt atgggacttt cctacttggc agtacatcta cgtattagtc atcgctatta    4020
ccatggtgat gcggttttgg cagtacatca atgggcgtgg atagcggttt gactcacggg    4080
gatttccaag tctccacccc attgacgtca atgggagttt gttttggcac caaaatcaac    4140
gggactttcc aaaatgtcgt aacaactccg ccccattgac gcaaatgggc ggtaggcgtg    4200
tacggtggga ggtctatata agcagagctc gtttagtgaa ccgtcagatc gcctggagac    4260
gccatccacg ctgttttgac ctccatagaa gacaccggga ccgatccagc ctccggactc    4320
tagaggatcg aagctagcca ccatggtgag caagggcgag gagctgttca ccggggtggt    4380
gcccatcctg gtcgagctgg acggcgacgt aaacggccac aagttcagcg tgtccggcga    4440
gggcgagggc gatgccacct acggcaagct gaccctgaag ttcatctgca ccaccggcaa    4500
gctgcccgtg ccctggccca ccctcgtgac caccctgacc tacggcgtgc agtgcttcag    4560
ccgctacccc gaccacatga gcagcacga cttcttcaag tccgccatgc ccgaaggcta    4620
cgtccaggag cgcaccatct tcttcaagga cgacggcaac tacaagaccc gcgccgaggt    4680
gaagttcgag ggcgacaccc tggtgaaccg catcgagctg aagggcatcg acttcaagga    4740
ggacggcaac atcctggggc acaagctgga gtacaactac aacagccaca acgtctatat    4800
catggccgac aagcagaaga acggcatcaa ggtgaacttc aagatccgcc acaacatcga    4860
ggacggcagc gtgcagctcg ccgaccacta ccagcagaac ccccatcg gcgacggccc     4920 cgtgctgctg cccgacaacc actacctgag cacccagtcc gccctgagca agacccccaa    4980
cgagaagcgc gatcacatgg tcctgctgga gttcgtgacc gccgccggga tcactctcgg    5040
catggacgag ctgtacaagt agatcttcga tccctaccgg ttagtaatga gtttaaacgg    5100
gggaggctaa ctgaaacacg gaaggagaca ataccggaag gaacccgcgc tatgacggca    5160
ataaaaagac agaataaaac gcacgggtgt tgggtcgttt gttcataaac gcggggttcg    5220
gtcccagggc tggcactctg tcgataccc accgagtccc cattgggcc aatacgcccg     5280 cgtttcttcc ttttccccac cccacccccc aagttcgggt gaaggcccag ggctcgcagc    5340
caacgtcggg gcggcaggcc ctgccatagc ttttggggc ggcttttctc gagtccttcc    5400
ttaaggacgt gctcgtcaat ttttgttttg agagtcatct attcggatgc ttttcatgaa    5460
gttttttatg accctgaccg gcaccctgcg caaggccttc gccaccaccc tggccgccgc    5520
catgctgatc ggcaccctgg ccggctgctc ctccgccgca taacaagt ctgacctcgt      5580 ttcgaagatc gcccagaagt ccaacctgac caaggctcag gccgaggctg ctgttaacgc    5640
```

```
cttccaggat gtgttcgtcg aggctatgaa gtccggcgaa ggcctgaagc tcaccggcct    5700
gttctccgct gagcgcgtca agcgcccggc tcgcaccggc cgcaacccgc gcactggcga    5760
gcagattgac attccggctt cctacggcgt tcgtatctcc gctggctccc tgctgaagaa    5820
ggccgtcacc gagtatggac ggaagaagcg caggcagcga cggcgatgag gaagaagcgc    5880
aggcagcgac ggcgatgagg gtttgcgctt cgtcgtgga gggagcggaa cgccgaaaaa    5940
ggatcc                                                              5946

<210> SEQ ID NO 3
<211> LENGTH: 189
<212> TYPE: DNA
<213> ORGANISM: Escherichia coli

<400> SEQUENCE: 3
aaatatgtaa cgttatacga tgtcgcagag tatgccggtg tctctcatca gaccgtttcc     60
cgcgtggtga accaggccag ccacgtttct gcgaaaacgc gggaaaaagt ggaagcggcg    120
atggcggagc tgaattacat tcccaaccgc gtggcacaac aactggcggg caaacagtcg    180
ttgctgatt                                                            189

<210> SEQ ID NO 4
<211> LENGTH: 276
<212> TYPE: DNA
<213> ORGANISM: Bifidobacterium longum

<400> SEQUENCE: 4
gcatacaaca agtctgacct cgtttcgaag atcgcccaga agtccaacct gaccaaggct     60
caggccgagg ctgctgttaa cgccttccag gatgtgttcg tcgaggctat gaagtccggc    120
gaaggcctga agctcaccgg cctgttctcc gctgagcgcg tcaagcgccc ggctcgcacc    180
ggccgcaacc cgcgcactgg cgagcagatt gacattccgg cttcctacgg cgttcgtatc    240
tccgctggct ccctgctgaa gaaggccgtc accgag                              276

<210> SEQ ID NO 5
<211> LENGTH: 429
<212> TYPE: DNA
<213> ORGANISM: Bifidobacterium longum

<400> SEQUENCE: 5
gaaaacaatt tggagaacct gaccattggc gttttcgcca ggacggccgg ggtcaatgtg     60
gagaccatcc ggttctatca gcgcaagggc ttgctcccgg aaccggacaa gccttacggc    120
agcattcgcc gctatggcga gacggatgta acgcgggtgc gcttcgtgaa atcagcccag    180
cggttgggct tcagcctgga tgagatcgcc gagctgctgc ggctggagga tggcacccat    240
tgcgaggaag ccagcagcct ggccgagcac aagctcaagg acgtgcgcga gaggatggct    300
gacctggcgc gcatggaggc cgtgctgtct gatttggtgt gcgcctgcca tgcgcgaagg    360
gggaacgttt cctgcccgct gatcgcgtca ctacagggtg agcaagcttt ggcaggttcg    420
gctatgcct                                                            429

<210> SEQ ID NO 6
<211> LENGTH: 294
<212> TYPE: DNA
<213> ORGANISM: Artificial Sequence
<220> FEATURE:
<223> OTHER INFORMATION: synthetic Zinc finger DNA binding domain

<400> SEQUENCE: 6
```

```
gaaaaactgc gcaacggcag cggcgatccg ggcaaaaaaa aacagcatgc gtgcccggaa    60
tgcggcaaaa gctttagcca gagcagcgat ctgcagcgcc atcagcgcac ccataccggc   120
gaaaaaccgt ataaatgccc ggaatgcggc aaaagcttta gccgcagcga tgaactgcag   180
cgccatcagc gcacccatac cggcgaaaaa ccgtataaat gcccggaatg cggcaaaagc   240
tttagccgca gcgatcatct gagccgccat cagcgcaccc atcagaacaa aaaa         294
```

```
<210> SEQ ID NO 7
<211> LENGTH: 555
<212> TYPE: DNA
<213> ORGANISM: Artificial Sequence
<220> FEATURE:
<223> OTHER INFORMATION: synthetic SMT hybrid protein

<400> SEQUENCE: 7
atgaccctga ccggcaccct gcgcaaagcg tttgcgacca ccctggcggc ggcgatgctg    60
attggcaccc tggcgggctg cagcagcgcg gaaaacaatt tggagaacct gaccattggc   120
gttttcgcca ggacggccgg ggtcaatgtg agaccatcc ggttctatca gcgcaagggc    180
ttgctcccgg aaccggacaa gccttacggc agcattcgcc gctatggcga gacggatgta   240
acgcgggtgc gcttcgtgaa atcagcccag cggttgggct tcagcctgga tgagatcgcc   300
gagctgctgc ggctggagga tgcaccccat tgcgaggaag ccagcagcct ggccgagcac   360
aagctcaagg acgtgcgcga gaggatggct gacctggcgc gcatggaggc cgtgctgtct   420
gatttggtgt gcgcctgcca tgcgcgaagg gggaacgttt cctgcccgct gatcgcgtca   480
ctacagggtg gagcaagctt ggcaggttcg gctatgcctt atggacggaa gaagcgcagg   540
cagcgacggc gatga                                                    555
```

```
<210> SEQ ID NO 8
<211> LENGTH: 402
<212> TYPE: DNA
<213> ORGANISM: Artificial Sequence
<220> FEATURE:
<223> OTHER INFORMATION: synthetic SHT hybrid protein

<400> SEQUENCE: 8
atgaccctga ccggcaccct gcgcaaagcg tttgcgacca ccctggcggc ggcgatgctg    60
attggcaccc tggcgggctg cagcagcgcg gcatacaaca agtctgacct cgtttcgaag   120
atcgcccaga agtccaacct gaccaaggct caggccgagg ctgctgttaa cgccttccag   180
gatgtgttcg tcgaggctat gaagtccggc gaaggcctga agctcaccgg cctgttctcc   240
gctgagcgcg tcaagcgccc ggctcgcacc ggccgcaacc gcgcactgg cgagcagatt   300 gacattccgg cttcctacgg cgttcgtatc tccgctggct ccctgctgaa gaaggccgtc   360
accgagtatg gacggaagaa gcgcaggcag cgacggcgat ga                      402
```

```
<210> SEQ ID NO 9
<211> LENGTH: 315
<212> TYPE: DNA
<213> ORGANISM: Artificial Sequence
<220> FEATURE:
<223> OTHER INFORMATION: synthetic SLT hybrid protein

<400> SEQUENCE: 9
atgaccctga ccggcaccct gcgcaaagcg tttgcgacca ccctggcggc ggcgatgctg    60
attggcaccc tggcgggctg cagcagcgcg aaatatgtaa cgttatacga tgtcgcagag   120
```

-continued

```
tatgccggtg tctctcatca gaccgtttcc cgcgtggtga accaggccag ccacgtttct    180
gcgaaaacgc gggaaaaagt ggaagcggcg atggcggagc tgaattacat tcccaaccgc    240
gtggcacaac aactggcggg caaacagtcg ttgctgattt atggacggaa gaagcgcagg    300
cagcgacggc gatga                                                    315
```

<210> SEQ ID NO 10
<211> LENGTH: 420
<212> TYPE: DNA
<213> ORGANISM: Artificial Sequence
<220> FEATURE:
<223> OTHER INFORMATION: synthetic SZT hybrid protein

<400> SEQUENCE: 10

```
atgaccctga ccggcaccct gcgcaaagcg tttgcgacca ccctggcggc ggcgatgctg     60
attggcaccc tggcgggctg cagcagcgcg gaaaaactgc gcaacggcag cggcgatccg    120
ggcaaaaaaa aacagcatgc cgtgcccgaa tgcggcaaaa gctttagcca gagcagcgat    180
ctgcagcgcc atcagcgcac ccataccggc gaaaaaccgt ataaatgccc ggaatgcggc    240
aaaagcttta gccgcagcga tgaactgcag cgccatcagc gcacccatac cggcgaaaaa    300
ccgtataaat gccggaatg cggcaaaagc tttagccgca gcgatcatct gagccgccat    360
cagcgcaccc atcagaacaa aaaatatgga cggaagaagc gcaggcagcg acggcgatga    420
```

<210> SEQ ID NO 11
<211> LENGTH: 11
<212> TYPE: PRT
<213> ORGANISM: Human immunodeficiency virus

<400> SEQUENCE: 11

Tyr Gly Arg Lys Lys Arg Arg Gln Arg Arg
1               5                   10

<210> SEQ ID NO 12
<211> LENGTH: 16
<212> TYPE: PRT
<213> ORGANISM: Drosophila melanogaster

<400> SEQUENCE: 12

Arg Gln Ile Lys Ile Trp Phe Gln Asn Arg Arg Met Lys Trp Lys Lys
1               5                   10                  15

<210> SEQ ID NO 13
<211> LENGTH: 17
<212> TYPE: PRT
<213> ORGANISM: Human immunodeficiency virus

<400> SEQUENCE: 13

Thr Arg Gln Ala Arg Arg Asn Arg Arg Arg Arg Trp Arg Glu Arg Gln
1               5                   10                  15

Phe

<210> SEQ ID NO 14
<211> LENGTH: 17
<212> TYPE: PRT
<213> ORGANISM: Human immunodeficiency virus

<400> SEQUENCE: 14

Asn Ala Lys Thr Arg Arg His Glu Arg Arg Arg Lys Leu Ala Ile Glu
1               5                   10                  15

Arg

<210> SEQ ID NO 15
<211> LENGTH: 30
<212> TYPE: PRT
<213> ORGANISM: Simian virus 40

<400> SEQUENCE: 15

Gly Ala Leu Phe Leu Gly Phe Leu Gly Ala Ala Gly Ser Thr Met Gly
1               5                   10                  15

Ala Trp Ser Gln Pro Lys Lys Arg Lys Val Cys Tyr Ser
            20                  25                  30

<210> SEQ ID NO 16
<211> LENGTH: 27
<212> TYPE: PRT
<213> ORGANISM: Unknown
<220> FEATURE:
<223> OTHER INFORMATION: Transportan (Galanin-mastoparan)

<400> SEQUENCE: 16

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 17
<211> LENGTH: 21
<212> TYPE: PRT
<213> ORGANISM: Simian virus 40

<400> SEQUENCE: 17

Lys Glu Thr Trp Trp Glu Thr Trp Trp Thr Glu Trp Ser Gln Pro Lys
1               5                   10                  15

Lys Lys Arg Arg Val
            20

<210> SEQ ID NO 18
<211> LENGTH: 138
<212> TYPE: DNA
<213> ORGANISM: Bifidobacterium longum

<400> SEQUENCE: 18
atgaaacatc ggaaacccgc accggcctgg cataggctgg ggctgaagat tagcaagaaa      60
gtggtggtcg gcatcaccgc cgcggcgacc gccttcggcg gactggcaat cgccagcacc     120
gcagcacagg ccagcacc                                                   138

<210> SEQ ID NO 19
<211> LENGTH: 46
<212> TYPE: PRT
<213> ORGANISM: Bifidobacterium longum

<400> SEQUENCE: 19

Met Lys His Arg Lys Pro Ala Pro Ala Trp His Arg Leu Gly Leu Lys
1               5                   10                  15

Ile Ser Lys Lys Val Val Val Gly Ile Thr Ala Ala Ala Thr Ala Phe
            20                  25                  30

Gly Gly Leu Ala Ile Ala Ser Thr Ala Ala Gln Ala Ser Thr
        35                  40                  45

<210> SEQ ID NO 20
<211> LENGTH: 132

<212> TYPE: DNA
<213> ORGANISM: Bifidobacterium longum

<400> SEQUENCE: 20

```
atgaaacatc ggaaaccgc accggcctgg cataggctgg ggctgaagat tagcaagaaa      60
gtggtggtcg gcatcaccgc cgcggcgacc gccttcggcg gactggcaat cgccagcacc    120
gcagcacagg cc                                                        132
```

<210> SEQ ID NO 21
<211> LENGTH: 44
<212> TYPE: PRT
<213> ORGANISM: Bifidobacterium longum

<400> SEQUENCE: 21

Met Lys His Arg Lys Pro Ala Pro Ala Trp His Arg Leu Gly Leu Lys
1               5                   10                  15

Ile Ser Lys Lys Val Val Gly Ile Thr Ala Ala Ala Thr Ala Phe
            20                  25                  30

Gly Gly Leu Ala Ile Ala Ser Thr Ala Ala Gln Ala
        35                  40

<210> SEQ ID NO 22
<211> LENGTH: 87
<212> TYPE: DNA
<213> ORGANISM: Bifidobacterium animalis

<400> SEQUENCE: 22

```
accctgaccg gcaccctgcg caaagcgttt gcgaccaccc tggcggcggc gatgctgatt      60
ggcaccctgg cgggctgcag cagcgcg                                         87
```

<210> SEQ ID NO 23
<211> LENGTH: 29
<212> TYPE: PRT
<213> ORGANISM: Bifidobacterium animalis

<400> SEQUENCE: 23

Thr Leu Thr Gly Thr Leu Arg Lys Ala Phe Ala Thr Thr Leu Ala Ala
1               5                   10                  15

Ala Met Leu Ile Gly Thr Leu Ala Gly Cys Ser Ser Ala
            20                  25

<210> SEQ ID NO 24
<211> LENGTH: 133
<212> TYPE: PRT
<213> ORGANISM: Artificial Sequence
<220> FEATURE:
<223> OTHER INFORMATION: synthetic SHT HYBRID PROTEIN

<400> SEQUENCE: 24

Met Thr Leu Thr Gly Thr Leu Arg Lys Ala Phe Ala Thr Thr Leu Ala
1               5                   10                  15

Ala Ala Met Leu Ile Gly Thr Leu Ala Gly Cys Ser Ser Ala Ala Tyr
            20                  25                  30

Asn Lys Ser Asp Leu Val Ser Lys Ile Ala Gln Lys Ser Asn Leu Thr
        35                  40                  45

Lys Ala Gln Ala Glu Ala Ala Val Asn Ala Phe Gln Asp Val Phe Val
    50                  55                  60

Glu Ala Met Lys Ser Gly Glu Gly Leu Lys Leu Thr Gly Leu Phe Ser
65                  70                  75                  80

```
Ala Glu Arg Val Lys Arg Pro Ala Arg Thr Gly Arg Asn Pro Arg Thr
                85                  90                  95

Gly Glu Gln Ile Asp Ile Pro Ala Ser Tyr Gly Val Arg Ile Ser Ala
            100                 105                 110

Gly Ser Leu Leu Lys Lys Ala Val Thr Glu Tyr Gly Arg Lys Lys Arg
        115                 120                 125

Arg Gln Arg Arg Arg
    130

<210> SEQ ID NO 25
<211> LENGTH: 104
<212> TYPE: PRT
<213> ORGANISM: Artificial Sequence
<220> FEATURE:
<223> OTHER INFORMATION: synthetic SLT HYBRID PROTEIN

<400> SEQUENCE: 25

Met Thr Leu Thr Gly Thr Leu Arg Lys Ala Phe Ala Thr Thr Leu Ala
1               5                   10                  15

Ala Ala Met Leu Ile Gly Thr Leu Ala Gly Cys Ser Ser Ala Lys Tyr
            20                  25                  30

Val Thr Leu Tyr As

Ala Cys His Ala Arg Arg Gly Asn Val Ser Cys Pro Leu Ile Ala Ser
145                 150                 155                 160

Leu Gln Gly Gly Ala Ser Leu Ala Gly Ser Ala Met Pro Tyr Gly Arg
                165                 170                 175

Lys Lys Arg Arg Gln Arg Arg
            180

<210> SEQ ID NO 27
<211> LENGTH: 139
<212> TYPE: PRT
<213> ORGANISM: Artificial Sequence
<220> FEATURE:
<223> OTHER INFORMATION: synthetic SZT HYBRID PROTEIN

<400> SEQUENCE: 27

Met Thr Leu Thr Gly Thr Leu Arg Lys Ala Phe Ala Thr Leu Ala
1               5                   10                  15

Ala Ala Met Leu Ile Gly Thr Leu Ala Gly Cys Ser Ser Ala Glu Lys
                20                  25                  30

Leu Arg Asn Gly Ser Gly Asp Pro Gly Lys Lys Gln His Ala Cys
            35                  40                  45

Pro Glu Cys Gly Lys Ser Phe Ser Gln Ser Ser Asp Leu Gln Arg His
        50                  55                  60

Gln Arg Thr His Thr Gly Glu Lys Pro Tyr Lys Cys Pro Glu Cys Gly
65                  70                  75                  80

Lys Ser Phe Ser Arg Ser Asp Glu Leu Gln Arg His Gln Arg Thr His
                85                  90                  95

Thr Gly Glu Lys Pro Tyr Lys Cys Pro Glu Cys Gly Lys Ser Phe Ser
                100                 105                 110

Arg Ser Asp His Leu Ser Arg His Gln Arg Thr His Gln Asn Lys Lys
            115                 120                 125

Tyr Gly Arg Lys Lys Arg Arg Gln Arg Arg
        130                 135

<210> SEQ ID NO 28
<211> LENGTH: 1828
<212> TYPE: DNA
<213> ORGANISM: Bifidobacterium longum

<400> SEQUENCE: 28
acgcgctgga gatgttcaac gagtagatcg ccacggcgac ctccttccac gcgtgcgggc      60
acggggattc tcaaggggcc ggcccgaggc cccttgagcc cgccgggagg cgccccggc     120
agggcgggaa tccaaagggc ggagccctgt ggccctcccc gggcaggggc gggatcgtca    180
agggcggagc ccttggcccc tcgggagag cgcactgaca caatgctacc tccggtagca     240
ttaagtgcgc cctccgccat gcggagggac gggccgcgac cggatatgcg gggaacgtcc    300
acgacgcgtc ttccgtgtcc tccgtcctgc cttgtgccgt cgattataat cctcggataa    360
cggacgatga ttgaaccgat tggaggaaac gagatgccga agagtttcgc gcagcagatc    420
gaggacgacg agaacaagat caagcgcatc cgggagcacc agcgcatggt cagggccaaa    480
caagccaaac aggagcgcaa cgcccgcacc aaaaggctcg tggagaccgg agcgatagtg    540
gaaaaagcgc acggcggcgc gtacgacgac gaaggacggc agacgttctc ggatggtctg    600
aacggcatca tctcggtcta cgacccgtcc cgcggcggca acgtggacat gagagtcatc    660
gacgtaatcg accggcgcat ccccagattg ccaaggtccg aaaccacaac aggcacggca    720

| | |
|---|---|
| gcggcggcat cgcgaaccgt gcaagccacc gcaccacagc cagcccacgc ccaaccgcaa | 780 |
| agcttcacgc ccaaccccca gcgcatcgaa caccggacag gagcacagca gccggatcgg | 840 |
| tgggcctagc cgggacggcg cagccctcgc tccgctgggc tgaaatatct gacttggttc | 900 |
| gtaacatatt tccgacatgt cggaaatatg tcgtatcatc gttgctatga gtactgaact | 960 |
| tcgtgagcag tgggagcagc tttacctgcc gctgcgcccg ctgtgcacga acgacttcat | 1020 |
| cgagggcgtg taccggcagc ccagggcgaa ggcgctggag ggctaccggt acatcgaggc | 1080 |
| gaaccccaag accgtcagcg acctgctcgt ggtcgacatc gacgacgcga acgcccgcgc | 1140 |
| gatggcccta tgggagcatg aggggatgct gcccaacgtg atcgtggaga acccgagaaa | 1200 |
| cggccacgcg cacgccgtgt gggcgctggc cgccccgttc agtcgcaccg aatacgcgcg | 1260 |
| gcgcaagccg ctcgccctgg ccgcggcggt cacggagggg ctgcgccgct cgtgcgacgg | 1320 |
| ggacaaggga tattcggggc tgatgaccaa gaacccgctg cacgaggcgt ggaacagcga | 1380 |
| actggtcacc gatcacctgt acgggctgga cgaactgcgc gaggcgctgg aggagtccgg | 1440 |
| ggacatgccg ccggcctcgt ggaagcgcac gaaacggcgc aacgtggtcg gattgggccg | 1500 |
| caactgccat ctgttcgaga cggcgcgcac atgggcgtac agggaggtgc gccaccactg | 1560 |
| gggagacagc gaggggctgc ggctggccat ctcggccgag gcgcacgaaa tgaacgccga | 1620 |
| actgttcccc gagccactgg catggtcgga ggtcgagcag atcgccaaga gcatccacaa | 1680 |
| gtggatcgtc acccaaagcc gcatgtggcg cgacggcccc accgtctacg aggcgacatt | 1740 |
| catcaccgtc caaagcgccc gagggaaaaa gtcaggcaag gccagacgag aaacattcga | 1800 |
| actattcgcg agcgaggaga tgacgtaa | 1828 |

<210> SEQ ID NO 29
<211> LENGTH: 692
<212> TYPE: DNA
<213> ORGANISM: Escherichia coli

<400> SEQUENCE: 29

| | |
|---|---|
| atgtgagcaa aaggccagca aaaggccagg gaccgtaaaa aggccgcgtt gctggcgttt | 60 |
| ttccataggc tccgcccccc tgacgagcat cacaaaaatc gacgctcaag tcagaggtgg | 120 |
| cgaaacccga caggactata aagataccag gcgtttcccc ctggaagctc cctcgtgcgc | 180 |
| tctcctgttc cgaccctgcc gcttaccgga tacctgtccg cctttctccc ttcgggaagc | 240 |
| gtggcgcttt ctcatagctc acgctgtagg tatctcagtt cggtgtaggt cgttcgctcc | 300 |
| aagctgggct gtgtgcacga accccccgtt cagcccgacc gctgcgcctt atccggtaac | 360 |
| tatcgtcttg agtccaaccc ggtaagacac gacttatcgc cactggcagc agccactggt | 420 |
| aacaggatta gcagagcgag gtatgtaggc ggtgctacag agttcttgaa gtggtggcct | 480 |
| aactacggct acactagaag aacagtattt ggtatctgcg ctctgctgaa gccagttacc | 540 |
| ttcggaaaaa gagttggtag ctcttgatcc ggcaaacaaa ccaccgctgg tagcggtggt | 600 |
| ttttttgttt gcaagcagca gattacgcgc agaaaaaaag gatctcaaga agatcctttg | 660 |
| atcttttcta cgggtttttt tggggcggct tt | 692 |

<210> SEQ ID NO 30
<211> LENGTH: 1241
<212> TYPE: DNA
<213> ORGANISM: Bifidobacterium longum

<400> SEQUENCE: 30

| | |
|---|---|
| ccctcatacg agccggtcaa ccccgaacgc aggaccgccc agacgccttc cgatggcctg | 60 |

```
atctgacgtc cgaaaaaagg cgccgtgcgc ccttttaaaa tcttttaaaa tcttttaca    120 ttcttttagg ccctccgcag ccctactctc caacgggtt tcggacggta cttagtacaa    180
aaggggagcg aacttagtac aaaaggggag cgaacttagt acaaaagggg agcgaactta    240
gtacaaaagg ggagcgaact agtaaataaa taaactttgt actagtatgg agtcatgtcc    300
aatgagatcg tgaagttcag caaccagttc aacaacgtcg cgctgaagaa gttcgacgcc    360
gtgcacctgg acgtgctcat ggcgatcgcc tcaaggtgga gggagaaggg cacggccacg    420
gtggagttct cgttcgagga gctgcgcggc ctcatgcgat tgaggaagaa cctgaccaac    480
aagcagctgg cagacaagat cgtgcagacg aacgcgcgcc tgctggcgct gaactacatg    540
ttcgaggatt cgggcaagat catccagttc gcgctgttca cgaagttcgt caccgacccg    600
caggaggcga ctctcgcggt tggggtcaac gaggagttcg ctttcctgct caacgacctg    660
accagccagt tcacgcgctt cgagctggcc gagttcgccg acctcaagag caagtacgcc    720
aaggagttct acaggcgcgc caagcagtac cgcagctcgg gaatctggaa gatcagccgc    780
gatgagttct gccgactgct tggcgtatcc gattccacgg caaaatccac cgccaacctg    840
aacagggtcg tgctgaagac gatcgccgaa gagtgtgggc ctctccttgg cctgaagatc    900
gagcgccagt acgtgaaacg caggctgtcg ggcttcgtgt tcacgttcgc ccgcgagacc    960
cctccggtga tcgacgccag gcccgtggag gcgaggaaga cggacggcga cggcaagggc   1020
cattggacga gcgtggcggg gtatggcgag gtgttcacga ccacggagct gttcgacgtg   1080
acggccgcgc gtgaccactt cgacggcacc gtggaggccg gggaatgccg tttctgcgcg   1140
tttgacgcgc gcaaccgcga acatcatgcg cggaacgccg gaaggttgtt ctagcggccg   1200
tgtccgcgcc tctggggcgg ttgcgcctgc catggagatc t                       1241

<210> SEQ ID NO 31
<211> LENGTH: 33
<212> TYPE: DNA
<213> ORGANISM: Human immunodeficiency virus

<400> SEQUENCE: 31
tatggacgga agaagcgcag gcagcgacgg cga                                 33

<210> SEQ ID NO 32
<211> LENGTH: 81
<212> TYPE: DNA
<213> ORGANISM: Simian virus 40

<400> SEQUENCE: 32
ggcgcgctgt ttctgggctt tctgggcgcg gcgggcagca ccatgggcgc gtggagccag    60
ccgaaaaaaa aacgcaaagt g                                              81

<210> SEQ ID NO 33
<211> LENGTH: 81
<212> TYPE: DNA
<213> ORGANISM: Unknown
<220> FEATURE:
<223> OTHER INFORMATION: Transportan (Galanin-mastoparan)

<400> SEQUENCE: 33
ggctggaccc tgaacagcgc gggctatctg ctgggcaaaa ttaacctgaa agcgctggcg    60
gcgctggcga aaaaaattct g                                              81

<210> SEQ ID NO 34
```

```
<211> LENGTH: 63
<212> TYPE: DNA
<213> ORGANISM: Simian virus 40

<400> SEQUENCE: 34
aaagaaacct ggtgggaaac ctggtggacc gaatggagcc agccgaaaaa aaaacgccgc    60
gtg                                                                  63

<210> SEQ ID NO 35
<211> LENGTH: 26
<212> TYPE: DNA
<213> ORGANISM: Aequorea victoria

<400> SEQUENCE: 35
gaattcgcca ccatggtgag caaggg                                          26

<210> SEQ ID NO 36
<211> LENGTH: 26
<212> TYPE: DNA
<213> ORGANISM: Aequorea victoria

<400> SEQUENCE: 36
tggacgagct gtacaagtag gaattc                                          26

<210> SEQ ID NO 37
<211> LENGTH: 29
<212> TYPE: DNA
<213> ORGANISM: Streptomyces spectabilis

<400> SEQUENCE: 37
atgcgctcac gcaactggtc cagaacctt                                       29

<210> SEQ ID NO 38
<211> LENGTH: 29
<212> TYPE: DNA
<213> ORGANISM: Streptomyces spectabilis

<400> SEQUENCE: 38
ttatttgccg actaccttgg tgatctcgc                                       29

<210> SEQ ID NO 39
<211> LENGTH: 32
<212> TYPE: DNA
<213> ORGANISM: Cytomegalovirus

<400> SEQUENCE: 39
gttaggcgtt ttcgcgatgt acgggccaga ta                                   32

<210> SEQ ID NO 40
<211> LENGTH: 33
<212> TYPE: DNA
<213> ORGANISM: Cytomegalovirus

<400> SEQUENCE: 40
gtggcgaatt cttcgatcct ctagagtccg gag                                  33

<210> SEQ ID NO 41
<211> LENGTH: 84
<212> TYPE: DNA
<213> ORGANISM: Bifidobacterium longum

<400> SEQUENCE: 41
aagcttgtcg acctgcagcc ttggcgcttg actccgtaca tgagtacgga agtaaggtta    60
```

```
cgctatcctt ggctgcagaa gctt                                              84
```

<210> SEQ ID NO 42
<211> LENGTH: 120
<212> TYPE: DNA
<213> ORGANISM: Escherichia coli

<400> SEQUENCE: 42

```
aagcttcagt gagcgcaacg caattaatgt gagttagctc actcattagg cacccccaggc    60 tttacacttt atgcttccgg ctcgtatgtt gtgtggaatt gtgagcgctc acaaaagctt   120
```

<210> SEQ ID NO 43
<211> LENGTH: 41
<212> TYPE: DNA
<213> ORGANISM: Artificial Sequence
<220> FEATURE:
<223> OTHER INFORMATION: Synthetic zinc finger DNA recognition site

<400> SEQUENCE: 43

```
aagctttttt tttttggggg cggcttttttt tttttaagct t                        41
```

<210> SEQ ID NO 44
<211> LENGTH: 92
<212> TYPE: PRT
<213> ORGANISM: Bifidobacterium longum

<400> SEQUENCE: 44

```
Ala Tyr Asn Lys Ser Asp Leu Val Ser Lys Ile Ala Gln Lys Ser Asn
1               5                   10                  15

Leu Thr Lys Ala Gln Ala Glu Ala Ala Val Asn Ala Phe Gln Asp Val
            20                  25                  30

Phe Val Glu Ala Met Lys Ser Gly Glu Gly Leu Lys Leu Thr Gly Leu
        35                  40                  45

Phe Ser Ala Glu Arg Val Lys Arg Pro Ala Arg Thr Gly Arg Asn Pro
    50                  55                  60

Arg Thr Gly Glu Gln Ile Asp Ile Pro Ala Ser Tyr Gly Val Arg Ile
65                  70                  75                  80

Ser Ala Gly Ser Leu Leu Lys Lys Ala Val Thr Glu
                85                  90
```

<210> SEQ ID NO 45
<211> LENGTH: 144
<212> TYPE: PRT
<213> ORGANISM: Bifidobacterium longum

<400> SEQUENCE: 45

```
Met Glu Asn Asn Leu Glu Asn Leu Thr Ile Gly Val Phe Ala Arg Thr
1               5                   10                  15

Ala Gly Val Asn Val Glu Thr Ile Arg Phe Tyr Gln Arg Lys Gly Leu
            20                  25                  30

Leu Pro Glu Pro Asp Lys Pro Tyr Gly Ser Ile Arg Arg Tyr Gly Glu
        35                  40                  45

Thr Asp Val Thr Arg Val Arg Phe Val Lys Ser Ala Gln Arg Leu Gly
    50                  55                  60

Phe Ser Leu Asp Glu Ile Ala Glu Leu Leu Arg Leu Glu Asp Gly Thr
65                  70                  75                  80

His Cys Glu Glu Ala Ser Ser Leu Ala Glu His Lys Leu Lys Asp Val
                85                  90                  95
```

```
Arg Glu Arg Met Ala Asp Leu Ala Arg Met Glu Ala Val Leu Ser Asp
                100                 105                 110

Leu Val Cys Ala Cys His Ala Arg Arg Gly Asn Val Ser Cys Pro Leu
        115                 120                 125

Ile Ala Ser Leu Gln Gly Gly Ala Ser Leu Ala Gly Ser Ala Met Pro
    130                 135                 140

<210> SEQ ID NO 46
<211> LENGTH: 99
<212> TYPE: PRT
<213> ORGANISM: Artificial Sequence
<220> FEATURE:
<223> OTHER INFORMATION: synthetic Zn finger DNA binding domain

<400> SEQUENCE: 46

Met Glu Lys Leu Arg Asn Gly Ser Gly Asp Pro Gly Lys Lys Lys Gln
1               5                   10                  15

His Ala Cys Pro Glu Cys Gly Lys Ser Phe Ser Gln Ser Ser Asp Leu
            20                  25                  30

Gln Arg His Gln Arg Thr His Thr Gly Glu Lys Pro Tyr Lys Cys Pro
        35                  40                  45

Glu Cys Gly Lys Ser Phe Ser Arg Ser Asp Glu Leu Gln Arg His Gln
    50                  55                  60

Arg Thr His Thr Gly Glu Lys Pro Tyr Lys Cys Pro Glu Cys Gly Lys
65                  70                  75                  80

Ser Phe Ser Arg Ser Asp His Leu Ser Arg His Gln Arg Thr His Gln
                85                  90                  95

Asn Lys Lys

<210> SEQ ID NO 47
<211> LENGTH: 64
<212> TYPE: PRT
<213> ORGANISM: Escherichia coli

<400> SEQUENCE: 47

Met Lys Tyr Val Thr Leu Tyr Asp Val Ala Glu Tyr Ala Gly Val Ser
1               5                   10                  15

His Gln Thr Val Ser Arg Val Val Asn Gln Ala Ser His Val Ser Ala
            20                  25                  30

Lys Thr Arg Glu Lys Val Glu Ala Ala Met Ala Glu Leu Asn Tyr Ile
        35                  40                  45

Pro Asn Arg Val Ala Gln Gln Leu Ala Gly Lys Gln Ser Leu Leu Ile
    50                  55                  60

<210> SEQ ID NO 48
<211> LENGTH: 121
<212> TYPE: DNA
<213> ORGANISM: Artificial Sequence
<220> FEATURE:
<223> OTHER INFORMATION: synthetic prokaryotic expression cassette
      comprising Hu Promoter and terminator

<400> SEQUENCE: 48
tccttcctta aggacgtgct cgtcaatttt tgttttgaga gtcatctatt cggatgcttt      60
tcatgaagtt ttttggaaga agcgcaggca gcgacggcga tgagggtttg cgcttgcgtc    120
g                                                                    121

<210> SEQ ID NO 49
<211> LENGTH: 1783
```

<212> TYPE: DNA
<213> ORGANISM: Artificial Sequence
<220> FEATURE:
<223> OTHER INFORMATION: Eukaryotic Expression Cassette comprising CMV
      promoter, Kozak sequence and TK Poly A site and terminator,
      flanking GFP coding sequences to be expressed (synthetic
      Expression Cassette)

<400> SEQUENCE: 49

```
ggttaggcgt tttcgcgatg tacgggccag atatacgcgt tgacattgat tattgactag      60
ttattaatag taatcaatta cggggtcatt agttcatagc ccatatatgg agttccgcgt     120
tacataactt acggtaaatg gcccgcctgg ctgaccgccc aacgaccccc gcccattgac     180
gtcaataatg acgtatgttc ccatagtaac gccaataggg actttccatt gacgtcaatg     240
ggtggagtat ttacggtaaa ctgcccactt ggcagtacat caagtgtatc atatgccaag     300 tacgcccct attgacgtca atgacggtaa atggcccgcc tggcattatg cccagtacat     360
gaccttatgg gactttccta cttggcagta catctacgta ttagtcatcg ctattaccat     420
ggtgatgcgg ttttggcagt acatcaatgg gcgtggatag cggtttgact cacgggatt     480 tccaagtctc cacccattg acgtcaatgg gagtttgttt tggcaccaaa atcaacggga     540
ctttccaaaa tgtcgtaaca actccgcccc attgacgcaa atgggcggta ggcgtgtacg     600
gtgggaggtc tatataagca gagctcgttt agtgaaccgt cagatcgcct ggagacgcca     660
tccacgctgt tttgacctcc atagaagaca ccgggaccga tccagcctcc ggactctaga     720
ggatcgaagc tagccaccat ggtgagcaag ggcgaggagc tgttcaccgg ggtggtgccc     780
atcctggtcg agctggacgg cgacgtaaac ggccacaagt tcagcgtgtc cggcgagggc     840
gagggcgatg ccacctacgg caagctgacc ctgaagttca tctgcaccac cggcaagctg     900
cccgtgccct ggcccaccct cgtgaccacc ctgacctacg gcgtgcagtg cttcagccgc     960
taccccgacc acatgaagca gcacgacttc ttcaagtccg ccatgcccga aggctacgtc    1020
caggagcgca ccatcttctt caaggacgac ggcaactaca agacccgcgc cgaggtgaag    1080
ttcgagggcg acaccctggt gaaccgcatc gagctgaagg gcatcgactt caaggaggac    1140
ggcaacatcc tggggcacaa gctggagtac aactacaaca gccacaacgt ctatatcatg    1200
gccgacaagc agaagaacgg catcaaggtg aacttcaaga tccgccacaa catcgaggac    1260
ggcagcgtgc agctcgccga ccactaccag cagaacaccc ccatcggcga cggccccgtg    1320
ctgctgcccg acaaccacta cctgagcacc cagtccgccc tgagcaaaga ccccaacgag    1380
aagcgcgatc acatggtcct gctggagttc gtgaccgccg ccgggatcac tctcggcatg    1440
gacgagctgt acaagtagat cttcgatccc taccggttag taatgagttt aaacggggga    1500
ggctaactga aacacggaag gagacaatac cggaaggaac ccgcgctatg acggcaataa    1560
aaagacagaa taaaacgcac gggtgttggg tcgtttgttc ataaacgcgg ggttcggtcc    1620
cagggctggc actctgtcga taccccaccg agtccccatt ggggccaata cgcccgcgtt    1680
tcttcctttt ccccacccca cccccaagt tcgggtgaag gcccagggct cgcagccaac    1740 gtcgggcgg caggccctgc catagctttt tggggcggct ttt                      1783
```